(12) United States Patent
Esfandyarpour

(10) Patent No.: US 10,093,975 B2
(45) Date of Patent: *Oct. 9, 2018

(54) SYSTEMS AND METHODS FOR HIGH EFFICIENCY ELECTRONIC SEQUENCING AND DETECTION

(71) Applicant: GENAPSYS, INC., Redwood City, CA (US)

(72) Inventor: Hesaam Esfandyarpour, Redwood City, CA (US)

(73) Assignee: GENAPSYS, INC., Redwood City, CA (US)

(*) Notice: Subject to any disclaimer, the term of this patent is extended or adjusted under 35 U.S.C. 154(b) by 535 days.

This patent is subject to a terminal disclaimer.

(21) Appl. No.: 14/361,902

(22) PCT Filed: Dec. 3, 2012

(86) PCT No.: PCT/US2012/067645
§ 371 (c)(1),
(2) Date: May 30, 2014

(87) PCT Pub. No.: WO2013/082619
PCT Pub. Date: Jun. 6, 2013

(65) Prior Publication Data
US 2014/0329699 A1    Nov. 6, 2014

Related U.S. Application Data

(60) Provisional application No. 61/565,651, filed on Dec. 1, 2011.

(51) Int. Cl.
| | | |
|---|---|---|
| C12Q 1/68 | (2018.01) |
| G01N 27/32 | (2006.01) |
| B03C 1/28 | (2006.01) |
| B03C 5/00 | (2006.01) |
| B03C 5/02 | (2006.01) |
| B01L 3/00 | (2006.01) |
| C12Q 1/6874 | (2018.01) |
| C12Q 1/6844 | (2018.01) |
| C12Q 1/6869 | (2018.01) |
| G01N 27/327 | (2006.01) |
| C12Q 1/6825 | (2018.01) |

(52) U.S. Cl.
CPC ...... *C12Q 1/6874* (2013.01); *B01L 3/502761* (2013.01); *B03C 1/286* (2013.01); *B03C 1/288* (2013.01); *B03C 5/005* (2013.01); *B03C 5/02* (2013.01); *B03C 5/022* (2013.01); *B03C 5/026* (2013.01); *C12Q 1/6825* (2013.01); *C12Q 1/6844* (2013.01); *C12Q 1/6869* (2013.01); *G01N 27/3278* (2013.01); *B01L 2200/0668* (2013.01); *B01L 2300/0636* (2013.01); *B01L 2300/0816* (2013.01); *B01L 2300/0819* (2013.01); *B01L 2400/043* (2013.01); *B01L 2400/0415* (2013.01); *B01L 2400/086* (2013.01); *B03C 2201/26* (2013.01)

(58) Field of Classification Search
None
See application file for complete search history.

(56) References Cited

U.S. PATENT DOCUMENTS

| | | |
|---|---|---|
| 2,014,761 A | 9/1935 | Faust |
| 4,072,576 A | 2/1978 | Arwin et al. |
| 5,344,545 A | 9/1994 | Tsukada et al. |
| 5,602,042 A | 2/1997 | Farber |
| 5,612,181 A | 3/1997 | Fourmentin-Guilbert |
| 5,795,782 A | 8/1998 | Church et al. |
| 5,834,197 A | 11/1998 | Parton |
| 6,046,097 A | 4/2000 | Hsieh et al. |
| 6,087,095 A | 7/2000 | Rosenthal et al. |
| 6,210,891 B1 | 4/2001 | Nyren et al. |
| 6,327,410 B1 | 12/2001 | Walt et al. |
| 6,632,655 B1 | 10/2003 | Mehta et al. |
| 6,833,246 B2 | 12/2004 | Balasubramanian |
| 6,953,958 B2 | 10/2005 | Baxter et al. |
| 7,081,192 B1 | 7/2006 | Wang et al. |
| 7,223,540 B2 | 5/2007 | Pourmand et al. |
| 7,242,241 B2 | 7/2007 | Toumazou et al. |
| 7,270,981 B2 | 9/2007 | Armes et al. |
| 7,282,370 B2 | 10/2007 | Bridgham et al. |
| 7,291,496 B2 | 11/2007 | Holm-Kennedy |
| 7,312,085 B2 | 12/2007 | Chou et al. |
| 7,317,216 B2 | 1/2008 | Holm-Kennedy |
| 7,323,305 B2 | 1/2008 | Leamon et al. |
| 7,361,466 B2 | 4/2008 | Korlach et al. |
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,615,382 B2 | 11/2009 | Wang et al. |

(Continued)

FOREIGN PATENT DOCUMENTS

| | | |
|---|---|---|
| CN | 1337580 A | 2/2002 |
| CN | 101120098 A | 2/2008 |

(Continued)

OTHER PUBLICATIONS

Rothberg et al. An integrated semiconductor device enabling non-optical genome sequencing. Nature. Jul. 20, 2011; 475(7356):348-52.*

(Continued)

*Primary Examiner* — Angela Marie Bertagna
*Assistant Examiner* — Olayinka A Oyeyemi
(74) *Attorney, Agent, or Firm* — Wilson Sonsini Goodrich & Rosati

(57) ABSTRACT

The present disclosure relates to systems and methods for high efficiency electronic sequencing of nucleic acids and molecular detection. In an example embodiment of the instant disclosure, the NanoNeedle may be utilized to detect a change in impedance resulting from the modulation of the counter ion concentration or Debye length associated with a biomolecule of interest, such as DNA or protein, for an application of interest, such as DNA sequencing, DNA hybridization, or protein detection.

15 Claims, 68 Drawing Sheets
Specification includes a Sequence Listing.

(56) References Cited

U.S. PATENT DOCUMENTS

| | | | |
|---|---|---|---|
| 7,645,596 B2 | 1/2010 | Williams et al. | |
| 7,649,358 B2 | 1/2010 | Toumazou et al. | |
| 7,666,598 B2 | 2/2010 | Piepenburg et al. | |
| 7,682,837 B2 | 3/2010 | Jain et al. | |
| 7,686,929 B2 | 3/2010 | Toumazou et al. | |
| 7,692,219 B1 | 4/2010 | Holm-Kennedy | |
| 7,695,907 B2 | 4/2010 | Miyahara et al. | |
| 7,763,427 B2 | 7/2010 | Piepenburg et al. | |
| 7,824,890 B2 | 11/2010 | Hoser et al. | |
| 7,875,440 B2 | 1/2011 | Williams et al. | |
| 7,888,013 B2 | 2/2011 | Miyahara et al. | |
| 7,932,034 B2 | 4/2011 | Esfandyarpour et al. | |
| 7,948,015 B2 | 5/2011 | Rothberg et al. | |
| 8,030,000 B2 | 10/2011 | Piepenburg et al. | |
| 8,062,848 B2 | 11/2011 | Goldstein et al. | |
| 8,062,850 B2 | 11/2011 | Piepenburg et al. | |
| 8,071,308 B2 | 12/2011 | Piepenburg et al. | |
| 8,114,591 B2 | 2/2012 | Toumazou et al. | |
| 8,128,796 B2 | 3/2012 | Ishige et al. | |
| 8,129,118 B2 | 3/2012 | Weindel et al. | |
| 8,137,569 B2 | 3/2012 | Harnack et al. | |
| 8,152,991 B2 | 4/2012 | Briman et al. | |
| 8,154,093 B2 | 4/2012 | Bradley et al. | |
| 8,173,401 B2 | 5/2012 | Chang et al. | |
| 8,179,296 B2 | 5/2012 | Kelly et al. | |
| 8,257,925 B2 | 9/2012 | Brown et al. | |
| 8,301,394 B2 | 10/2012 | Chen et al. | |
| 8,426,134 B2 | 4/2013 | Piepenburg et al. | |
| 8,460,875 B2 | 6/2013 | Armes et al. | |
| 8,518,670 B2 | 8/2013 | Goldstein et al. | |
| 8,574,846 B2 | 11/2013 | Piepenburg et al. | |
| 8,580,507 B2 | 11/2013 | Piepenburg et al. | |
| 8,585,973 B2 | 11/2013 | Esfandyarpour | |
| 8,637,253 B2 | 1/2014 | Piepenburg et al. | |
| 8,673,560 B2 | 3/2014 | Leamon et al. | |
| 8,969,002 B2 | 3/2015 | Esfandyarpour et al. | |
| 9,150,915 B2 | 10/2015 | Esfandyarpour et al. | |
| 9,184,099 B2 | 11/2015 | Baghbani-Parizi et al. | |
| 9,187,783 B2 * | 11/2015 | Esfandyarpour | C12Q 1/6853 |
| 9,274,077 B2 | 3/2016 | Esfandyarpour et al. | |
| 9,399,217 B2 * | 7/2016 | Esfandyarpour | C12Q 1/6853 |
| 2002/0132245 A1 | 9/2002 | Boles et al. | |
| 2002/0148739 A2 | 10/2002 | Liamos et al. | |
| 2003/0078314 A1 | 4/2003 | Johnson et al. | |
| 2003/0209432 A1 | 11/2003 | Choong et al. | |
| 2004/0014201 A1 | 1/2004 | Kim et al. | |
| 2004/0033492 A1 | 2/2004 | Chen | |
| 2004/0197793 A1 | 10/2004 | Hassibi et al. | |
| 2005/0009022 A1 | 1/2005 | Weiner et al. | |
| 2005/0019784 A1 | 1/2005 | Su et al. | |
| 2005/0123937 A1 | 6/2005 | Thorp et al. | |
| 2005/0129526 A1 | 6/2005 | Dukhin et al. | |
| 2006/0008824 A1 | 1/2006 | Ronaghi et al. | |
| 2006/0105373 A1 | 5/2006 | Pourmand et al. | |
| 2006/0222569 A1 | 10/2006 | Barten et al. | |
| 2007/0132043 A1 | 6/2007 | Bradley et al. | |
| 2007/0184463 A1 | 8/2007 | Molho et al. | |
| 2007/0275375 A1 | 11/2007 | Van Eijk | |
| 2008/0009420 A1 | 1/2008 | Schroth et al. | |
| 2008/0032295 A1 | 2/2008 | Toumazou et al. | |
| 2008/0161200 A1 | 7/2008 | Yu et al. | |
| 2008/0166727 A1 * | 7/2008 | Esfandyarpour | C12Q 1/6869 435/6.11 |
| 2008/0171325 A1 | 7/2008 | Brown et al. | |
| 2008/0176817 A1 | 7/2008 | Zhou et al. | |
| 2008/0187915 A1 | 8/2008 | Polonsky et al. | |
| 2008/0241841 A1 | 10/2008 | Murakawa et al. | |
| 2008/0286762 A1 | 11/2008 | Miyahara et al. | |
| 2008/0302732 A1 | 12/2008 | Soh et al. | |
| 2008/0318243 A1 | 12/2008 | Haga et al. | |
| 2009/0026082 A1 * | 1/2009 | Rothberg | C12Q 1/6869 204/556 |
| 2009/0029385 A1 | 1/2009 | Christians et al. | |
| 2009/0032401 A1 * | 2/2009 | Ronaghi | B01L 3/502761 204/549 |
| 2009/0048124 A1 | 2/2009 | Leamon et al. | |
| 2009/0127589 A1 | 5/2009 | Rothberg et al. | |
| 2009/0166221 A1 | 7/2009 | Ishige et al. | |
| 2009/0170716 A1 | 7/2009 | Su et al. | |
| 2009/0170724 A1 | 7/2009 | Balasubramanian et al. | |
| 2009/0181385 A1 | 7/2009 | McKernan et al. | |
| 2009/0191594 A1 | 7/2009 | Ohashi | |
| 2010/0000881 A1 | 1/2010 | Franzen et al. | |
| 2010/0035252 A1 | 2/2010 | Rothberg et al. | |
| 2010/0072080 A1 | 3/2010 | Karhanek et al. | |
| 2010/0078325 A1 | 4/2010 | Oliver | |
| 2010/0112588 A1 | 5/2010 | Farinas et al. | |
| 2010/0137143 A1 | 6/2010 | Rothberg et al. | |
| 2010/0137413 A1 | 6/2010 | Rothberg et al. | |
| 2010/0151479 A1 | 6/2010 | Toumazou et al. | |
| 2010/0159461 A1 | 6/2010 | Toumazou et al. | |
| 2010/0163414 A1 | 7/2010 | Gillies et al. | |
| 2010/0167938 A1 | 7/2010 | Su et al. | |
| 2010/0188073 A1 | 7/2010 | Rothberg et al. | |
| 2010/0197507 A1 | 8/2010 | Rothberg et al. | |
| 2010/0209922 A1 | 8/2010 | Williams et al. | |
| 2010/0255595 A1 | 10/2010 | Toumazou et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2010/0317531 A1 | 12/2010 | Balasubramanian et al. | |
| 2010/0330570 A1 | 12/2010 | Vander Horn et al. | |
| 2011/0039266 A1 | 2/2011 | Williams et al. | |
| 2011/0117026 A1 | 5/2011 | Tseng et al. | |
| 2011/0118139 A1 | 5/2011 | Mehta et al. | |
| 2011/0123991 A1 | 5/2011 | Hoser | |
| 2011/0159481 A1 | 6/2011 | Liu et al. | |
| 2011/0171655 A1 | 7/2011 | Esfandyarpour et al. | |
| 2011/0177498 A1 | 7/2011 | Clark et al. | |
| 2011/0183321 A1 | 7/2011 | Williams et al. | |
| 2011/0195253 A1 | 8/2011 | Hinz et al. | |
| 2011/0195459 A1 | 8/2011 | Hinz et al. | |
| 2011/0201057 A1 * | 8/2011 | Carr | C12Q 1/6848 435/91.5 |
| 2011/0201506 A1 | 8/2011 | Hinz et al. | |
| 2011/0217697 A1 | 9/2011 | Rothberg et al. | |
| 2011/0230375 A1 | 9/2011 | Rothberg et al. | |
| 2011/0241081 A1 | 10/2011 | Rothberg et al. | |
| 2011/0247933 A1 | 10/2011 | Rothberg et al. | |
| 2011/0248319 A1 | 10/2011 | Rothberg et al. | |
| 2011/0248320 A1 | 10/2011 | Rothberg et al. | |
| 2011/0259745 A1 | 10/2011 | Dehlinger et al. | |
| 2011/0263463 A1 | 10/2011 | Rothberg et al. | |
| 2011/0287432 A1 | 11/2011 | Wong et al. | |
| 2011/0287945 A1 | 11/2011 | Rothberg et al. | |
| 2011/0294115 A1 | 12/2011 | Williams et al. | |
| 2011/0311979 A1 | 12/2011 | Brown | |
| 2012/0013392 A1 | 1/2012 | Rothberg et al. | |
| 2012/0021918 A1 | 1/2012 | Bashir et al. | |
| 2012/0034607 A1 | 2/2012 | Rothberg et al. | |
| 2012/0037961 A1 | 2/2012 | Rothberg et al. | |
| 2012/0040844 A1 | 2/2012 | Rothberg et al. | |
| 2012/0045844 A1 | 2/2012 | Rothberg et al. | |
| 2012/0055811 A1 | 3/2012 | Rothberg et al. | |
| 2012/0055813 A1 | 3/2012 | Rothberg et al. | |
| 2012/0061255 A1 | 3/2012 | Rothberg et al. | |
| 2012/0061256 A1 | 3/2012 | Rothberg et al. | |
| 2012/0061733 A1 | 3/2012 | Rothberg et al. | |
| 2012/0065093 A1 | 3/2012 | Rothberg et al. | |
| 2012/0071363 A1 | 3/2012 | Rothberg et al. | |
| 2012/0085660 A1 | 4/2012 | Rothberg et al. | |
| 2012/0088682 A1 | 4/2012 | Rothberg et al. | |
| 2012/0094871 A1 | 4/2012 | Hinz et al. | |
| 2012/0129173 A1 | 5/2012 | Piepenburg et al. | |
| 2012/0129703 A1 | 5/2012 | Rothberg et al. | |
| 2012/0129728 A1 | 5/2012 | Rothberg et al. | |
| 2012/0129732 A1 | 5/2012 | Rothberg et al. | |
| 2012/0135870 A1 | 5/2012 | Rothberg et al. | |
| 2012/0135893 A1 | 5/2012 | Drmanac et al. | |
| 2012/0138460 A1 | 6/2012 | Baghbani-Parizi et al. | |
| 2012/0156728 A1 | 6/2012 | Li et al. | |
| 2012/0157322 A1 | 6/2012 | Myllykangas et al. | |

(56) References Cited

U.S. PATENT DOCUMENTS

| | | |
|---|---|---|
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour et al. |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0034880 A1 | 2/2013 | Oldham |
| 2013/0059290 A1 | 3/2013 | Armes et al. |
| 2013/0059762 A1 | 3/2013 | Leamon et al. |
| 2013/0090860 A1 | 4/2013 | Sikora et al. |
| 2013/0096013 A1 | 4/2013 | Esfandyarpour et al. |
| 2013/0109577 A1 | 5/2013 | Korlach et al. |
| 2013/0183211 A1 | 7/2013 | Senftleber |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0034497 A1 | 2/2014 | Davis et al. |
| 2014/0045701 A1 | 2/2014 | Esfandyarpour et al. |
| 2014/0057339 A1 | 2/2014 | Esfandyarpour et al. |
| 2014/0073531 A1 | 3/2014 | Esfandyarpour |
| 2014/0099674 A1 | 4/2014 | Piepenburg et al. |
| 2014/0106338 A1 | 4/2014 | Fischer et al. |
| 2014/0235457 A1 | 8/2014 | Esfandyarpour |
| 2014/0272952 A1 | 9/2014 | May et al. |
| 2015/0148264 A1 | 5/2015 | Hesaam et al. |
| 2015/0344943 A1 | 12/2015 | Florian |
| 2015/0368707 A1 | 12/2015 | Esfandyarpour et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2016/0340721 A1 | 11/2016 | Esfandyarpour |

FOREIGN PATENT DOCUMENTS

| | | | |
|---|---|---|---|
| CN | 101848757 A | | 9/2010 |
| CN | 102980922 A | | 3/2013 |
| EP | 0676623 A2 | | 10/1995 |
| EP | 1499738 B1 | | 7/2008 |
| EP | 1992706 A2 | | 11/2008 |
| EP | 2290096 A2 | | 3/2011 |
| EP | 2336361 A2 | | 6/2011 |
| EP | 2428588 A2 | | 3/2012 |
| EP | 2287341 B1 | | 2/2013 |
| EP | 1759012 B1 | | 5/2013 |
| EP | 2660336 A1 | | 11/2013 |
| JP | 2006512583 A | | 4/2006 |
| JP | 2008525822 A | | 7/2008 |
| WO | WO 01/18246 A1 | | 3/2001 |
| WO | WO-0137958 A2 | | 5/2001 |
| WO | WO 01/42508 A2 | | 6/2001 |
| WO | WO-0227909 A2 | | 4/2002 |
| WO | WO 02/061146 A1 | | 8/2002 |
| WO | WO 2005/008450 A2 | | 1/2005 |
| WO | WO 2005/108612 A2 | | 11/2005 |
| WO | WO 2005/121363 A2 | | 12/2005 |
| WO | WO-2007041619 A2 | | 4/2007 |
| WO | WO 2007/098049 A2 | | 8/2007 |
| WO | WO 2008/076406 A2 | | 6/2008 |
| WO | WO 2009/012112 A2 | | 1/2009 |
| WO | WO 2009/052348 A2 | | 4/2009 |
| WO | WO-2009074926 A1 | | 6/2009 |
| WO | WO 2009/122159 A2 | | 10/2009 |
| WO | WO 2009/150467 A1 | | 12/2009 |
| WO | WO 2010/008480 A2 | | 1/2010 |
| WO | WO 2010/075188 A2 | | 1/2010 |
| WO | WO-2010026488 A2 | | 3/2010 |
| WO | WO 2010/037085 A1 | | 4/2010 |
| WO | WO 2010/047804 A2 | | 4/2010 |
| WO | WO 2010/138187 A1 | | 12/2010 |
| WO | WO 2010/141940 A1 | | 12/2010 |
| WO | WO 2011/106556 A2 | | 9/2011 |
| WO | WO2012/047889 | * | 4/2012 ............... C12Q 1/68 |
| WO | WO 2012/047889 A2 | | 4/2012 |
| WO | WO-2012166742 A2 | | 12/2012 |
| WO | WO-2013082619 A1 | | 6/2013 |
| WO | WO-2013119765 A1 | | 8/2013 |
| WO | WO-2013188582 A1 | | 12/2013 |
| WO | WO 2014/012107 A2 | | 1/2014 |
| WO | WO 2014/043143 A1 | | 3/2014 |
| WO | WO-2014152625 A1 | | 9/2014 |
| WO | WO-2015089238 A1 | | 6/2015 |
| WO | WO-2015138696 A1 | | 9/2015 |
| WO | WO-2015161054 | | 10/2015 |

OTHER PUBLICATIONS

Rothberg et al. 2011 (pp. 1-25). Supplementary. Nature 475(7356): 1-25.*

Andreotti, et al. Immunoassay of infectious agents. Biotechniques. Oct. 2003;35(4):850-9.

Bell, et al. Detection of Bacillus anthracis DNA by LightCycler PCR. J Clin Microbiol. Aug. 2002;40(8):2897-902.

Boo, et al. Electrochemical nanoneedle biosensor based on multiwall carbon nanotube. Anal Chem. Jan. 15, 2006;78(2):617-20.

Esfandyarpour, et al. 3D Modeling of Impedance Spectroscopy for Protein Detection in Nanoneedle Biosensors. Proceedings of the International COMSOL Conference 2007, Boston, MA, USA, pp. 169-173 (Oct. 4-6, 2007).

Patolsky, et al. Fabrication of silicon nanowire devices for ultrasensitive, label-free, real-time detection of biological and chemical species. Nat Protoc. 2006;1(4):1711-24.

Gao, et al. Silicon nanowire arrays for label-free detection of DNA. Anal Chem. May 1, 2007;79(9):3291-7. Epub Apr. 4, 2007.

Guiducci, et al. A Biosensor for Direct Detection of DNA Sequences Based on Capacitance Measurements. ESSDERC 2002, pp. 479-482.

Esfandyarpour, et al. Geometrical Optimization of Pyrophosphate Concentration in Thermosequencing Platform for DNA Sequencing. Proceedings of the COMSOL Conf. 2007, Boston.

Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Dec. 4, 2009;27(6):3099-3103.

Office Action dated Mar. 4, 2016 for U.S. Appl. No. 14/081,358.

Office Action dated Oct. 5, 2015 for U.S. Appl. No. 14/081,358.

Patolsky, et al. Electrical detection of single viruses. Proc Natl Acad Sci U S A. Sep. 28, 2004;101(39):14017-22. Epub Sep. 13, 2004.

Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.

Safir, et al. Fabrication of an insulated probe on a self-assembled metallic nanowire for electrochemical probing in cells. IEEE 2006, pp. 898-900.

Yazdanpanah, et al. Selective self-assembly at room temperature of individual freestanding Ag2Ga alloy nanoneedles. J. Appl. Phys. 98, pp. 073510-7 (2005).

Zheng, et al. Multiplexed electrical detection of cancer markers with nanowire sensor arrays. Nat Biotechnol. Oct. 2005;23(10):1294-301. Epub Sep. 18, 2005.

U.S. Appl. No. 14/596,111, filed Jan. 13, 2015, Esfandyarpour et al.

Esfandyarpour, et al. A Novel Nanoneedle Biosensor for DNA Sequencing (abstract). Dec. 31, 2008. Available at http://www.nsti.org/Nanotech2008/showabstract.html?absno=1522.

European search report and search opinion dated Jan. 5, 2015 for EP Application No. 12792216.9.

Margulies, et al. Genome sequencing in microfabricated high-density picolitre reactors. Nature. Sep. 15, 2005;437(7057):376-80. Epub Jul. 31, 2005.

Office action dated Dec. 19, 2014 for U.S. Appl. No. 13/838,816.

U.S. Appl. No. 13/397,581, filed Feb. 15, 2012, Esfandyarpour et al.

U.S. Appl. No. 14/119,859, filed Nov. 22, 2013, Esfandyarpour et al.

(56) References Cited

OTHER PUBLICATIONS

Daniels, et al. Label-Free Impedance Biosensors: Opportunities and Challenges. Electroanalysis. May 16, 2007;19(12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Esfandyarpour, et al. 3D modeling of impedance spectroscopy for protein detection in nanoneedle biosensors. Proceedings of the COMSOL Conference 2007, Boston.
European search report and search opinion dated Mar. 12, 2014 for EP Application No. 11831452.5.
Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
Kitano, et al. Molecular structure of RNA polymerase and its complex with DNA. J Biochem. Jan. 1969;65(1):1-16.
Office action dated Jan. 28, 2014 for U.S. Appl. No. 13/838,816.
Office action dated Jan. 29, 2014 for U.S. Appl. No. 13/481,858.
Office action dated Jul. 18, 2013 for U.S. Appl. No. 13/481,858.
Office action dated Nov. 5, 2013 for U.S. Appl. No. 13/632,513.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158:24-29.
Senapati, et al. A nonamembrane-based nucleic acid sensing platform for portable diagnostics. Topics in Current Chemistry. 2011; 304:153-169.
Voelkerding, et al. Next generation sequencing: from basic research to diagnostics. Clin. Chem. 2009; 55(4):641-658.
Notice of allowance dated Nov. 21, 2014 for U.S. Appl. No. 13/632,513.
Notice of allowance dated Dec. 15, 2015 for U.S. Appl. No. 13/838,816.
Office action dated Dec. 17, 2015 for U.S. Appl. No. 13/481,858.
Office action dated Dec. 17, 2015 for U.S. Appl. No. 14/835,070.
Notice of allowance dated Mar. 28, 2016 for U.S. Appl. No. 3/481,858.
Co-pending U.S. Appl. No. 14/835,070, filed Aug. 25, 2015.
Co-pending U.S. Appl. No. 14/859,725, filed Sep. 21, 2015.
Edman; et al., "Electric field directed nucleic acid hybridization on microchips.", Dec. 15, 1997, 25(24), 4907-14.
"Notice of allowance dated Aug. 25, 2015 for U.S. Appl. No. 14/596,111.".
"Notice of allowance dated Sep. 1, 2015 for U.S. Appl. No. 14/596,111.".
"Office action dated Oct. 7, 2015 for U.S. Appl. No. 13/838,816.".
Sosnowski; et al., "Rapid determination of single base mismatch mutations in DNA hybrids by direct electric field control.", Feb. 18, 1997, 94(4), 1119-23.
Zhang; et al., "Dielectrophoresis for manipulation of micro/nano particles in microfluidic systems.", Jan. 2010, 396(1), 401-20.
Notice of allowance dated Dec. 3, 2015 for U.S. Appl. No. 13/838,816.
Notice of allowance dated May 19, 2016 for U.S. Appl. No. 13/481,858.
Brouns; et al., "Small CRISPR RNAs guide antiviral defense in prokaryotes.", Aug. 15, 2008, 321(5891), 960-4.
Carte; et al., "Cas6 is an endoribonuclease that generates guide RNAs for invader defense in prokaryotes.", Dec. 15, 2008, 22(24), 3489-96.
Cho; et al., "Bis-aptazyme sensors for hepatitis C virus replicase and helicase without blank signal.", Nov. 27, 2005, 33(20), e177.
Co-pending U.S. Appl. No. 14/653,230, filed Jun. 17, 2015.
Dimov; et al., "Stand-alone self-powered integrated microfluidic blood analysis system (SIMBAS).", Mar. 7, 2001, 11(5), 845-50.
Ellington; et al., "In vitro selection of RNA molecules that bind specific ligands.", Aug. 30, 1990, 346(6287), 818-22.
"European search report and search opinion dated Jul. 13, 2015 for EP Application No. 12852490.7.".
Gardeniers; et al., "Silicon micromachined hollow microneedles for transdermal liquid transport.", 2003, 12(6), 855-862.
Haurwitz; et al., "Sequence- and structure-specific RNA processing by a CRISPR endonuclease.", Sep. 10, 2010, 329(5997), 1355-8.
Kaushik; et al., "Lack of pain associated with microfabricated microneedles.", Feb. 2001, 92(2), 502-4.
Kim; et al., "Replication of DNA microarrays prepared by in situ oligonucleotide polymerization and mechanical transfer.", Oct. 1, 2007, 79(19), 7267-74.
Kunin; et al., "Evolutionary conservation of sequence and secondary structures in CRISPR repeats.", 2007, 8(4), R61.
Kurosaki; et al., "Rapid and simple detection of Ebola virus by reverse transcription-loop-mediated isothermal amplification.", Apr. 2007, 141(1), 78-83.
Lin; et al., "Replication of DNA microarrays from zip code masters.", Mar. 15, 2006, 128(10), 3268-72.
Liu; et al., "Immobilization of DNA onto poly(dimethylsiloxane) surfaces and application to a microelectrochemical enzyme-amplified DNA hybridization assay.", Jul. 6, 2004, 20(14), 5905-10.
Makarova; et al., "A putative RNA-interference-based immune system in prokaryotes: computational analysis of the predicted enzymatic machinery, functional analogies with eukaryotic RNAi, and hypothetical mechanisms of action.", Mar. 16, 2006, 1:7, 26 pages.
"Notice of allowance dated Jul. 1, 2015 for U.S. Appl. No. 13/824,129.".
"Notice of allowance dated Jul. 13, 2015 for U.S. Appl. No. 14/596,111.".
Notomi; et al., "Loop-mediated isothermal amplification of DNA.", Jun. 15, 2000, 28(12), E63.
Sivamani; et al., "Microneedles and transdermal applications.", Jan. 2007, 4(1), 19-25.
Terns; et al., "CRISPR-based adaptive immune systems.", Jun. 2011, 14(3), 321-7.
Van; Der Oost et al., "CRISPR-based adaptive and heritable immunity in prokaryotes.", Aug. 2009, 34(8), 401-7.
Wang; et al., "Interaction of the Cas6 riboendonuclease with CRISPR RNAs: recognition and cleavage.", Feb. 9, 2011, 19(2), 257-64.
Didion; et al., "Invaders: Recognition of Double-Stranded DNA by Using Duplexes Modified with Interstrand Zippers of 2'-O-(Pyren-1-yl)methyl-ribonucleotides.", doi: 10.1002/cbic.201300414. Epub Aug. 23, 2013 Sep 2, 14(13), 1534-1538.
International search report and written opinion dated Oct. 26, 2015 for PCT/US2015/026135.
International search report and written opinion dated Aug. 21, 2014 for PCT Application No. PCT/US2014/027544.
Javanmard, et al. A microfluidic platform for electrical detection of DNA hybridization. Sens Actuators B Chem. May 20, 2011;154(1):22-27. Epub Mar. 30, 2010.
Office action dated Sep. 2, 2014 for U.S. Appl. No. 13/632,513.
Lee, et al. Ion-sensitive field-effect transistor for biological sensing. Sensors (Basel). 2009;9(9):7111-31. doi: 10.3390/s90907111. Epub Sep. 7, 2009.
Office action dated Jan. 30, 2015 for U.S. Appl. No. 13/481,858.
Office action dated Apr. 9, 2015 for U.S. Appl. No. 14/596,111.
Co-pending U.S. Appl. No. 14/688,764, filed Apr. 16, 2015.
Notice of allowance dated Jun. 3, 2015 for U.S. Appl. No. 14/596,111.
Cagnin, et al. Overview of electrochemical DNA biosensors: new approaches to detect the expression of life. Sensors (Basel). 2009;9(4):3122-48. doi: 10.3390/s90403122. Epub Apr. 24, 2009.

(56) References Cited

OTHER PUBLICATIONS

Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.
Office action dated Jul. 23, 2014 for U.S. Appl. No. 13/824,129.
Office action dated Jul. 25, 2014 for U.S. Appl. No. 13/481,858.
Sabounchi, et al. Sample concentration and impedance detection on a microfluidic polymer chip. Biomed Microdevices. Oct. 2008;10(5):661-70. doi: 10.1007/s10544-008-9177-4.
Office action dated May 1, 2015 for U.S. Appl. No. 13/824,129.
Office action dated Apr. 6, 2016 for U.S. Appl. No. 14/835,070.
Co-pending U.S. Appl. No. 15/183,406, filed Jun. 15, 2016.
Co-pending U.S. Appl. No. 15/360,369, filed Nov. 23, 2016.
Co-pending U.S. Appl. No. 15/655,616, filed Jul. 20, 2017.
Notice of Allowance dated May 12, 2017 for U.S. Appl. No. 14/653,230.
Notice of Allowance dated Jul. 6, 2017 for U.S. Appl. No. 14/653,230.
Notice of Allowance dated Jul. 10, 2017 for U.S. Appl. No. 14/688,764.
Notice of Allowance dated Jul. 20, 2017 for U.S. Appl. No. 4/688,764.
Notice of Allowance dated Jul. 31, 2017 for U.S. Appl. No. 14/119,859.
Office Action dated Feb. 14, 2017 for U.S. Appl. No. 14/653,230.
Office Action dated Apr. 5, 2017 for U.S. Appl. No. 14/859,725.
Office Action dated Apr. 24, 2017 for U.S. Appl. No. 14/119,859.
International Search Report and Written Opinion dated Nov. 16, 2017 for International PCT Patent Application No. PCT/US2017/43159.
Co-pending U.S. Appl. No. 15/726,193, filed Oct. 5, 2017.
Co-pending U.S. Appl. No. 15/726,217, filed Oct. 5, 2017.
European Search Report dated Oct. 11, 2017 for European Patent Application No. EP14869402.9.
Notice of Allowance dated Sep. 8, 2017 for U.S. Appl. No. 14/653,230.
Office Action dated Oct. 23, 2017 for U.S. Appl. No. 14/859,725.
Peng et al. Interdigitated Array Electrodes with Magnetic Function as a Particle-Based Biosensor. Sensors, 2007 IEEE. pp. 1097-1100.
Saias et al. Design, modeling and characterization of microfluidic architectures for high flow rate, small footprint microfluidic systems. Lab Chip. Mar. 7, 2011;11(5):822-32.
Tamayol et al. Laminar Flow in Microchannels With Noncircular Cross Section. J. Fluids Eng 132(11), 111201 (Nov. 3, 2010) (9 pages).
U.S. Appl. No. 14/859,725 Notice of Allowance dated May 30, 2018.
U.S. Appl. No. 15/230,048 Notice of Allowance dated Apr. 5, 2018.
Co-pending U.S. Appl. No. 16/007,829, filed Jun. 13, 2018.
Co-pending U.S. Appl. No. 16/007,969, filed Jun. 13, 2018.
U.S. Appl. No. 15/028,899 Notice of Allowance dated Jun. 27, 2018.
U.S. Appl. No. 15/183,406 Office Action dated Jun. 21, 2018.

\* cited by examiner 1100    1120    1120

FIG. 12B

In case of constant
speed flow:
t ~ = t₀ + dt

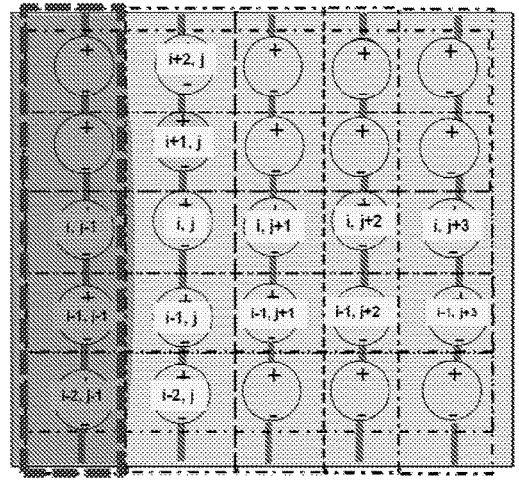

t ⱼ₋₁ is the time that the flow hit the "j-1"
column (in average).

The time that we like to monitor
the reaction of cells in column j-1
is around (record the signal of j-1
column sensors):

dtⱼ₋₁ ~ = tⱼ - tⱼ₋₁ (+ treaction)

rather than continues read out of the cells

FIG. 12C

In case of
constant speed
flow :
t ⱼ₊₁ ~ = t₀ + 3dt

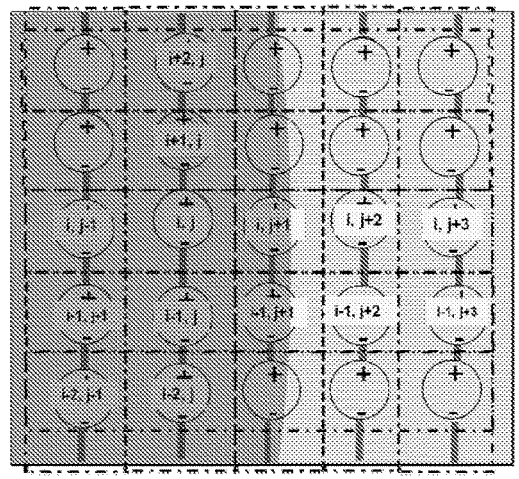

t ⱼ₊₁ is the time that the flow hit the "j+1"
column (in average) at first point.

The time that we like to monitor
the reaction of cells in column j+1
is around (record the signal of j+1
column sensors):

dtⱼ₊₃ ~ = tⱼ₊₂ - tⱼ₊₁ (+ treaction)

rather than continues read out of the cells

FIG. 12D

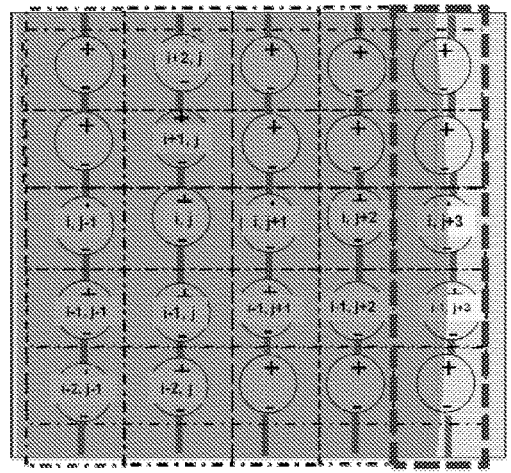

In case of constant speed flow :
$t_{j+3} \sim = t_0 + 5dt$ $t_{j+3}$ is the time that the flow hit the "j+3" column (in average) at first point.

The time that we like to monitor the reaction of cells in column j+3 is around (record the signal of j+3 column sensors):

$dt_{j+3} \sim = t_{j+4} - t_{j+3}$ (+ $t_{reaction}$)

rather than continues read out of the cells

FIG. 12E

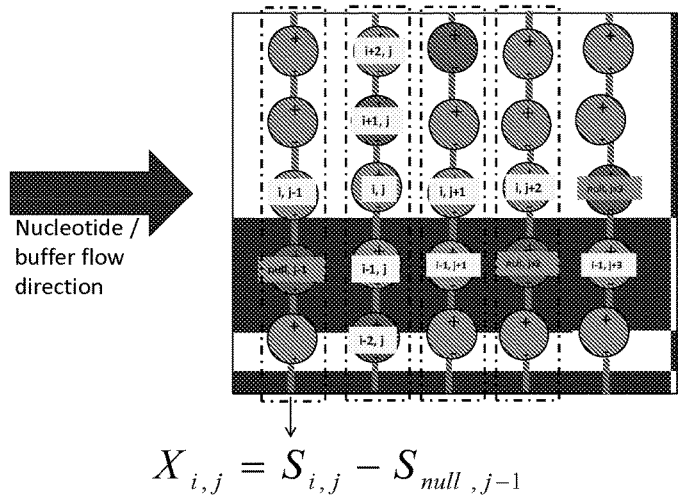

Nucleotide / buffer flow direction $$X_{i,j} = S_{i,j} - S_{null,j-1}$$

$$X_{i,j} = S_{i,j} - S_{no\ bead,j}$$

$$X_{i,j} = S_{i,j} - S_{no\ reaction,j}$$

FIG. 12L

Calibration:
- Monitor the effect of a DNA-bead signal (or any signal) from a pixel on the neighbor cells (by reading with the neighbor sensors).
- Extract the nxn matrix of $A_{i,j}$ for each pixel/cell either in time or frequency domain
- post processing the output signals during the sequencing of beads by inverse post-processing.

$$A_{i,j}(t) = \begin{bmatrix} \dots & A_{(k,p)} & \dots \\ & f(\text{cell }(k,p)\text{ over cell}(i,j)) & \end{bmatrix}$$

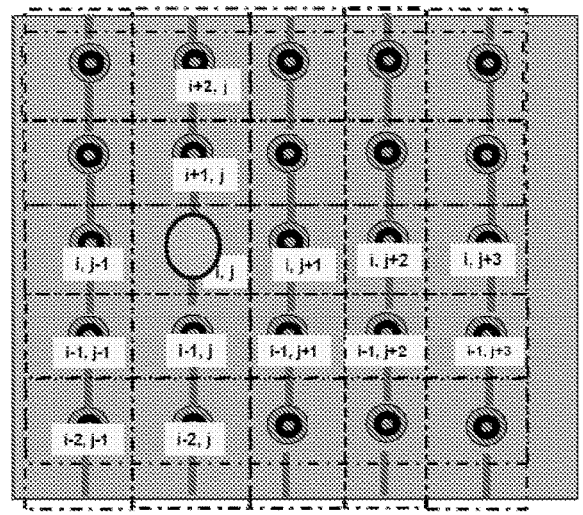

$A_{i,j}(k,p) = f(\text{cell }(k,p)\text{ over cell}(i,j))$

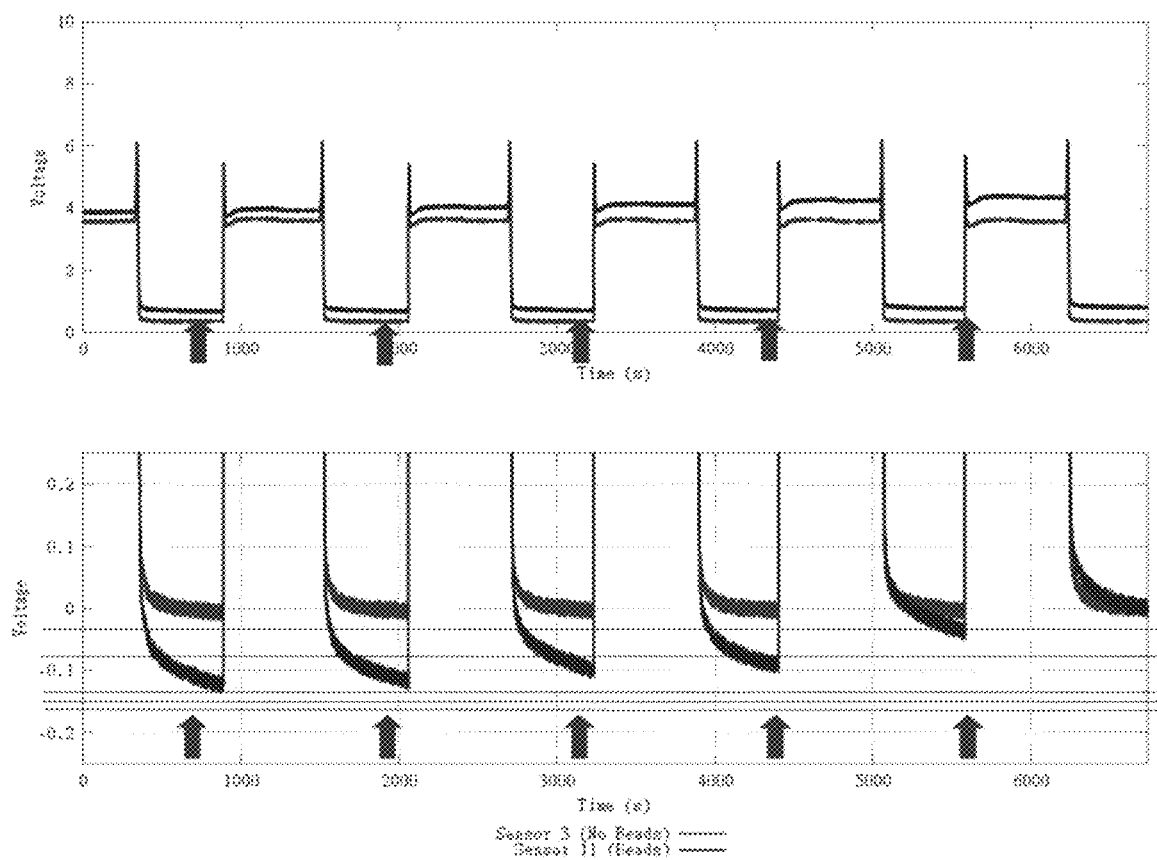

"ATGGAATTGGGAAAAATA" (SEQ ID NO: 3)

$2(V) + 2(V)\sin(800t)$

SYSTEMS AND METHODS FOR HIGH EFFICIENCY ELECTRONIC SEQUENCING AND DETECTION

This application is a national phase entry of PCT Application No. PCT/US2012/067645, filed Dec. 3, 2012, which claims priority to U.S. Provisional Application No. 61/565,651 filed Dec. 1, 2011, titled "GENIUS ELECTRONIC SEQUENCING TECHNOLOGIES AND METHODS THEREFOR". The disclosure of U.S. Provisional Application No. 61/565,651 is hereby incorporated by reference in its entirety.

The subject matter of this application is related to U.S. Provisional Application No. 61/389,490 filed Oct. 4, 2010, U.S. Provisional Application No. 61/389,484 filed Oct. 4, 2010, U.S. Provisional Application No. 61/443,167 filed Feb. 15, 2011, U.S. Provisional Application No. 61/491,081 filed May 27, 2011, U.S. Provisional Application No. 61/620,381 filed Apr. 4, 2012, U.S. application Ser. No. 13/397,581 filed Feb. 15, 2012, U.S. application Ser. No. 13/632,513 filed Oct. 1, 2012, and U.S. application Ser. No. 13/118,044 filed May 27, 2011 each of which is hereby incorporated by reference in its entirety.

The NanoBridge may function as a pH sensor, as described in U.S. Published Patent Application No. US 2012/0138460, titled "BIOSENSOR DEVICES, SYSTEMS AND METHODS THEREFOR", which is hereby incorporated by reference in its entirety.

This application is related to PCT/US2011/054769, which is hereby incorporated by reference in its entirety.

This application is further related to PCT/US2012/039880, which is hereby incorporated by reference in its entirety.

SEQUENCE LISTING

The instant application contains a Sequence Listing which has been filed electronically in ASCII format and is hereby incorporated by reference in its entirety. Said ASCII copy, created on Nov. 3, 2016, is named 42808-701_833_SL.txt and is 1,126 bytes in size.

BACKGROUND

Methods for quick and cost effective genetic and biological analysis, including high-throughput DNA sequencing, remain an important aspect of advancing personalized medicine and diagnostic testing. Current high throughout or miniaturized systems have limitations. For example, current systems for DNA sequencing, including those that employ optical detection, are cumbersome and expensive, and have limited throughput. While some systems use sensors and sequencing flow cells to address these limitations, these are generally one-time use disposables, which substantially increases the cost to the user and limits the complexity of the sensor, since the sensor must be cost effectively manufactured for a single use.

SUMMARY

In an aspect, the present disclosure provides a method for sequencing a nucleic acid molecule, comprising: (a) providing a plurality of particles adjacent to a sensor array, wherein an individual particle of the plurality of particles is positioned adjacent to an individual sensor of the sensor array, wherein the nucleic acid molecule is attached to the individual particle and has a primer hybridized thereto; (b) bringing the nucleic acid molecule having the primer hybridized thereto in contact with nucleotides under conditions sufficient to conduct a polymerization reaction to yield a nucleic acid strand complementary to the nucleic acid molecule; (c) using the individual sensor to measure steady state signals indicative of impedance, charge, or conductivity change within a Debye length of the individual particle or the nucleic acid molecule, to identify individual incorporation events associated with the nucleotides during the polymerization reaction; and (d) using the steady state signals to identify a sequence of the nucleic acid strand, thereby sequencing the nucleic acid molecule.

BRIEF DESCRIPTION OF THE DRAWINGS

FIG. 12B schematically illustrates a reagent slug that has entered the flow cell; FIG. 12C schematically illustrates a reagent slug that has entered the flow cell sufficiently to interact with a set of colonies; FIG. 12D schematically illustrates a reagent slug that has traversed through the flow cell; FIG. 12E schematically illustrates null beads that may be used as references for differential measurements; FIG. 12L schematically illustrates example differential measurements taken using a cross-talk deconvolution function matrix.

FIGS. 18A and 18B show examples of raw data output for DNA sequencing based on steady state detection;

A need exists for systems and methods for genetic and biological analysis, and in particular, methods and systems for highly parallel or clonal sequencing reactions that are both sensitive and cost effective

DETAILED DESCRIPTION

NanoNeedle

A NanoNeedle type of biosensor may be used for characterizing biochemical species such as antibodies and antigens, and/or for applications involving one or more of DNA sequencing, DNA hybridization, Real Time PCR, protein or other bio-species and chemical-species detection.

In an example embodiment of the instant disclosure, the NanoNeedle may be utilized to detect a change in impedance resulting from the modulation of the counter ion concentration or Debye length associated with a biomolecule of interest, such as DNA or protein, for an application of interest, such as DNA sequencing, DNA hybridization, or protein detection. For example, in DNA sequencing, a change in impedance is associated with the incorporation of a nucleotide and this change can be utilized to detect the incorporation event and identity of the DNA sequence. The nucleotides may be injected in a known order, thus allowing for identification of the complementary base by detection of the incorporation through impedance measurement. The biomolecules, such as single strand DNA, may attach to a carrier, such as a bead, or may be bound directly onto the surface of a substrate.

The physical location of the electrodes of the NanoNeedle with respect to their proximity to a carrier, such as a bead, to which DNA is bound, may impact the sensitivity of the impedance measurement. For example, if there is not adequate physical alignment between the electrodes of a NanoNeedle and a carrier, such as a bead, to which DNA is bound, the sensor impedance may be dominated by the impedance of the bulk reagent. If, for example, the impedance of the bulk reagent constitutes 90 percent of the total impedance between the electrodes, and the impedance of the DNA on the bead and its associated counter ions constitutes 10 percent of the total impedance between the electrodes, a one percent change in the impedance of the DNA and associated counter ions will result in a 0.1 percent change in the total impedance between the electrodes. In order to maximize the ability of the sensor to measure the percent change in total impedance between the electrodes, while minimizing interference from the impedance of the bulk reagent, the locations of the sensor electrodes can be modified with respect to their distance from the beads.

Figure 1A:
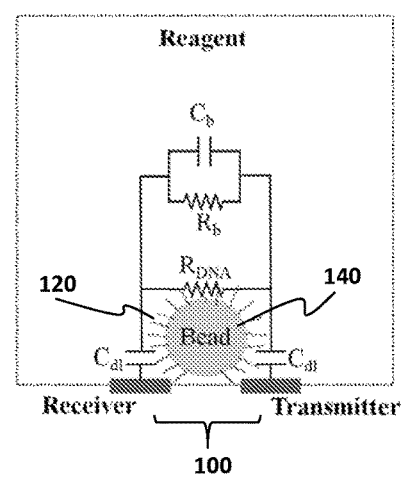
FIG. 1A provides a schematic demonstrating various paths that may be detected by receiving and transmitting electrodes.

FIG. 1A provides a schematic demonstrating various paths that may be detected by the receiving and transmitting electrodes 100. $C_b$ and $R_b$ represent the capacitance and resistance due to the bulk solution, respectively. $R_{DNA}$ is the resistance due to the region in close proximity of the template DNA strands 120 fixed on the bead 140. $R_{DNA}$ is different than $R_b$ due to the modified concentration of mobile ions in close proximity and associated to the fixed DNA strands (in Debye layer of the beads and/or DNA strands). Modulation of $R_{DNA}$ due to nucleotide incorporation on the template DNA strand 120 fixed on the bead 140 can be used by Nanoneedle to detect the incorporation event, thus the sequence of DNA strand 120. $C_{dl}$ is the double layer capacitance around receiving and transmitting electrodes 100.

There is a $C_{DNA}$, not shown, associated with the bead and DNA strands fixed on the bead, which is effectively in parallel to $R_{DNA}$ in the model as a lump element.

Figure 1B:
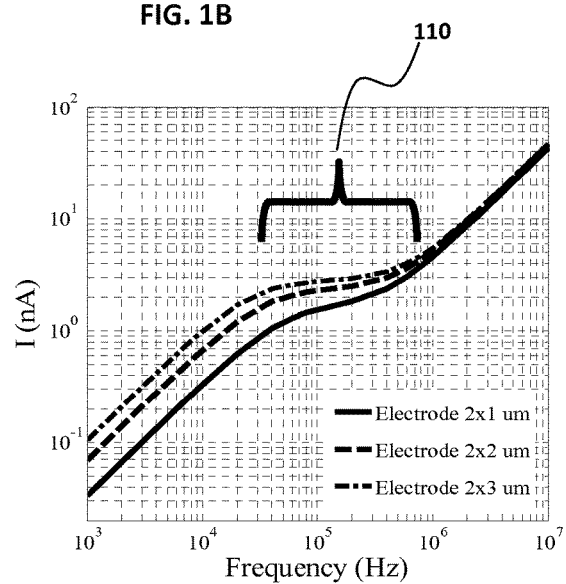
FIG. 1B shows a sensor that may operate around mid-range frequency in order to help eliminate the effect of any capacitances between electrodes.
Figure 1C:
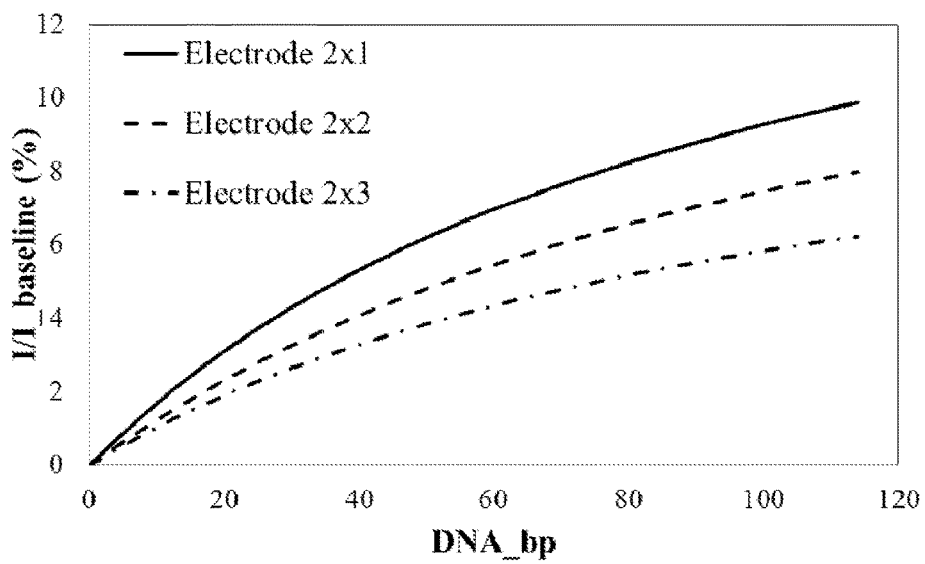
FIG. 1C shows an operating condition that may depend on electrode size as well as a spacing of the transmitter and receiver electrodes.

Referring now to FIG. 1B, to measure the change in resistance due to nucleotide incorporation, the sensor may operate around mid-range frequency 110 in order to help eliminate the effect of any capacitances between electrodes. In some embodiments, this operating condition depends on the electrode size as well as the spacing of the transmitter and receiver electrodes, as shown in FIG. 1C. This figure shows that decreasing the length of the electrodes may lead to an increase in sensitivity, as can be seen by a larger change in the percentage of current over baseline current as the reaction, for example, the incorporation of nucleotide base pairs for DNA sequencing, proceeds. At low frequencies, the double layer capacitance may dominate the impedance and the sensitivity of the sensor to changes in resistance can become small. At very high frequencies, the parasitic capacitance between the two electrodes may dominate. The current goes directly through that area and the sensitivity to changes in resistance decreases. Therefore, based on the electrode size and geometry, the optimum operating condition can be achieved for the highest sensitivity of the sensor.

Figure 1D:
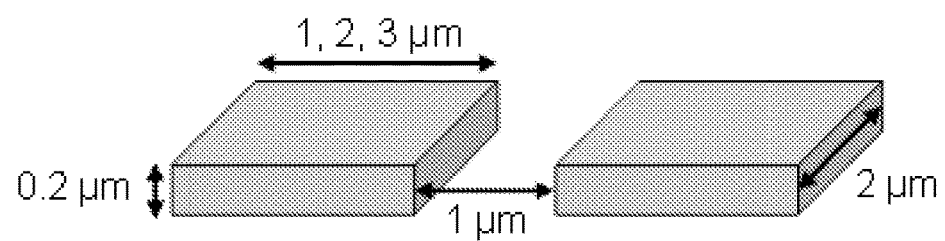
FIG. 1D shows an illustration of example electrode dimensions.
Figure 1E:
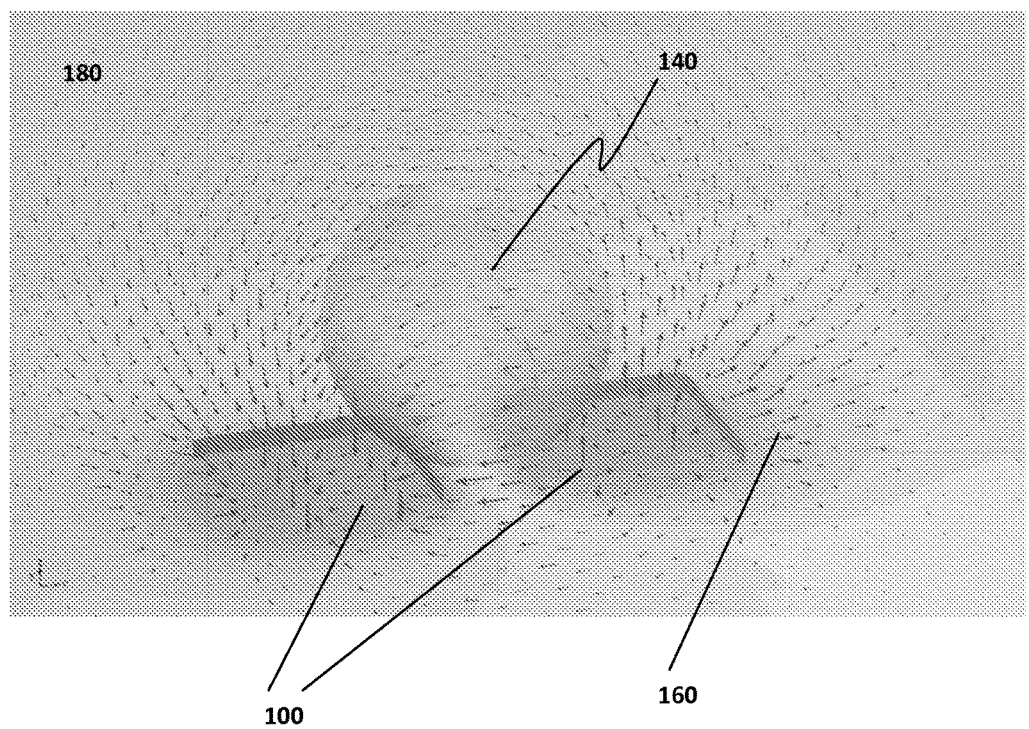
FIG. 1E shows an example of electric field lines at the electrodes.

FIG. 1D provides an illustration of some potential electrode embodiments and an exemplary range in electrode length (1-3 μm). The electrode sizes can be 7 nm to 70 nm or between 70 nm to 700 nm or between 700 nm to 7 μm, in length, weight and depth. The electric field lines 160 of FIG. 1E show how the portions of the electrodes that are the farthest from the bead mainly sense changes in the resistance or capacitance of the bulk solution 180. The electric field lines at the portions of the electrodes that are farthest from the bead have a direction that points away from the bead, indicating that the current path is through the reagent, not around the bead. In some embodiments where the electrodes are smaller and closer to the bead, a larger portion of current goes around the bead, which can increase the sensitivity of the sensor. There may be an optimum electrode configuration that increases the baseline current as well as sensitivity in order to better detect the DNA incorporation events.

In some embodiments, it may be desirable to bring the sensor electrodes for a sensor such as a NanoNeedle in close proximity to a bead, in order to minimize the amount of bulk reagent volume, which may exist between the NanoNeedle electrodes and the bead or particle. One embodiment may have a bead held in a flat or mostly flat surface through magnetic or electric fields or attachment via a linker. One embodiment may have a bead held in a depression as shown in FIGS. 2A, 2B and 2C.

Figure 2A:
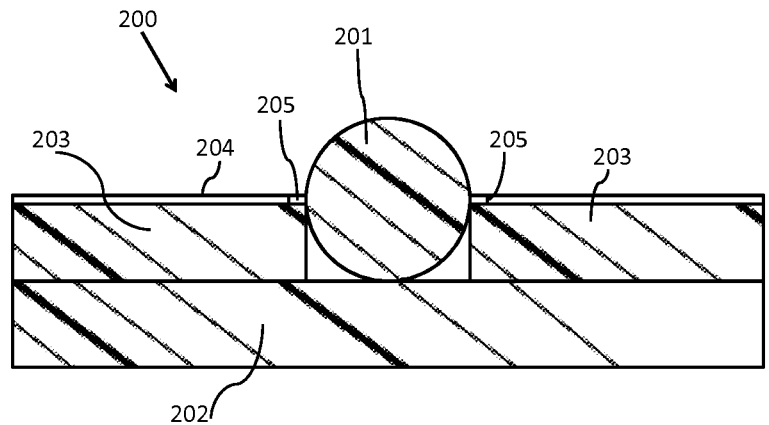
FIG. 2A schematically illustrates a depression that may be formed from a material.

As shown in FIG. 2A, the depression may be formed from a material, such as for example a dielectric layer 203, that is deposited on a substrate 202, and the material forming the depression may have an active area 205 for the sensing of a target reaction formed upon said material. The active area 205 of electrodes 204 may sense the target molecules and/or target reaction. The depression may be used to retain a carrier, such as a bead 201 that is exposed to bulk solution 200.

Figure 2B:
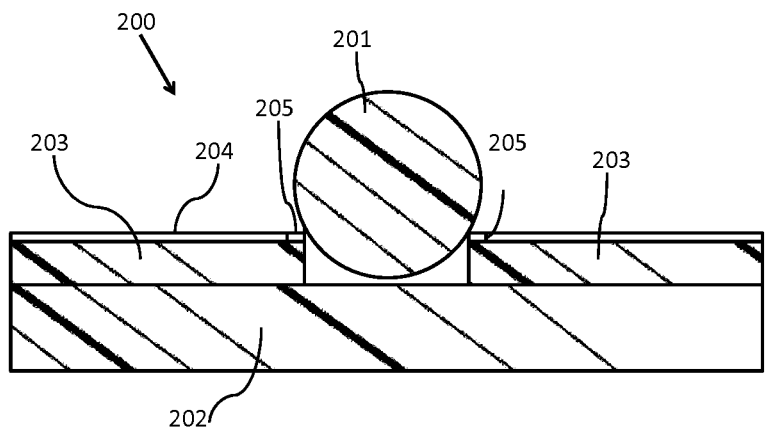
FIG. 2B schematically illustrates a material with a shallower depression than FIG. 2A.

FIG. 2B shows a further embodiment, similar to that of FIG. 2A, except with a shallower depression to allow for more of the surface area of bead 201 to be exposed to bulk solution 200. This embodiment may be desirable in that the surface area of bead 201 is more exposed to bulk solution 200 and this may lead to more efficient reagent delivery to the bead surface and may allow for more target molecules to bind to the surface, potentially enhancing the signal from the target reaction that can be detected by the active area 205.

Figure 2C:
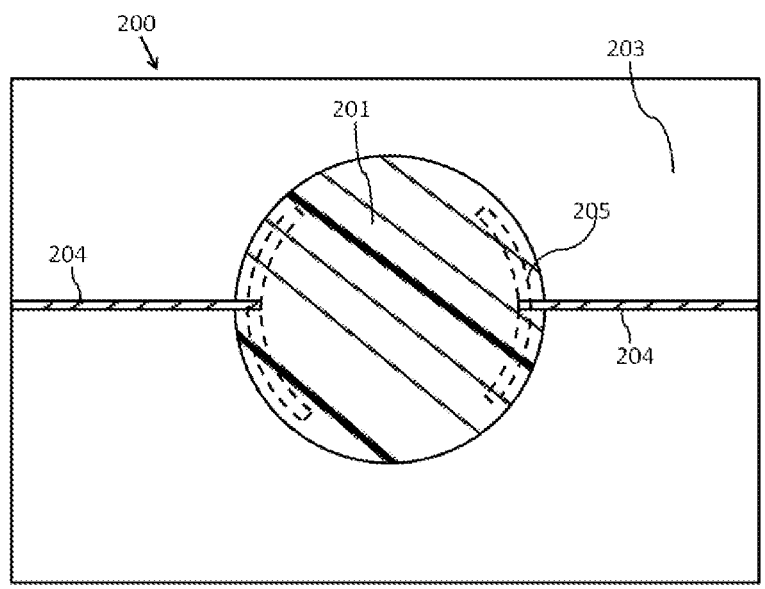
FIG. 2C schematically illustrates a top view of an example of a NanoNeedle sensor.

FIG. 2C shows a top view of a further embodiment of the NanoNeedle sensor wherein the active area 205 is formed into an arc that may conform to the edge of the depression formed into dielectric layer 203, and thus to the edge of the bead. The active area 205 may be connected to electrodes 204 and this NanoNeedle embodiment is exposed to bulk solution 200 for the detection of target molecules and/or reactions. The electrodes 204 may have horizontal traces or may directly goes down to a read out circuitry, for example a CMOS read out circuitry in the underlying layer. In a high density array of NanoNeedle sensors, the signal from the target reaction that can be detected by the active area 205 of a sensor in the array that may have different shape and/or sizes. The array of the sensors may be 100 to 100,000 sensors or 100,0000 to 1 million or 1 million to 10 million or 10 million to 100 million or 100 million to 1 billion sensor per array.

The electrodes may thus be within the Debye length of the surface of the bead or particle and the DNA attached or bound thereto. The NanoNeedle device may permit a minimum influence on the total impedance between the NanoNeedle electrodes by the bulk reagent solution, and a maximum influence by the DNA attached to or bound to the surface of the bead or particle.

In some other embodiments, a bead may be held on a flat surface without any depression. In such embodiments, the sensor or the electrodes of the NanoNeedle may be in close proximity to the DNA coated beads, but there is no depression or cavity and the bead is placed on a flat or almost flat surface, held by a virtual field force, including but not limited to a magnetic field or an electric field or a combination of different forces. In this manner, in a further embodiment, an array of "virtual wells" can be created, shown in FIG. 3. These virtual wells 300 may also be referred to as "confinement cells" 300 because the magnetic or electric forces may confine target particles, such as template DNA, on or near the bead 320 in some embodiments. Depending on the structure and operation of a "virtual well" or "confinement cell", they may work as a "three dimensional cage" or reactor. The reactor can be used for different applications such as amplification, isolation, confinement, concentration, detection of chemical or biological species. For example, it can be used for high efficiency emulsion free amplification of DNA, or high efficiency DNA or RNA synthesis, or DNA hybridization array, etc.

Figure 3:
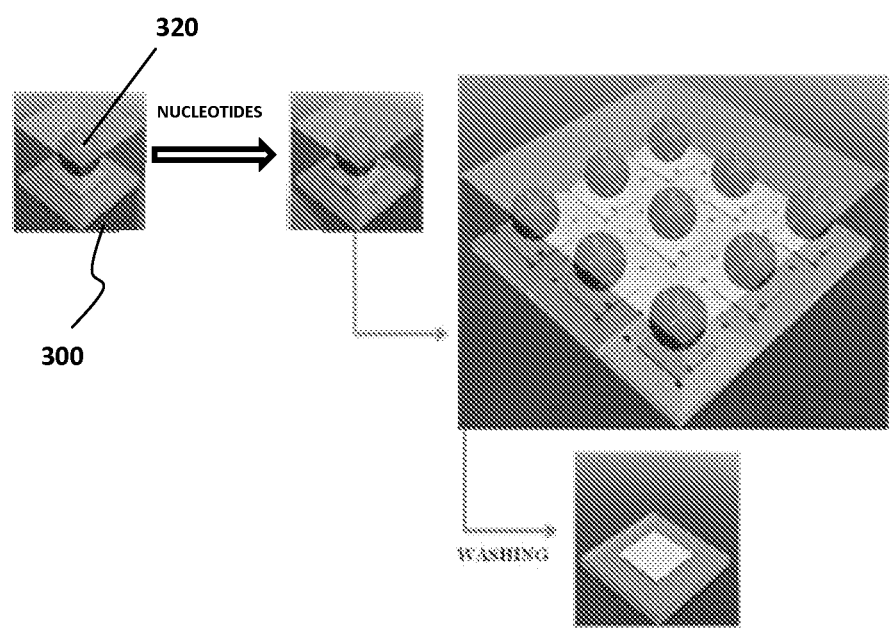
FIG. 3 schematically illustrates an example of a bead loaded into a confinement cell.

In one embodiment, as illustrated by FIG. 3, the bead 320 is loaded into the confinement cell and may have target particles, such as DNA template, already attached. Nucleotides or other reagents may be injected into the array of virtual wells/confinement cells. After the target reaction, such as DNA sequencing, is completed and detected by a sensor, such as a NanoNeedle or NanoBridge or other type of sensors, the reagents, target molecules, and beads may be washed. This method may allow for a re-usable array of confinement cells 300. Using a confinement cell instead of a depression or a physical well may be desirable because it may allow for easier washing of beads, reagents, and target molecules that may otherwise become lodged in the depression and may be difficult to remove. In one embedment, an electric field may contain or move the nucleotides, a DNA strand, or other molecules around the bead and/or template DNA.

In a further embodiment, the bead can be placed through a physical linker to the surface of the substrate of the nanosensor array.

Figure 4A:
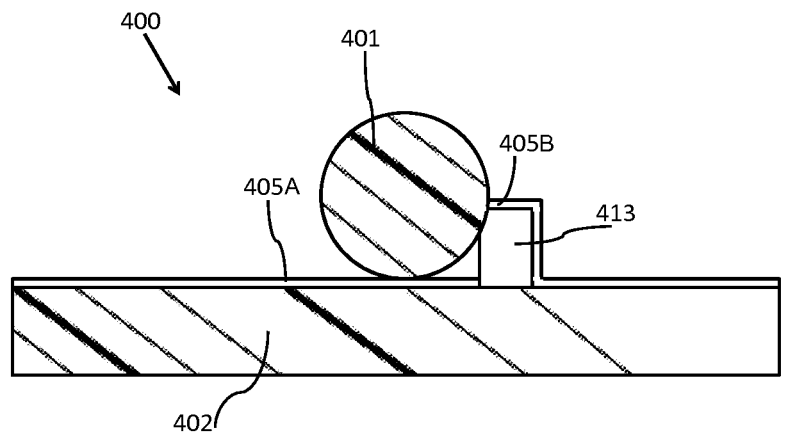
FIG. 4A schematically illustrates an electrode that may be attached directly to the substrate.

In an alternative embodiment, as shown in FIG. 4A, one electrode 405A may be attached directly to the substrate 402. The second electrode 405B on the NanoNeedle may be attached upon a portion of the sensor 413 which is utilized to position the bead 401 or particle in a fixed location. The bead or particle is thus in contact with both electrodes, minimizing the influence of the bulk reagent solution 400 on the total impedance between the NanoNeedle electrodes 405A and 405B, as opposed to the impedance resulting from the counter ions within the Debye length associated with the bead or particle and the DNA that is attached or bound to the bead or particle, the impedance measurement of interest.

Figure 4B:
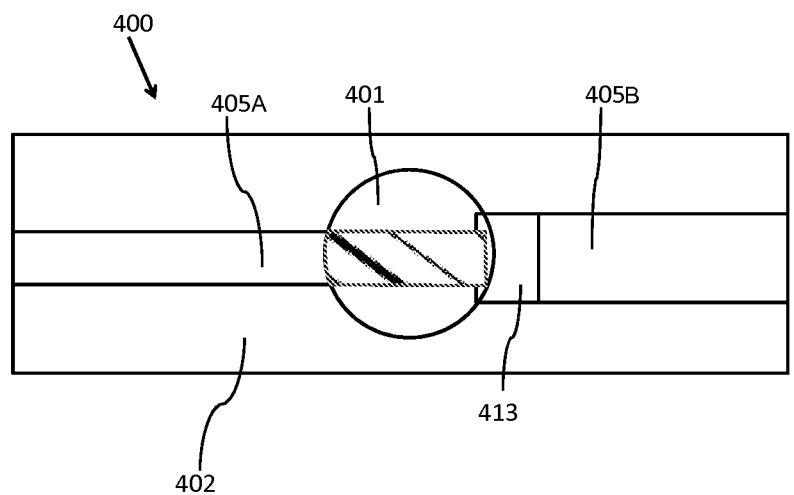
FIG. 4B schematically illustrates a top view of an electrode that may be attached directly to the substrate.

A top view of the embodiment, as shown in FIG. 4A, is shown in FIG. 4B. This top view shows the electrode 405A, which may be attached directly to the substrate 402, underneath and in close proximity to the bead 401. A second electrode 405B may be in contact with sensor 413, which is utilized to position the bead 401 in a fixed location.

Figure 4C:
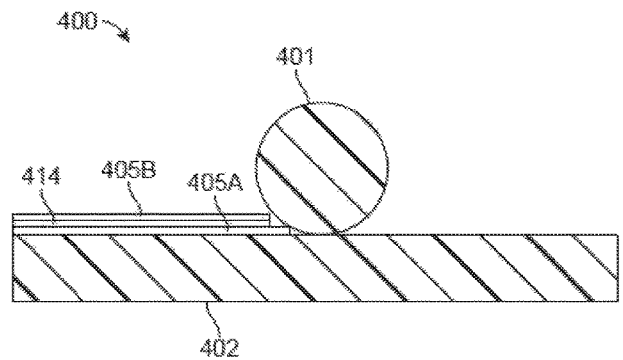
FIG. 4C schematically illustrates a bead that may be held in place on a substrate.

In a further embodiment, as shown in FIG. 4C, the bead 401 or particle may be held in place on a substrate 402. A first electrode 405A of a NanoNeedle may be attached directly to the substrate 402, or to an adhesion layer (not shown) adhered to said substrate. A dielectric layer 414 may then be fabricated so as to cover said first electrode. A second electrode 405B of a NanoNeedle may then be fabricated above the dielectric and said first electrode of the NanoNeedle. The second electrode may be shorter than the first electrode. A slope may be created due to the difference in length between the electrodes, so as to conform to the curve of the bead. The difference in the length may be a function of the diameter of the bead or particle, and the thickness of the two electrodes and the dielectric between the electrodes. In this manner, the electrodes may be in contact with the bead, or may be in very close proximity to the bead, such that the impedance resulting from the counter ions within the Debye length associated with the bead or particle and the DNA which is attached or bound to the bead or particle is greater than the impedance of the bulk reagent solution 400.

In some embodiments, the placement of the bead or particle on a substrate may be via a physical well or depression, or it may be achieved by holding the bead through a magnetic or electric force or physical binding through a linker mechanism and/or compound or combination of two or more of the methods.

Shielding the electrodes using a dielectric substrate may also maximize the impedance measurement by the sensor. The substrate may be composed or fabricated from glass, quartz, plastic, or any other dielectric material. In some embodiments, silicon substrate can be covered by a dielectric layer such as silicon oxide, silicon nitride, or other oxide layer, or even polymers such as polydimethylsiloxane (PDMS), SU8, or another polymer. This type of substrate is used in order to minimize current flow through the substrate, thus enhancing the change in impedance around the bead and maximizing the desired signal output to the sensor.

In another embodiment, some portion of one or both electrodes may be covered by a dielectric layer. In some embodiments, the portions of the electrodes in closest proximity to the bead or DNA remain uncovered. These embodiments may optimize the impedance measurements of the sensor by shielding the electrodes. These configurations can assist in preventing the measurement of impedance from bulk solution.

In one embodiment, a tip of one or both electrodes is coated with a thin dielectric layer. This thin dielectric layer provides a barrier between the electrode and the solution, reducing the amount and/or rate of corrosion. In this manner, the effective lifetime of the coated electrode may be extended as compared to the lifetime of the electrode without the thin dielectric layer. The thickness of the layer may be between 0.3 nm to 10 nm and in some embodiments the thickness may be more than 10 nm.

This coating also allows for selection from a wider range of electrode materials that may otherwise not function as desired when exposed to the bulk solution. For example, Aluminum, Copper, Tungsten, or other materials that are susceptible to corrosion, may be chosen as the electrode material and coated with a thin dielectric layer. This also allows the selection of a material that may not otherwise be compatible with CMOS fabrication processes. Furthermore, this allows for the selection of a material that may be less expensive. This thin dielectric layer can be coated via atomic layer deposition (ALD) or other fabrication techniques. The NanoNeedle may operate in alternating current (AC) mode, and thus the signal can pass through thin dielectric layer. In an embodiment, the electrode material can be made of silicon or other semiconductor materials, such as doped polysilicon or doped crystal silicon. The material may have a native oxide layer or a doped thin layer.

In some embodiments, there may be a ground or a shield layer (or a low impedance conductive acting as a shield) in addition to a dielectric layer near the electrodes. In a further embodiment, the ground/shield layer is located in the substrate base layer, for example, located in the silicon base. This ground/shield layer may be a metal, such as for example copper, aluminum, platinum, gold or another metal. The ground/shield layer may reduce signal interference from the bulk solution or from the base material, such that the signal through the electrodes is optimized to measure the change in conductance due to nucleotide incorporation. In another embodiment, the ground/shield layer may be located above the electrodes and surrounded by a dielectric layer. The ground/shield layer may reduce signal interference from the bulk solution, as may impede the variation or noise in the bulk solution from impacting the electrodes or traces of electrodes that are not in close proximity to the sensors.

In one embodiment, the ground/shield layer may cover a portion of the transmitter electrodes, but not cover the receiving electrodes. In another embodiment, two separate ground/shield layers maybe used to cover portions of the receiving electrodes and portions of the transmitter electrodes. The two separate ground/shield layers for the transmitter and receiver electrodes may provide additional isolation between the electrodes and further increase the sensitivity of the system to measure the change in the conductance due to nucleotide incorporation.

In some embodiments, the NanoNeedle may be coupled with a local capacitor, or capacitors, associated with one or both electrodes, in order to prevent influence from direct current (DC) bias levels from the driver circuit or leakage from within the chip sensor from influencing the output signal.

Figure 4D:
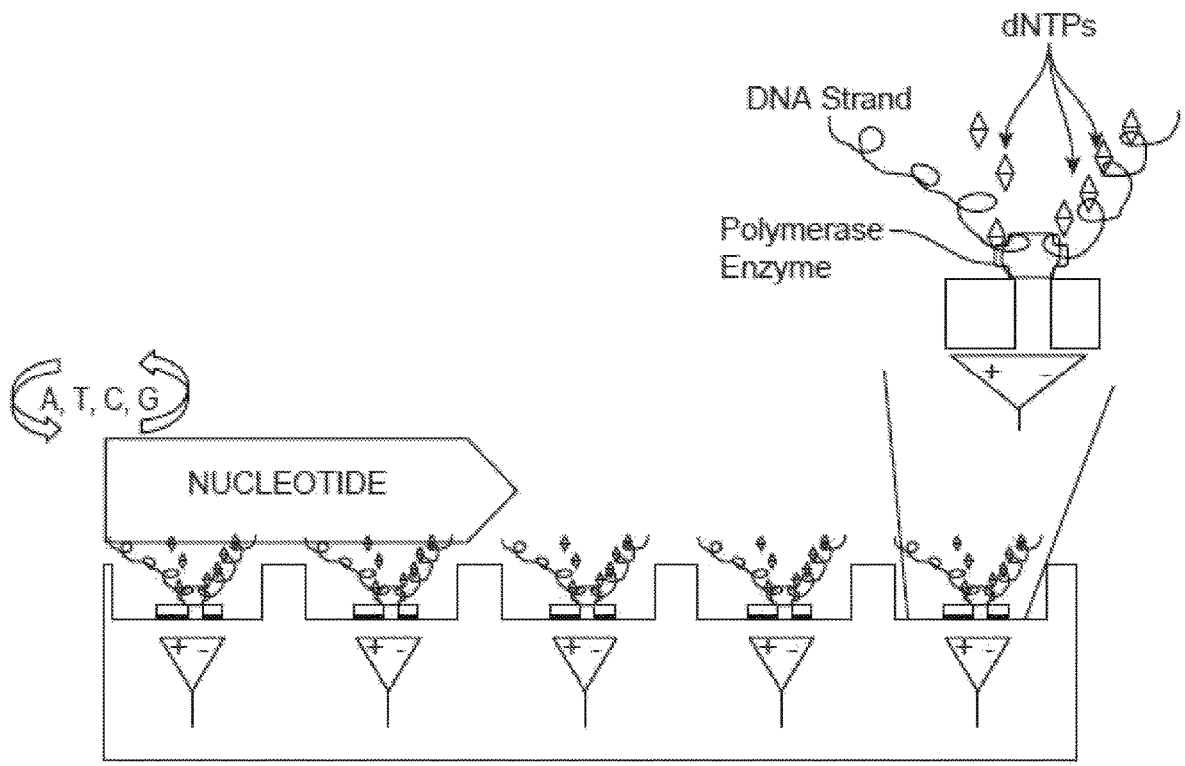
FIG. 4D schematically illustrates a polymerase or linker molecule that may be attached to the surface of a sensor.

The NanoNeedle may be fabricated as a planar structure, or may be fabricated as a coaxial structure. The NanoNeedle structures may be fabricated in an array of NanoNeedles, permitting large numbers of single DNA molecules to be sequenced at the same time. The polymerase or a linker molecule can be attached to the surface of the sensor, for example on the dielectric layer between the two electrodes, or attached to one of the electrodes, and then DNA strand can incorporate with nucleotide resulting to change the detectable impedance between the two electrodes, as shown in FIG. 4D.

In an alternative embodiment, other molecules and assays may be utilized, most particularly those that allow detection of kinetics of single molecule reactions, such as other enzymatic reactions. The NanoNeedle or NanoBridge array can be used for the detection of single or a plurality of molecules for DNA sequencing.

Figure 5A:
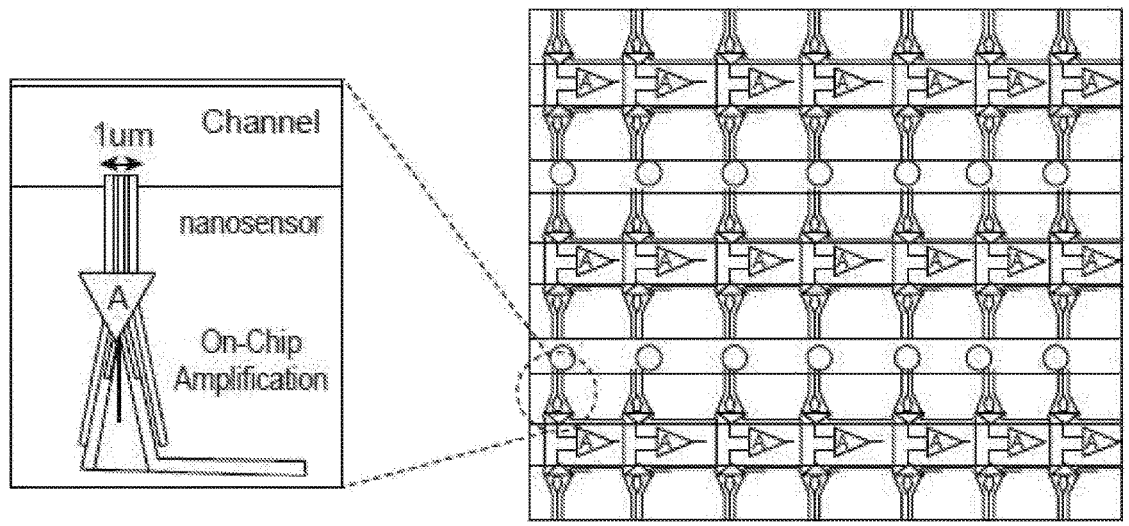
FIG. 5A schematically illustrates an example of a NanoNeedle array.
Figure 5B:
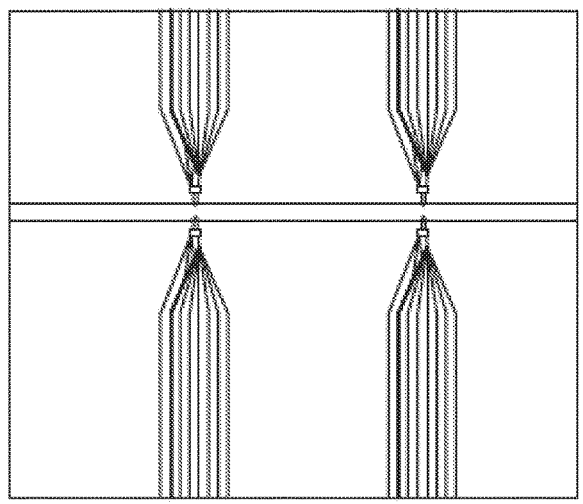
FIG. 5B shows a photomicrograph of a top view of an example of a NanoNeedle sensor in a microfluidic channel.

In some embodiments, the array is a NanoNeedle array as shown in FIG. 5A, which illustrates both the close up view of a NanoNeedle (left) and a top view of the NanoNeedle array (right). The close up view of the NanoNeedle sensor shows one embodiment where the sensor is 1 µm in width and is in contact with the microfluidic channel wherein the target molecules are located. FIG. 5B is a photomicrograph of a top view of one embodiment of NanoNeedle sensors in a microfluidic channel. In some embodiments, amplification of the signal occurs in the channel and is detected by the nanosensor. This process is referred to as on-chip amplification because the amplification occurs within the microfluidic or in close proximity of the nanosensor chip that comprises the nanosensor array.

In one embodiment this on-chip amplification can be through using a chemical reaction or process to amplify the signal. In some embodiments, for example, a polymerase enzyme, such as T4 polymerase, can be used for amplification of inorganic pyrophosphate or PPi concentration, in the region close to the bead and the sensor. In one embodiment, for example, an enzyme such as pyrophosphate can be used to divide diphosphate or pyrophosphate into two phosphate groups, resulting in different ion concentrations. Different chemical amplification can be used for increasing the signal detection with the nanosensors. In some embodiments, the amplification of the signal occurs with a local amplifier close the nanosensor.

Figure 6:
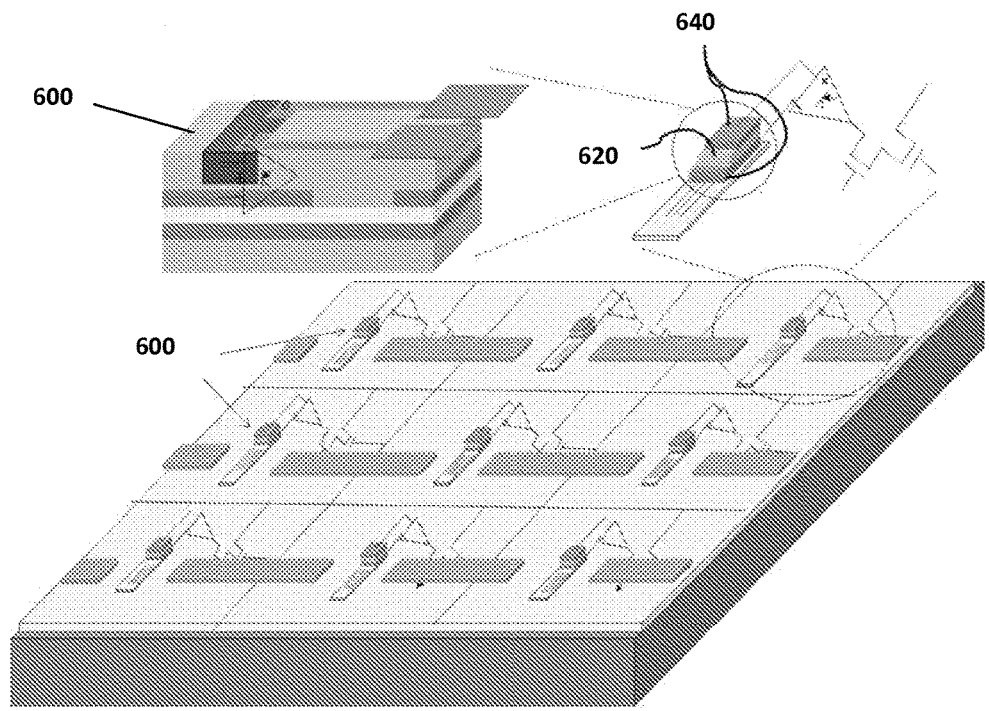
FIG. 6 schematically illustrates another example of a NanoNeedle array.

FIG. 6 shows a schematic of a NanoNeedle array, with a close up view of the NanoNeedle sensor 600 at the top. In some embodiments of the NanoNeedle, the electrode 620 is partially covered by and rests upon dielectric layers 640. In some embodiments, the NanoNeedle sensor may be composed of two inter-circled or "coaxial tip" electrodes or similar shapes.

Figure 7:
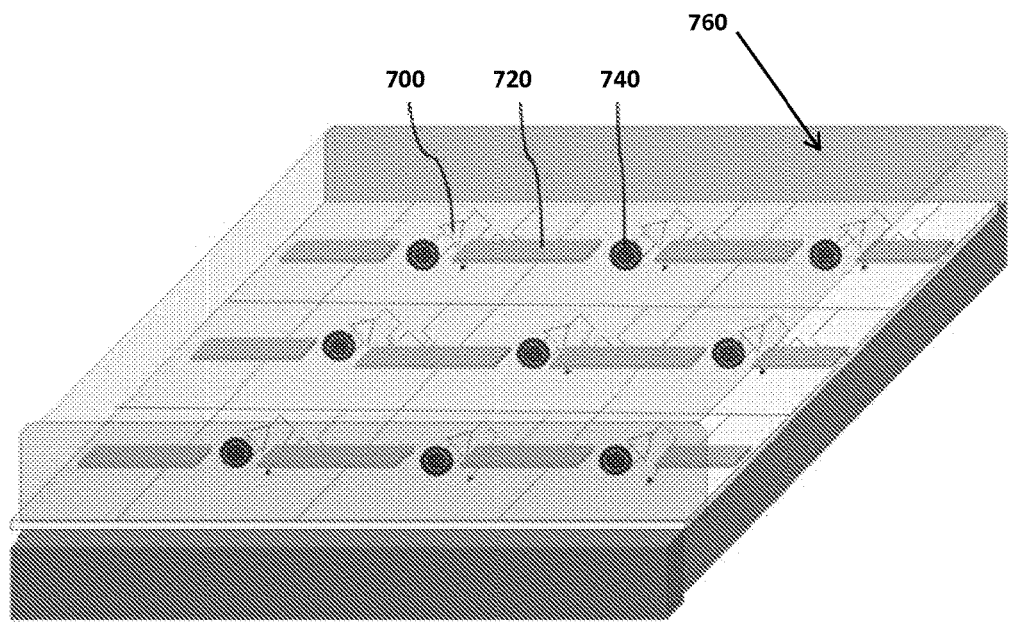
FIG. 7 schematically illustrates an array of NanoNeedle or NanoBridge sensors that may be associated with a carrier.

In a further embodiment, shown in FIG. 7, the array of NanoNeedle or NanoBridge sensors are associated with a carrier, such as for example a bead 740, in order to bind a target molecule, such as DNA for DNA sequencing. The nanosensor 700 may be proximate to a magnetic region 720 that can retain a magnetic bead 740. The array is exposed to bulk solution 760, wherein target particles and reagents such as DNA and nucleotides (dNTPs) are introduced for reactions of interest, such as for example DNA sequencing. The magnetic region 720 may be formed in a rectangular bar structured as shown in FIG. 7 or any other shape, for example a circular or square or other shapes, to capture the beads, on or in close proximity of the magnetic regions.

In some embodiments, the NanoNeedle may operate via a DC signal. The measurement may be achieved by detection of the change in the DC signal, for example, current, and/or the modulation of the electric field, or the change in ion concentration between the two electrodes. In one embodiment, a change in the rate of electrolysis (oxidation-reduction reaction) may be used as an indication of the occurrence of reactions of interest, for example, in DNA sequencing this change may indicate the incorporation of nucleotides. This change may occur due to the modulation of impedance associated with the concentration of ions between the two electrodes. This change in ion concentration may also result from the byproducts associated with nucleotide incorporation, such as protons, inorganic pyrophosphates (PPi), or the counter ion concentration due to the increase in the negative charge of the DNA molecules.

In some embodiments, chemical layers may be used to amplify the signal or the oxidation/reduction effect. These chemical layers may also reduce bubble formation at the electrodes. For such embodiments, materials or polymers, such as the ones with reversible oxidation-reduction properties, can be used, for example, hydroquinone (HQ) and p-benzoquinone (Q).

In some embodiments, Quinhydrone (QH), which is a complex of HQ and Q, may be added to the flow stream in the microfluidic nanoarray. By increasing the concentration of QH to increase the current, filming and deposition of QH on the electrodes can occur. The greater the increase in concentration of HQ, the more molecules may be available near the electrodes for a reduction oxidation (redox) reaction. If the concentration of HQ is low, then after a short period of time the area around the electrodes may become depleted of one product (for example, H2Q near anode and Q near cathode) and the reaction may stop at that point. In some embodiments, it can be desirable for the concentration to be high enough to ensure that there is sufficient H2Q available or diffused in close proximity to the anode electrode to continue the reaction. In one embodiment, a sensor such as a NanoNeedle can operate at very low frequencies such that an electrode may switch between anodic and cathodic roles wherein HQ, Q, and H2Q may be always available near the electrodes. The low frequency can be 0.01 Hz to 10 Hz or 10 Hz to 1000 Hz or more. In some embodiments, this low frequency can be optimized based on the concentration of HQ products and the diffusion rate in buffer. The applied voltage can be a combination of low frequency and high frequency signals.

Figure 8:
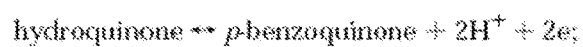
FIG. 8 shows water hydrolysis that may occur near the positive electrode of a cell in a nanosensor array.
Figure 8:
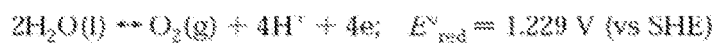
Figure 8:
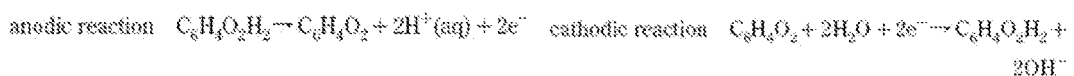

In the case of water hydrolysis near the positive electrode of a cell in the nanosensor array, $O_2$ bubbles and $H^+$ ions may be generated. In some embodiments, the bubble problem can be overcome by adding a chemical to the solution where the discharge potential of the chemical is less than that of water, and as a result no gas is generated. HQ has a hydrolysis voltage which is less than that of water (0.6V versus 1.2V, respectively) and thus a lower discharge potential, as shown in FIG. 8, and this may allow for the application of lower voltages through the electrodes with a resulting signal that may be the same or increased as compared to solution without HQ. The HQ-Q redox reaction may address the bubble problem, but the redox reaction can generate H+ ions, thereby lowering the pH. In a further embodiment, this problem may be addressed by adding HQ to a sequencing and/or amplification buffer, in order to regulate the pH such that it may be closer to the desired pH, such as for example a pH level that is approximately 7.

In some embodiments, the NanoNeedle can be configured to operate as a temperature sensor and/or a pH sensor to detect nucleotide incorporations. This method is further described in US patent application 2008/0166727 entitled "Heat and pH measurement for sequencing of DNA, which is hereby incorporated in its entirety.

Figure 9A:
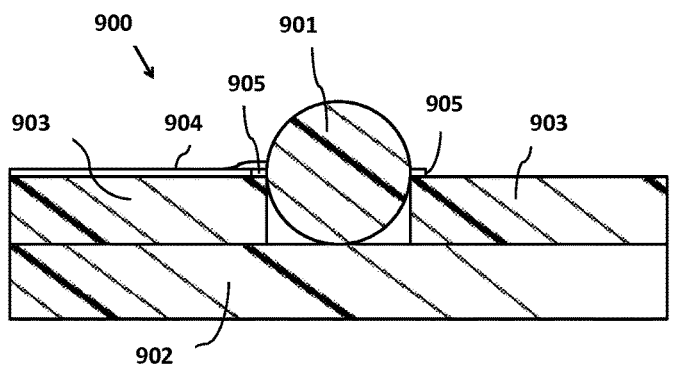
FIG. 9A schematically illustrates a side view of an example of a ring NanoBridge sensor.
Figure 9B:
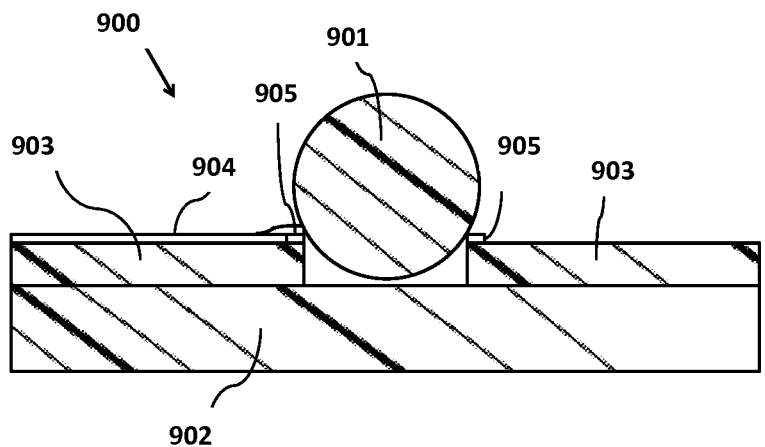
FIG. 9B shows an example of a ring NanoBridge sensor with a support structure smaller than the diameter of the bead or particle.
Figure 9C:
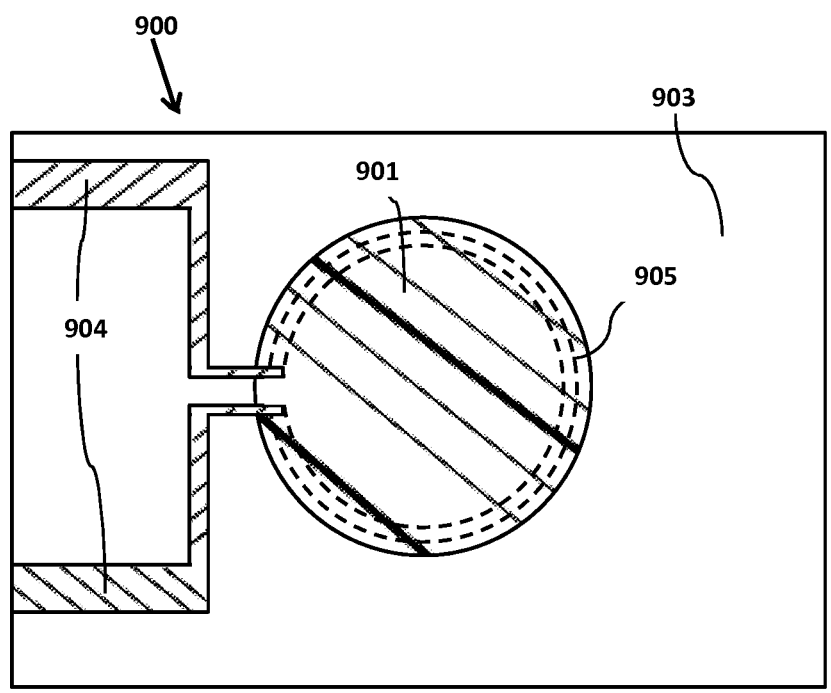
FIG. 9C schematically illustrates a top view of an example of a NanoBridge sensor implemented with a ring structure.

In some embodiments, the sensor may be a NanoBridge sensor wherein the active area may be fabricated such that said active area partially encircles the bead or particle, and is in immediate proximity to said bead or particle, as shown in FIG. 9A, FIG. 9B, and FIG. 9C.

FIG. 9A is a side view of a "ring" NanoBridge, where the inner portion of the active area 905 is within the Debye length of the bead 901 or particle and the DNA, which may be bound thereto. The active area may be entirely within the Debye length of said bead or particle, resulting in impedance of the entire active area changing in response to changes in the charge that is bound or associated with the bead or particle and/or the incorporation event of a nucleotide or nucleotide analog. The electrical conductors 904 provide a means for measuring the impedance of the active area 905. The diameter of the ring and the associated supporting structure 903 may be sized such that a bead fits closely within said ring, and may be located above substrate 902. In some embodiments, the change in conductance or impedance of the NanoBridge is due to the impact of the ion concentration modulation, for example, due to the release of ions such as protons or release of inorganic pyrophosphates via nucleotide incorporation.

Alternatively, as shown in FIG. 9B, the ring 905 and support structure 903 may be sized to be smaller than the diameter of the bead 901 or particle, such that a bead may rest upon the ring, particularly when held by a magnetic array or electric field, ensuring that the ring is within the Debye length of the bead or particle and the DNA bound thereto. The ring structure can also be used for other structures.

FIG. 9C is a top view of a NanoBridge implemented with a ring structure, showing the overlap of the bead 901 over the active area 905 of the sensor, and the electrical conductors 904 that may provide a means to measure the impedance of the active area 905.

Depending on the desired characteristics of the output signal, the embodiment shown in FIG. 9A or the embodiment shown in FIG. 9B may be selected. In the embodiment shown in FIG. 9A, the resistance of the NanoBridge can be larger than that of the NanoBridge shown in FIG. 9B. This may be due to the increase in circumference of the Nano-Bridge ring shown in FIG. 9A that results from its placement around a wider portion of the bead. Resistance is associated with area, as described by:

$$R=\rho L/A$$

Where L equals length, A is the cross sectional area, and ρ is the resistivity of the material. In the case of a Nano-Bridge ring, L equals the circumference of the ring, or $2\pi r$, where r represents the radius of the ring.

Since the ring in FIG. 9A is placed near the widest point of the sphere, the radius of the ring is greater than that of the ring in FIG. 9B, wherein the ring is placed farther from the widest point. Thus, the resistance will be greater for an embodiment similar to that of FIG. 9A. The surface area of the bead coated with DNA close is to the bridge, therefore the "signal" of the NanoBridge ring shown in FIG. 9A may be greater than that of the NanoBridge ring shown in FIG. 9B. There may also be an increase in the thermal noise associated with having an increase in resistance. This relationship between resistance and the associated thermal noise is described by:

$$E_s=\sqrt{4kTRB}$$

Where k represents Boltzmann's constant ($1.374 \times 10^{-23}$ J/° K), T is the absolute temperature (° K), R is the resistance, and B equals the Bandwidth (Hz).

Thus, the circumference and position of the NanoBridge ring structure may be selected so as to optimize the signal to noise ratio. Furthermore, the position of the ring relative to the bead may affect other portions of the process such as, for example, delivery of nucleotides, washing, fabrication, and bead loading. For example, washing may be easier when the bead is in such a position as to have more exposure to the bulk solution, as opposed to being located farther down relative to the solution. In some embodiments, it may be favorable to have the bead in one embodiment versus the other, depending on the desired factors for optimization.

Figure 10:
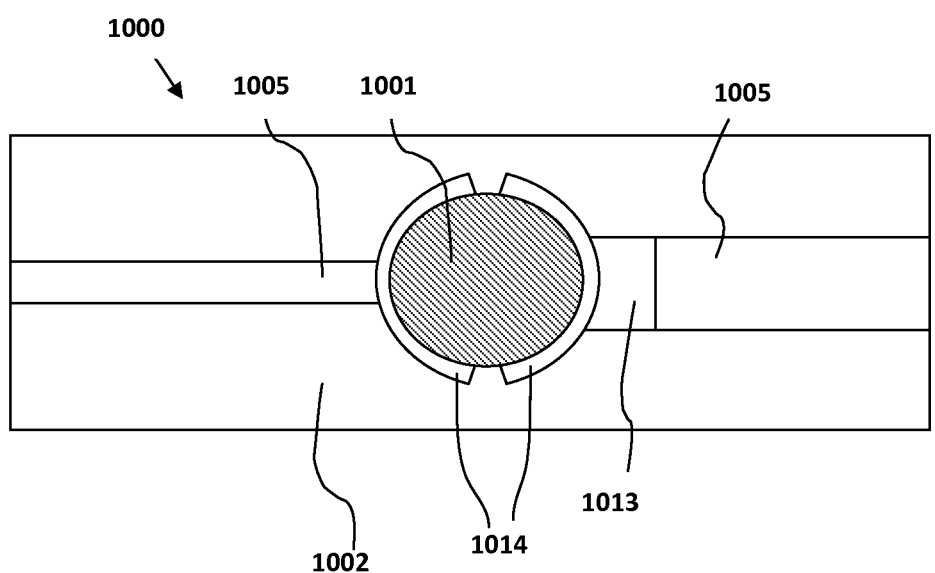
FIG. 10 schematically illustrates an example of a NanoNeedle configured to have a modified ring structure.

Similar considerations may arise with the NanoNeedle embodiment. The placement of the electrodes relative to the bead will impact the amplitude of the output signal and the signal to noise ratio. In some embodiments, the NanoNeedle may also be configured to have a modified ring structure, such as in FIG. 10 where the top view of one embodiment of the bead 1001 on a substrate 1002 is shown. The portions of the electrode prongs 1014 closest to the bead 1001 form a "ring" around bead 1001, but may not be connected. The second electrode prong 1005 may be in contact with a sensor 1013.

In some embodiments of the NanoBridge, the electrical conductors 904 may be connected to heavily doped regions of the NanoBridge (not shown), which then provide electrical connection to the active area 905 of the NanoBridge. Alternatively, the electrical conductors 904 of the Nano-Bridge may be directly connected to the active area 905 of the NanoBridge that have an Ohmic connection by designing the NanoBridge electrical conductors 904 such that the work function matches the work function of the active area 905 of the NanoBridge. For example, the value of the work function of aluminum is close to that of lightly doped silicon, but it is not a perfect match. To create a closer match, an aluminum alloy may alternatively be utilized, or other metals, or polysilicon, etc. In some embodiments, Nano-Bridge may be fabricated from silicon-on-insulator or SOI structure.

Additionally or alternatively, a back gate (not shown) may be utilized in much the same fashion. In a further improvement, the back gate may be segmented, such that there are different sections of the back gate for different areas of a sensor array. There may be many sections, so that it is possible to have an individual back gate for each sensor, permitting compensation for different sequence dependent rates at which the primer is extended.

Figure 11A:
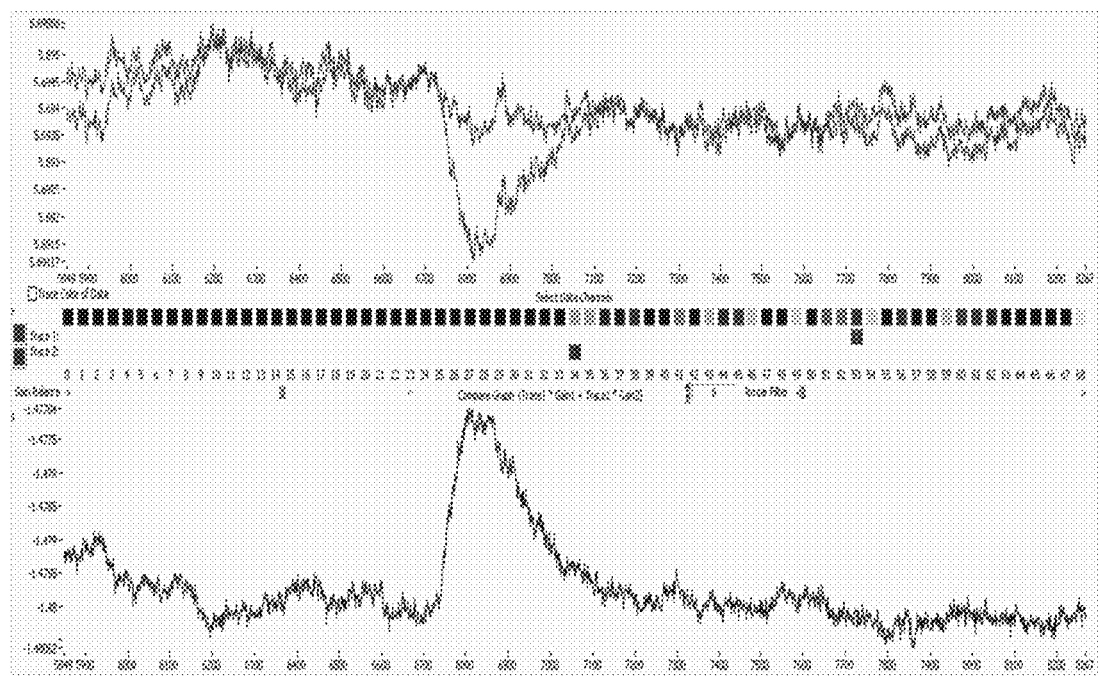
FIGS. 11A and 11B show example data output from NanoBridge sensors for deoxyribonucleic acid (DNA) extension.
Figure 11B:
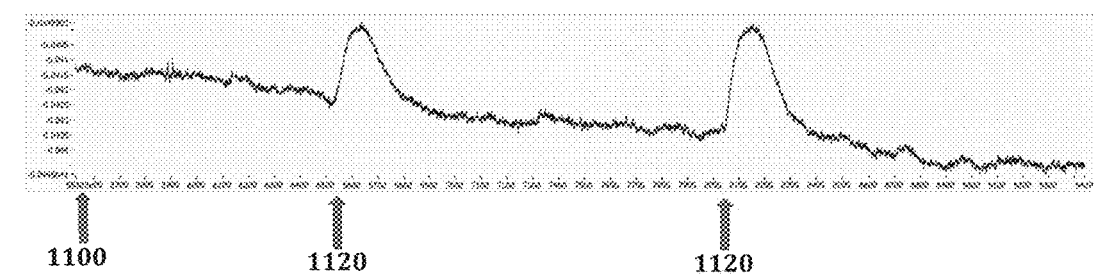

In some embodiments, the NanoBridge sensors are used to detect the incorporation of nucleotides in template DNA for DNA sequencing. FIGS. 11A and 11B show two embodiments of data output from NanoBridge sensors for DNA extension. FIG. 11A shows the extension of DNA by the incorporation of nucleotides and the resultant signal output. The top section of FIG. 11A shows two data outputs from two NanoBridge sensors, where one of the sensors has DNA-coated bead and the other one was used as the reference NanoBridge sensor. The results in top section of FIG. 11A shows the output signal from the NanoBridge with DNA-coated bead has a clear "spike" or "peak" in the current of the NanoBridge, versus the other NanoBridge used as reference here doesn't have the visible "peak" in the current signal. In the bottom section of FIG. 11A the differential measurement of the two output signals of the two sensors in top section of FIG. 11A has been shown, which make the extension signal or "peak" more visible. FIG. 11B indicates the difference seen in the signal output depending on whether the wrong nucleotide is introduced to the system (control) 1100 or the correct nucleotide is incorporated 1120. The incorporation of a correct nucleotide 1120 results in a visible "peak" in the signal, whereas the addition of a wrong nucleotide 1100 in the detection system results in no visible peak. The results were shown for single strand DNA templates with multiple homopolymer sections in the strand attached to the beads. In one embodiment, the direct attachment of oligonucleotides or DNA templates to the Nano-Bridge sensor can be used. In some embodiments, single molecule or polyclonal DNA sequencing can be used. In one embodiment, amplification of the single molecule template can be through "bridge amplification, or "rolling-circle amplification" techniques or other amplification methods.

Electronic sensors, such as NanoBridges, NanoNeedles, ISEFETs, ChemFETs may be designed to have a wide dynamic range, as is the case with some pH sensors. They may alternatively be designed to have a small dynamic range, but high sensitivity. In one embodiment, both the dynamic range of the sensor and the sensitivity of the sensor may be optimized, by including an additional element to the system which biases the active region. The element may be a reference electrode, wherein a variable voltage may be impressed between the reference electrode and the active area of a sensor, such as a NanoBridge or ChemFET.

Adjustment of the voltage can permit highly sensitive detection despite a wide change in the amount of charge interacting with the sensor. For example, a sensor may be optimized to work with a sequencing reaction wherein the target DNA is 100 base pairs long. If the target DNA is changed to being 1000 base pairs long, the sensor may no longer be working within said sensor's dynamic range. The voltage between said reference electrode and the active area may then be adjusted so that the sensor is permitted to work within its dynamic range. If in the course of the sequencing reaction, the extended primer has been extended to 500 base pairs, the sensor may again no longer be within its dynamic range. The reference voltage may again be modified to bring the sensor within its dynamic range. This method can be used as a solution to the potential issue of charge accumulation around the sensor such that the sensor is no longer within its dynamic range. In this manner, the range may be "reset" to a different baseline once the charge concentration is such that it adversely affects the sensitivity of the sensor.

In some embodiments, changing of salt or ionic concentration and/or buffer capacity of the measurement buffer can also be used to adjust the dynamic range of the read out. It can also be used to prevent or reduce the effect of charge crowding where the number of mobile ions or the ionic concentration around, for example, DNA molecules bound to the bead, may be saturated and cause less change in the conductivity or modulation in Debye length due to the nucleotide incorporation. For example, a sensor and buffer and other factors, called "sensing", may be optimized to work with a sequencing reaction wherein the target DNA is 1000 bases long or equivalent charge from the target DNA. If the target DNA is changed to being 1500 bases, for example after the extension of second strand of DNA for 500 bases, the sensing may no longer work within said sensing optimal or dynamic range. The salt or ionic concentration and/or buffer capacity of the measurement buffer may then be adjusted so that the sensing is permitted to work within its optimal or dynamic range. If in the course of the sequencing reaction, the extended primer has been extended to 750 base pairs (total of 1750 base charge of DNA template where one strand is 1000 bases and the second strand that is under extension is 750 bases), the sensing may again no longer be within its optimal or dynamic range. The salt or ionic concentration and/or buffer capacity of the measurement buffer may again be modified to bring the sensing within its dynamic range. This method can be used as a solution to the potential issue of charge accumulation around the sensor such that the sensor is no longer within its dynamic range. In this manner, the range may be "reset" to a different baseline once the charge concentration is such that it adversely affects the sensitivity of the sensing. In some embodiments, the combination of different adjustment for optimal sensing and sensor sensitivity may be used.

In some embodiments, measurements of nucleotide incorporation may be performed during said incorporation in order to determine the sequence of a DNA target. Multiple measurements may be needed in order to ensure that the profile of incorporation is properly captured and measured, for example to determine the number of bases which have been incorporated in a homopolymer run. Such a measurement may measure byproducts of a reaction, such as PPi or hydronium ions or heat. This may be referred as transient signal detection modality. In transient signal detection modality, the detection occurs during or closely after the incorporation or extension event.

Figure 11C:
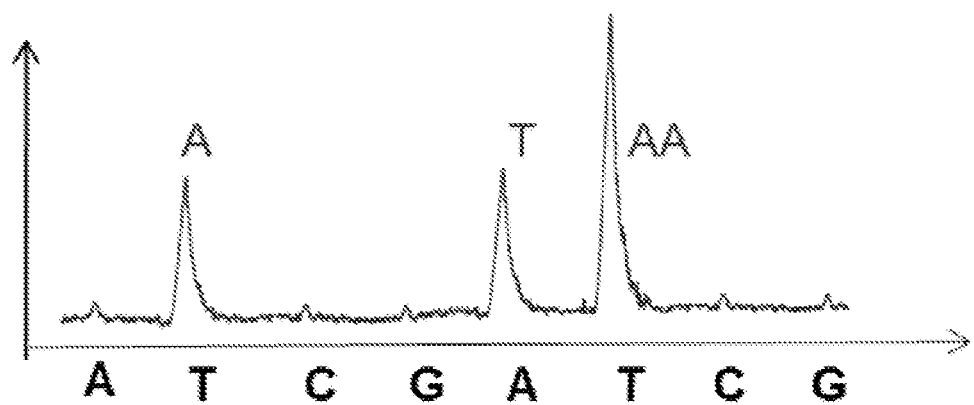
FIG. 11C shows an illustration of transient signal measurement.

An illustration of the transient signal measurement is shown in FIG. 11C. The figure shows how the signal in a transient signal detection modality changes in response to the correct additional of a nucleotide that is subsequently incorporated. In the figure, bases are added in the order "A, T, C, G" (as shown on x-axis of the graph) and there is a visible "peak" each time a base added is the complementary base of the DNA fragment being sequenced. Here, the sequence reads ATAA, with the homopolymer portion "AA" resulting in a signal with a larger peak. For a large array of sensors, such a measurement may require very high data collection rates, which may challenge the sensitivity of the sensor, preventing sufficient signal to noise to provide desired error rates associated with the sequencing data.

Additionally, there may be difficulties associated with trading off the errors associated with phase error, and thus length of read, and the errors associated with accurately measuring which base and how many bases have been incorporated. This may be true as a result of needing a low ionic concentration for optimal sensor accuracy, and a much higher concentration in order for the polymerase to function accurately without phase errors.

Alternatively, two or more different reagent conditions may be utilized wherein at least one set of reagent conditions is utilized for incorporation wherein the reagent conditions may be optimized for polymerase accuracy and minimization of dephasing and a second reagent may be utilized wherein the accuracy of the sensor is optimized, for example by the utilization of a buffer of very low ionic strength. Reading the sensor separately from the incorporation event may improve the sequencing data accuracy and read length. This may be referred to as steady state detection. In steady state detection, reading of the sensors occurs after the "completion" of the incorporation event. For example, if one type of nucleotide is delivered to the DNA template, the detection is based on the signal measurement at a point in time when there has been sufficient time for the incorporation event to occur.

The steady state change may remain until a change in the environment around the DNA template, for example, the next cycle of nucleotide or buffer delivery. For example, steady state change in impedance around the bead may be due to change of charge of DNA template after nucleotide incorporation, or the change in concentration of counter mobile ions around the fixed DNA templates due to the change of DNA charge, for instance, after nucleotide incorporation and/or addition of a negatively charged base, A significant issue associated with next generation sequencing and various detection methods is the enormous quantity of data generated. Some systems can generate an average of 3000 or more data points for each useful base of sequencing data. Storing and analyzing data adds significantly to the overall cost of next generation sequencing. In some embodiments, data reduction is performed in the simplest way, by acquiring less data. Polymerase activity can be significantly more rapid than the time needed to bring reagents with dNTPs completely through a flow cell (the microfluidic structures with a nanosensor array); thus DNA colonies close to the inlet of a flow cell may have completely finished the next synthesis before the dNTPs have even reached the colonies near the outlet of said flow cell. If data is acquired for the entire flow cell during the time needed to detect reactions occurring anywhere in the flow cell, much of the data will be from regions of the flow cell where no reaction is occurring. Depending on the time needed for the dNTP reagent slug to traverse the flow cell, and the speed of polymerization, most of the colonies in the flow cell will be either waiting for dNTPs, or will have completed their synthesis reaction, rather than incorporating dNTPs and thus producing useful data.

Figure 12A:
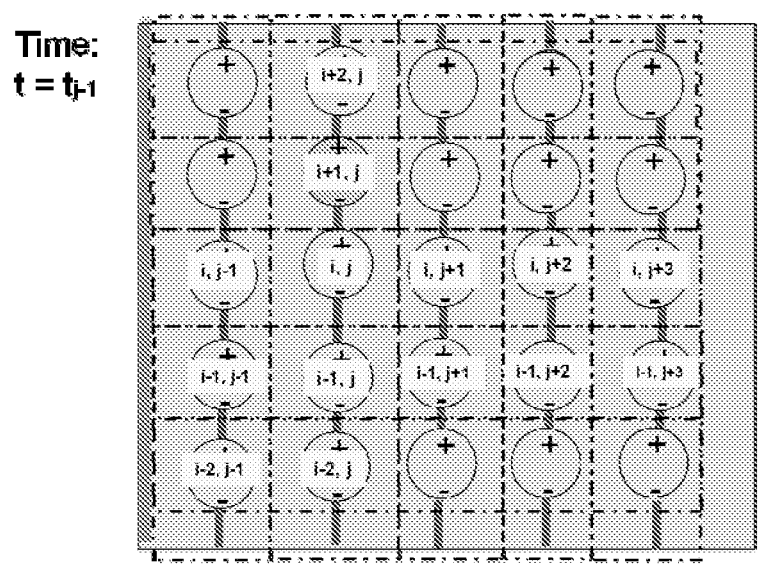
FIG. 12A schematically illustrates detector electronics that may be synchronized with the movement of a reagent slug.

In some embodiments, the readout of the detector electronics is synchronized with the movement of the reagent slug through the flow cell. A reagent slug containing dNTPs may initially enter the flow cell, but not yet move far enough into the flow cell for the dNTPs to bind and incorporate with any of the colonies, as shown in FIG. 12A. At this point in time it may be possible to not take data at all. At a point slightly later in time the reagent slug will have entered the flow cell sufficiently to interact with the set of colonies in the first region, as shown in FIG. 12B. At this point in time data may be taken from the detectors associated with the colonies in a first region, but may be not taken for other regions of the flow cell. At a second point later in time the reagent slug may have entered the flow cell sufficiently to begin to interact with the set of colonies in a second region, as illustrated by FIG. 12C. At this point in time data may be taken from the detectors associated with the colonies in the second region, and may likely need to still be taken from the first region, depending on the speed of the reagent slug and the speed of the polymerase, but may not need to be taken for other regions of the flow cell. At a third point later in time the reagent slug has traversed through the flow cell sufficiently to begin to interact with the last set of colonies in the flow cell, as shown in FIG. 12D. At this point in time data may be taken from the detectors associated with the colonies in the last region. Some data may still need to be taken from previous regions, such as regions immediately preceding said last set of colonies depending on the speed of the reagent slug, the speed of the polymerase, the length of the flow cells, and the size of the colonies, but may not need to be taken for other regions of the flow cell.

In some embodiments, one or more different types of differential measurements may be taken in order to account for noise that can be generated due to factors such as, for example, buffers, temperature, fluid flow, solution, carriers, dNTP misincorporation, sensor electronics, etc. These differential measurements can help calibrate the system or may be used as part of post-processing in order to help minimize noise and improve the accuracy of the system.

Figure 12F:
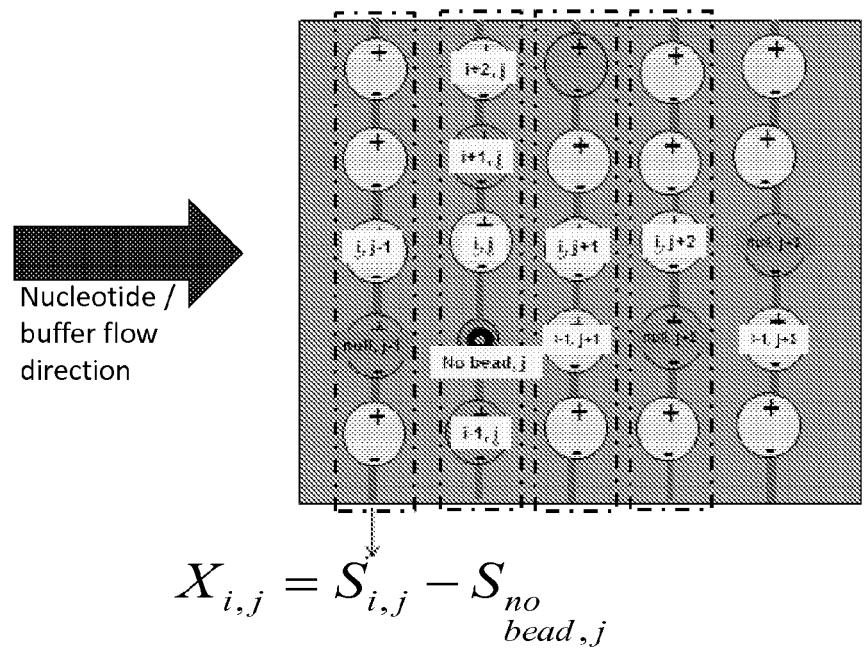
FIG. 12F schematically illustrates differential measurements using an empty sensor as a reference.

As shown in FIG. 12E, in some embodiments, null beads may be used as references for differential measurements; such references may compensate for variations in temperature, variations in the conductivity or pH of the bulk reagent, localized variations in conductivity or pH, or other variations. The control of the system will help limit and identify phase errors, thereby extending read length. In some embodiments, as shown in FIG. 12F, the differential measurement is performed by using an empty sensor (no bead) as a reference. Although FIGS. 12E and F use a differential measurement from column "j−1" and "j", respectively, as an example, the differential measurement may be taken from any row or column or array.

Figure 12G:
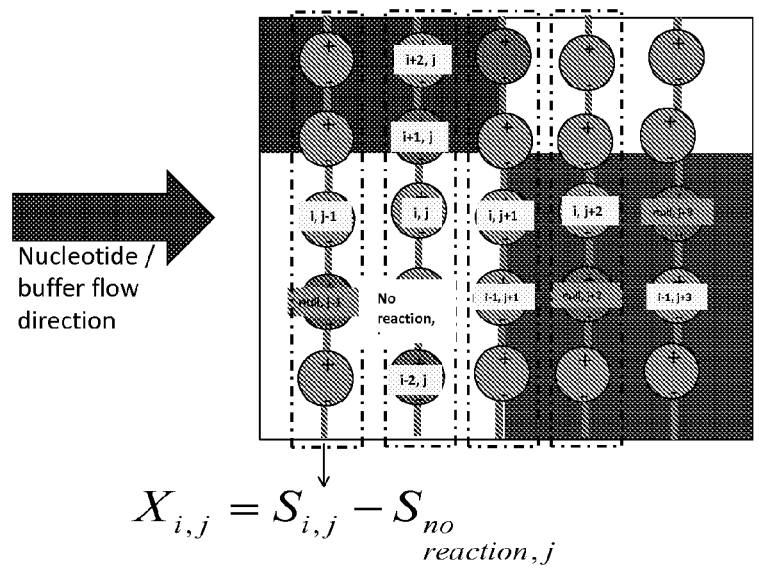
FIG. 12G schematically illustrates beads or sensor regions without an incorporation reaction that may be used as references.

In another embodiment, as illustrated in FIG. 12G, beads or sensor regions without an incorporation reaction may provide better references relative to empty sensors or null beads. This may be because as DNA polymerase and beads will be present in the volume of interest, any variation in surface chemistry and resulting background counter ion concentration will likely be better matched. At each cycle of nucleotide injection only about ¼ of the beads have the DNA strands and complimentary bases required for incorporation at that cycle and the rest of the beads do not. This differential measurement allows for the removal of common noise and variation. Although FIG. 12G uses a "no reaction" bead from column "j" as an example, any other bead or beads (or sensor/sensors) from any row or column or array may be used.

It is likely that different colonies on beads or sensor regions may have colony DNA and/or extended primers of different lengths from the lengths of colony DNA and/or extended primers associated with other beads and/or sensor regions, and thus may have different amounts of charge present that may interact with the sensor. Thus their charge/ signal is not the same, but differential measurements may allow for averaging over the array of sensors such that these values are normalized and common noise may be removed.

In another embodiment, the differential sensor is not exposed to the solution, but may be covered by a dielectric layer. In this manner, the differential sensor is compared to a sensor that may be detecting a target reaction, such as DNA sequencing, associated with the bead. This method may allow for the removal of noise associated with the electronics of the sensor and read out circuitry, since the differential sensor is not exposed to the solution.

Figure 12H:
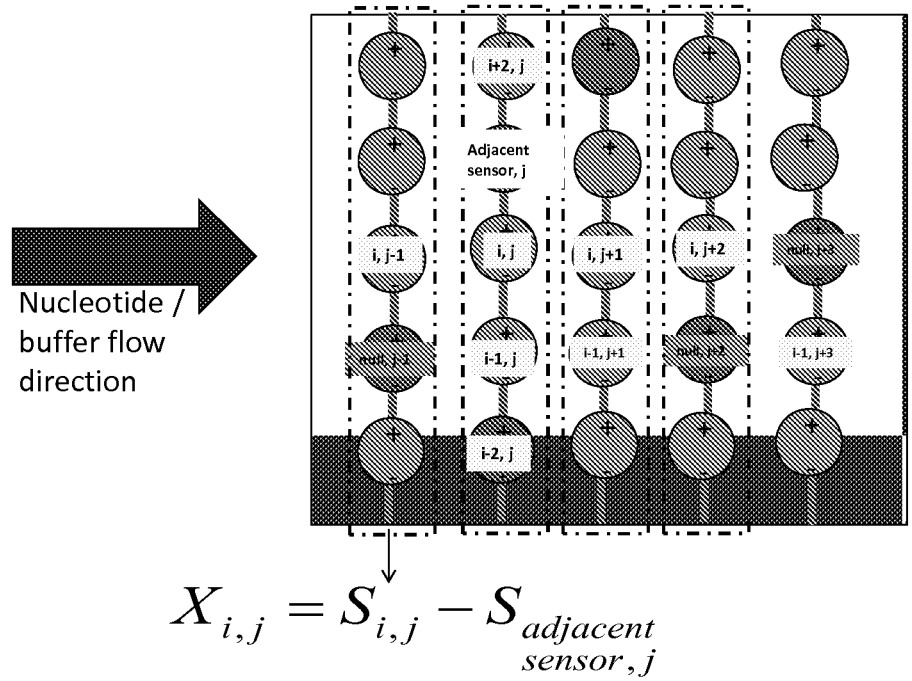
FIG. 12H schematically illustrates adjacent detectors that may be used as reference channels.

In some embodiments, a reference electrode may be used for electronic or pH sensors, for example FET pH sensors; some designs for arrays of FET pH sensors use a reference channel for each detection channel; others have reference channels for a set of detection channels. But the local pH of the detector is influenced by the presence of the DNA colony, and changes as the length of the second strand of DNA is extended by the polymerization reaction. In using a chemistry whereby a single type of nucleotide is introduced to the flow cell at a time, many detector channels will not have a reaction taking place at that detector; in fact most detector channels will not have a reaction occurring. Thus in one embodiment, as shown in FIG. 12H, neighboring/ adjacent detectors are used as reference channels, providing the data analysis algorithms an opportunity to measure the pH or ion concentration as it changes in detectors which are neighboring detectors to a detector which has a polymerization reaction occurring. Although FIG. 12H uses an adjacent bead sensor from column "j" as an example, any other sensor or sensors from any neighboring row or column may be used. Although a neighbor bead from column This permits detection of change, for example, pH or ion concentration levels, or other sources of noise local to the detector of interest, and may also permit detection of crosstalk, allowing for monitoring and modification of a crosstalk deconvolution function.

Figure 12I:
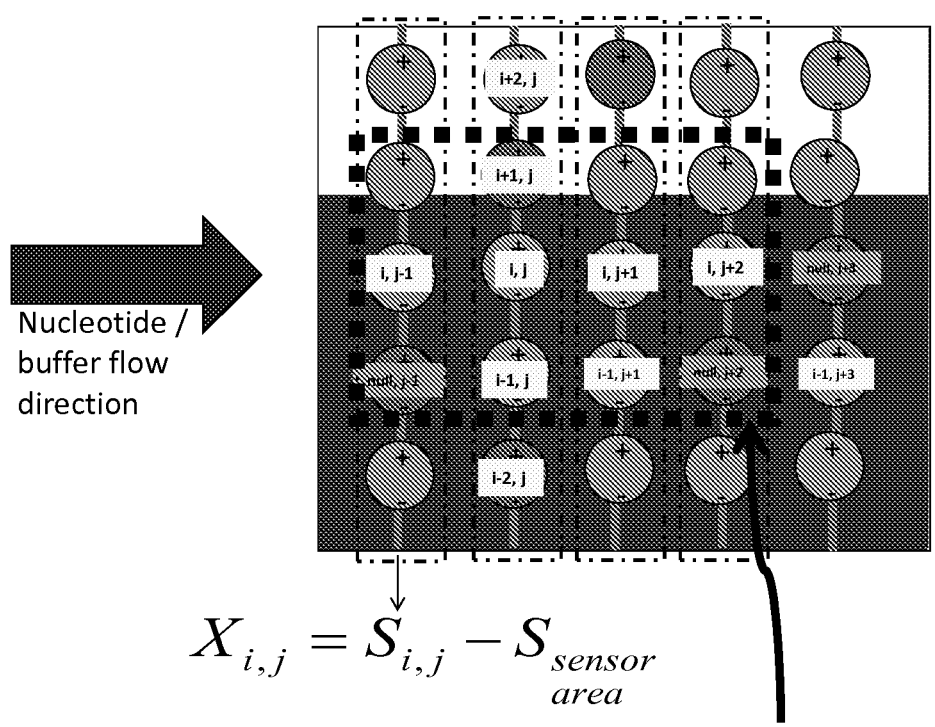
FIG. 12I schematically illustrates a sensor area that may be used as a reference.

In a further embodiment, as shown in FIG. 12I, sensor area 1220, may be used as a reference. This reference sensor region may be null (does not have associated colonies, either with or without bead or DNA), or may simply be used to generate an average signal, or some combination of both methods. In some embodiments, the differential measurement is taken by calculating the average output data associated with a selected area that contains a plurality of sensors with associated carriers. This type of differential measurement may be characterized as a "blind", averaging type of measurement because some carriers, such as a magnetic bead for DNA sequencing, may be undergoing a reaction and other beads may be null beads. This differential measurement that takes an average measurement of beads in a neighboring area allows for the removal of common noise, such as for example solution, buffer, reagents, etc. The area 1220 can consist of any number of sensors, including single neighboring sensors, columns of sensors, rows of sensors, or any shape or size of a sensor array of a nanosensor array.

In another embodiment, the differential measurement may be achieved by averaging the data output from a specific column of sensors and associated carriers in a nanosensor array. This type of differential measurement may allow for consideration of the time factor associated with the delivery of solution and reagents to the pixels of the nano-array, as shown in FIGS. 12A-D.

Since the delivery of the solution may occur at different times for different columns of the nano-array, taking a differential measurement based on columns allows for calibration that is time based. There is a continuous flow of reaction buffers contained dNTPs over the detector array. As soon as the flow passes over the colony, the incorporation process starts which lead to change in the buffer conductivity. In the transient condition, this change can be captured based on the change in local pH or conductivity around the colony. Therefore, as reagent slug goes over the colony, the data collection is performed. After the reaction time, the data collection can be performed to capture the local conductivity change to detect the incorporation.

These measurements may also be performed in the steady state condition. First, the reaction buffer contained dNTPs may be flowed over the colonies. The incorporation may occur on some of the colonies and this can change the conductivity around the colony. Subsequently, measurement buffer with lower conductivity may be flowed over the colonies. As a result of incorporation, the conductivity may increase closer to the colony and this change in conductivity can be detected by the sensor. The flow of reagents over the colonies and change in the conductivity may occur very quickly. The data collection, therefore, can be synchronized with the flow of the measurement buffer. When the buffer slug passes each column, the data collection may be performed. In this steady state detection method, data collection can be done at any time. In some embodiments, the measurement buffer and the reaction buffer are the same buffer and the detection occurs by measurement of conductivity change after the incorporation event.

Figure 12J:
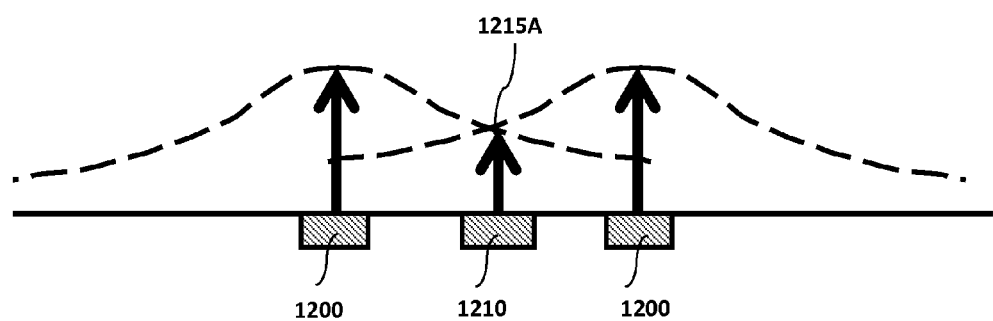
FIG. 12J schematically illustrates sensors with a reaction occurring that may be in close proximity to a sensor without a reaction occurring.
Figure 12K:
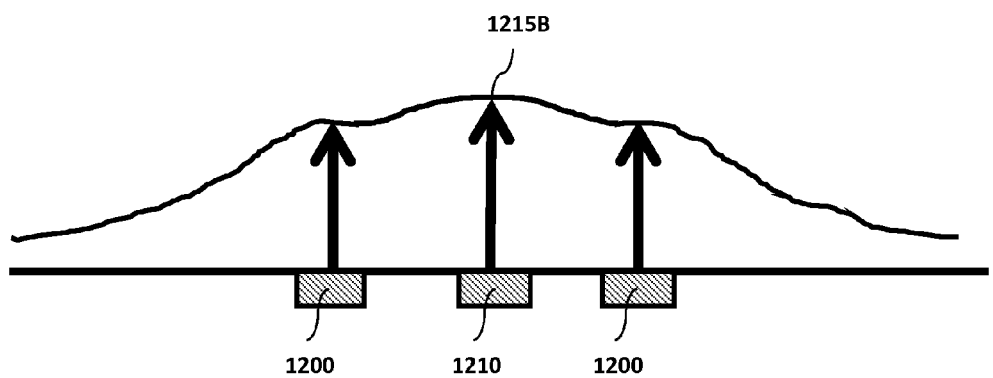
FIG. 12K schematically illustrates an example of an output data signal with a false positive signal.

FIG. 12J illustrates, in some embodiments, sensors with a reaction occurring 1200 that are in close proximity to a sensor without a reaction occurring 1210. The figures illustrate that the locations of sensors 1200 in relation to sensor 1210 may result in crosstalk between the sensors, as shown by overlapping signal region 1215A. FIG. 12K shows one embodiment of an output data signal that shows a "false positive signal" 1215B for sensor 1210 that does not actually have a reaction occurring. This is due to the crosstalk between the sensors 1200 and sensor 1210. In one embodiment, this false positive signal, for example, may be a false dNTP incorporation signal for DNA sequencing. Sensors do not have to be adjacent to each other to generate false positive signals, cross-talk can occur for a variety of distances between sensors. Differential measurement methods, such as for example a cross-talk deconvolution function matrix, can be used to remove false positive signals from the output data signal either through calibration of the array or through post-processing.

In one embodiment, as shown in FIG. 12L, differential measurements can be taken by using a cross-talk deconvolution function matrix. An area of interest may be selected wherein one pixel is undergoing a reaction and the other pixels in the area (n×n) are null. In this manner, the effect on the other pixels in the area can be measured, and this may allow for quantification of the amount of crosstalk from one pixel to the rest. This process can be repeated for the rest of the pixels until an n×n data matrix is generated wherein crosstalk among all the pixels in the area can be determined. This cross-talk deconvolution function matrix can be taken out of the raw output signal from the nanosensor array after a reaction of interest, such as for example DNA sequencing, is completed. In this manner, crosstalk among the sensors of the nano-array may be accounted for and removed from the raw data in order to help generate more accurate results.

In some embodiments, a differential measurement may be used to account for polymerase misincorporation of nucleotides for reactions such as DNA sequencing. A known oligonucleotide or DNA fragment attached or annealed to the DNA template can be used. "Wrong" nucleotides may be used in order to find out how much the output signal is from "misincorporation". In some embodiments, unincorporable nucleotides or nucleotide analogs may be used in order to find out the rate and how much of the output signal results from misincorporation. This data may be used to optimize and process output data such that the final signal is from correct incorporations.

Figure 12M:
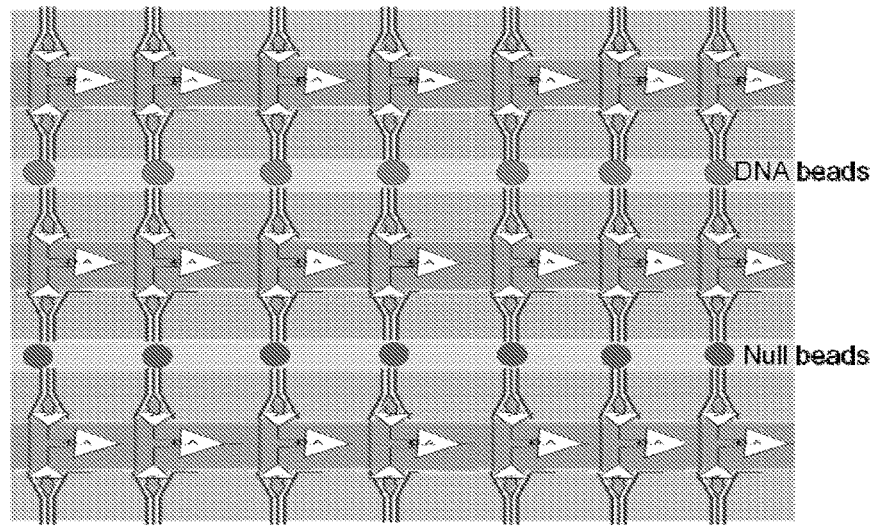
FIG. 12M schematically illustrates pair wise introduction of null bead or beads with different sequences in conjunction with sample beads.
Figure 12N:
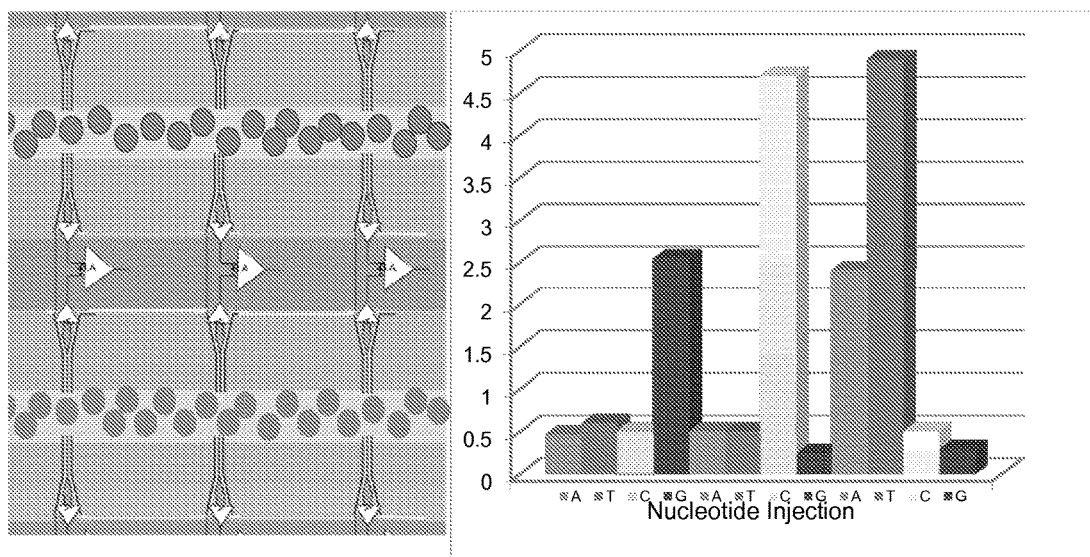
FIG. 12N shows an example of results from DNA extension measured by a NanoNeedle sensor.

In another embodiment, as shown in FIG. 12M, null beads or beads with different sequences are introduced pair wise with sample beads, and the signals are determined using a differential amplifier, obviating the need for the analysis algorithms to directly deconvolve variations in background and crosstalk, as shown in FIG. 12N. Nanoneedle sensor can be used for either of steady state or transient signal detection modalities. FIG. 12N data shows the experimental results from DNA extension measured by a NanoNeedle sensor.

Using various types of differential measurements may help generate more accurate data signals.

Figure 13B:
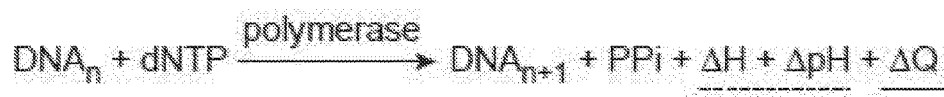
FIG. 13B illustrates an example chemical reaction of nucleotide incorporation for DNA sequencing.

In some embodiments, a method for improving signal output is through use of the steady state detection method. In some embodiments, the chemical reaction of interest is nucleotide incorporation for DNA sequencing, and this is the chemical reaction being detected by the steady state detection method as shown in FIG. 13B. The nucleotide incorporation reaction of FIG. 13B illustrates that the steady-state detection method may be used to directly detect a change in the environment around the reaction, such as for example a change in charge (Q) or impedance that results from nucleotide incorporation. Steady state measurements may provide several advantages over the transient detection modality. The sensor can be utilized in a manner whereby less data is required as the sensor may no longer be forced to be read at a high data rate to keep up with the polymerase incorporation, but can instead be read a single time, or time averaging interval, wherein the electronics may have time constants that are sufficiently long to permit the sensor noise to be significantly reduced. Thus, the data collection may be much simpler.

Figure 14:
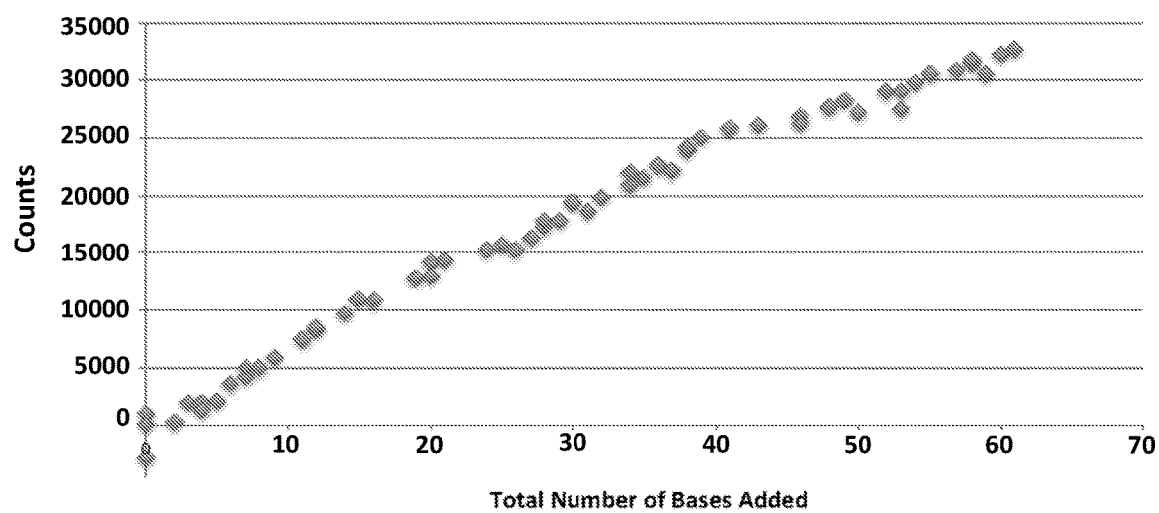
FIG. 14 shows an example of signal generated in a steady state detection mode.

FIG. 14 shows an exemplary embodiment of the signal generated in steady state detection mode. The figure illustrates that signal is linear, even beyond the addition of 60 base pairs. This raw data shows that the steady state detection method can effectively be used for base pair reads over at least 60 base pairs. Other data shows that the steady state detection can effectively be used for base pair reads over 80 base pairs, 200 base pairs, 500 base pairs, 1000 base pairs or longer.

Figure 15:
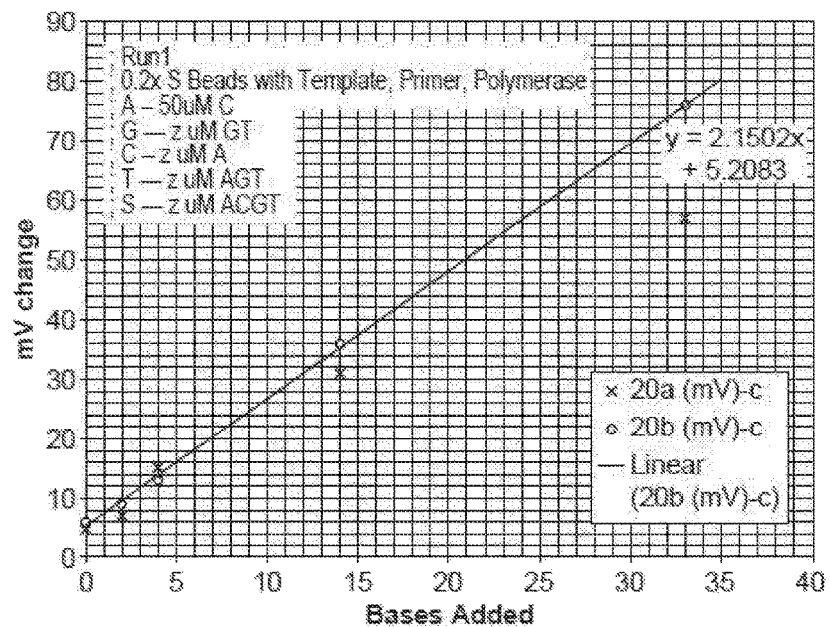
FIG. 15 shows an example of raw data from a linear homopolymer read.

FIG. 15 shows another embodiment of raw unprocessed data from a linear homopolymer read with a non-linearity of less than 0.5 base for 2, 4, 14 and 33 base sections. Here, the data is displayed based on the number of bases incorporated per cycle and there is also a near linear relationship between conductivity and base pair addition. This raw data has only been corrected for a control sensor without bead.

As stated previously, the steady state measurement approach may have advantages over transient detection. The signal is steady and thus the electronics can utilize signal averaging without distorting or processing the signal profile. In some embodiments, since the charge being detected is bound to the bead, the detection can occur separately from the incorporation event. This may allow the incorporation solution to be optimized for incorporation and the read solution to be optimized for reading. The charge may not diffuse and thus crosstalk between sensors can be minimized or eliminated, reducing a source of error and a computational burden. To capture the transient signal, data collection must capture many data point on all sensors during the dNTP addition. The data must be curve-fit and adjusted for time delays.

Detection during the incorporation time period may create several challenges. The buffer conditions must be a compromise between having low enough salt, buffering, and dNTP concentrations to allow for sufficiently sensitive detection, and having high enough concentration to allow for complete and accurate incorporation events. In contrast, the steady state measurement method, in some embodiments, may utilize two buffers conditions, each one optimized for a single task, one for incorporation chemistry, and one for detection. Further, the incorporation chemistry can permit much more accurate incorporation and less dephasing as a result of utilizing natural bases in a competitive reaction using one base and three ribonucleotides or other non-incorporable nucleotides.

The bioinformatics challenges can be significantly simpler for steady state measurements for a number of reasons. There may effectively be no cross talk between channels as a result of diffusion, as the counter-ions that are measured are directly associated with the DNA. The amount of data can be significantly lower, as it may not be necessary to monitor constantly to keep from missing a potential incorporation event, which may happen at different times in different locations in the flow cell, even within a single column, as the flow rate through a flow cell may be very non-uniform. The number of data points could be as few as one, possibly two data points per fluidics cycle. Homopolymer accuracy and linearity is likely to be much better.

Figure 16:
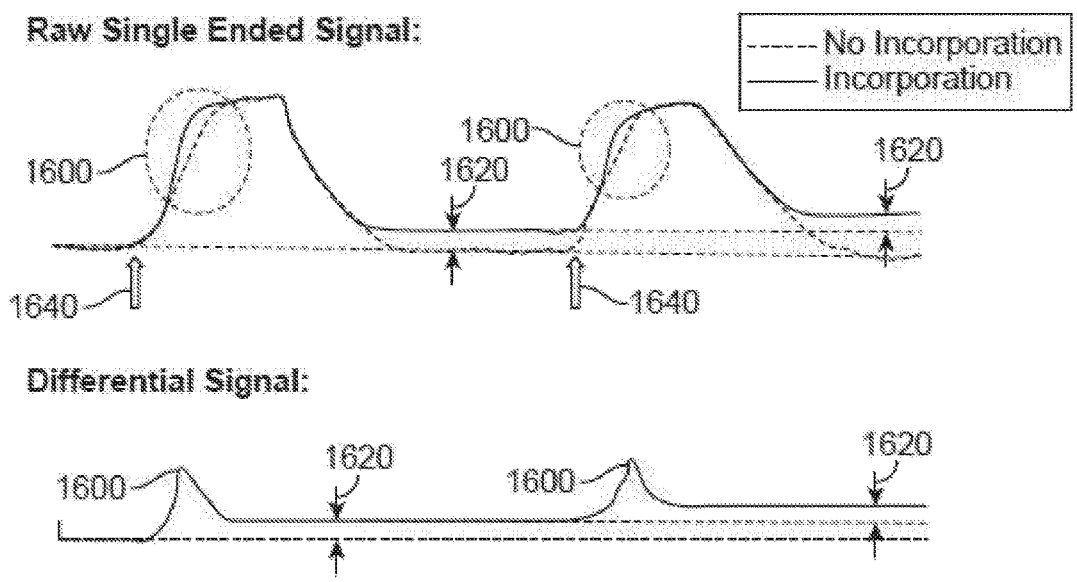
FIG. 16 shows an example comparison of signals generated during transient versus steady state detection.

In one embodiment, a comparison of the signals generated during transient versus steady state detection is shown in FIG. 16. As illustrated by the figure, wherein the incorporation of nucleotides 1640 is being detected, steady state detection 1620 may be a simpler method than transient detection 1600 because it may require a simpler extraction and calculation of the differential signal from the raw signal and, as mentioned previously, steady state detection is not as time sensitive as transient signal detection and it may result in higher linearity and accuracy in sequencing and homopolymer detection.

Figure 17:
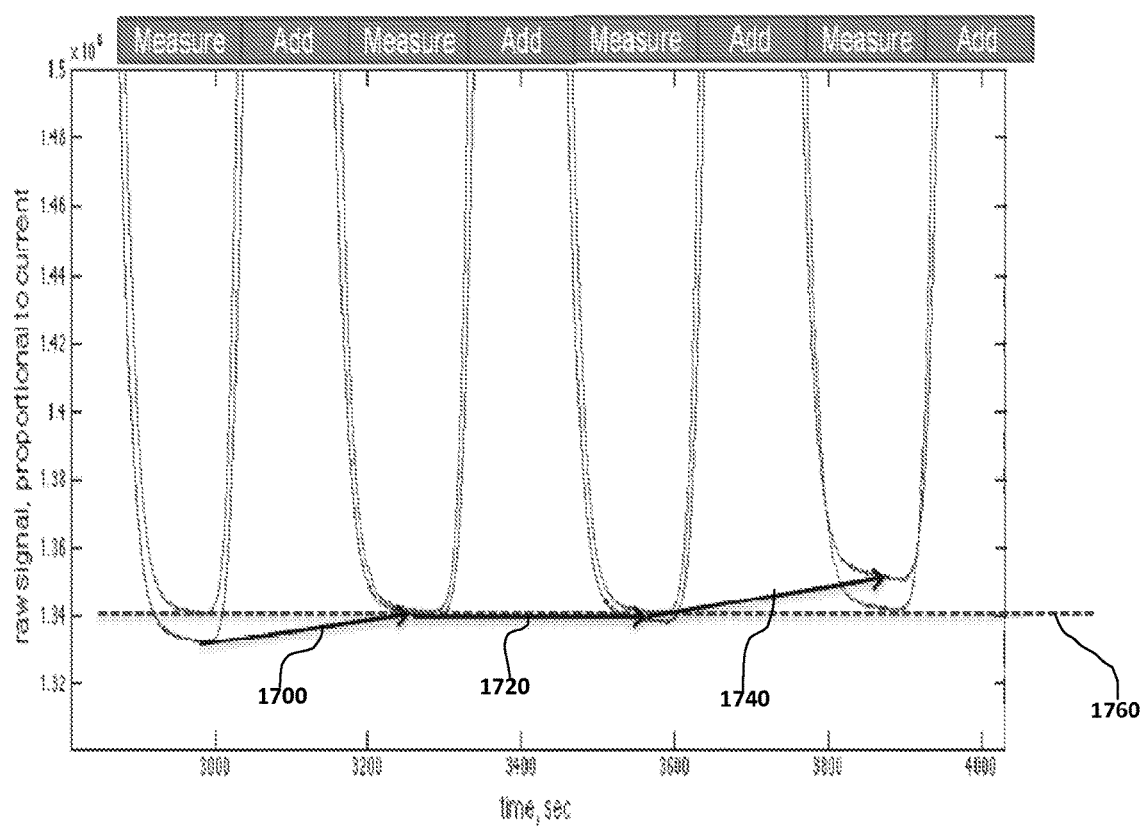
FIG. 17 shows an example of raw data generated during steady state detection by NanoNeedle sensors.

An exemplary embodiment of the experimental raw data generated during steady state detection by NanoNeedle sensors is shown in FIG. 17, which illustrates the difference in signal output for the detection after incorporation of three bases 1700, zero bases 1720, and five bases 1740. The point at the beginning of each arrow corresponds with the end of a wash step for the incorporation buffer, wherein there are two different buffers used, one for incorporation and one for detection. In some embodiments, a customized buffer system may be used with different formulations for incorporation and detection, allowing for decoupled optimization. The zero base incorporation 1720 results in a flat signal, with no change, whereas the addition of three or five bases (1720 and 1740, respectively) results in a change in the level of the signal, proportional to the number of bases being detected, A flat signal 1760 from a reference sensor is also shown, for comparison.

Figure 18B:
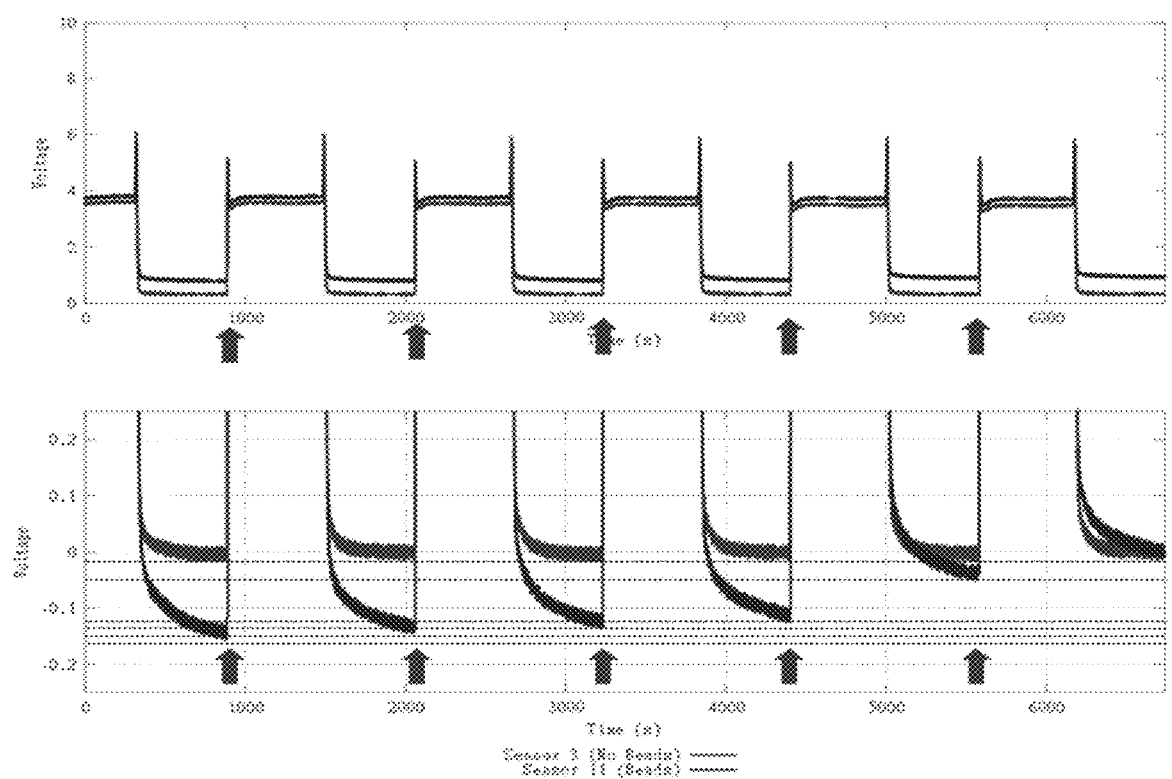

FIGS. 18A and 18B further illustrate example embodiments of raw data output for DNA sequencing based on a steady state detection method, For both figures, the raw data is shown in the top graph, and the bottom graph shows the same data, auto zeroed and magnified. The incorporation of a correct nucleotide is shown by the arrows and the bottom of each signal rises as more bases are correctly incorporated.

Figure 19A:
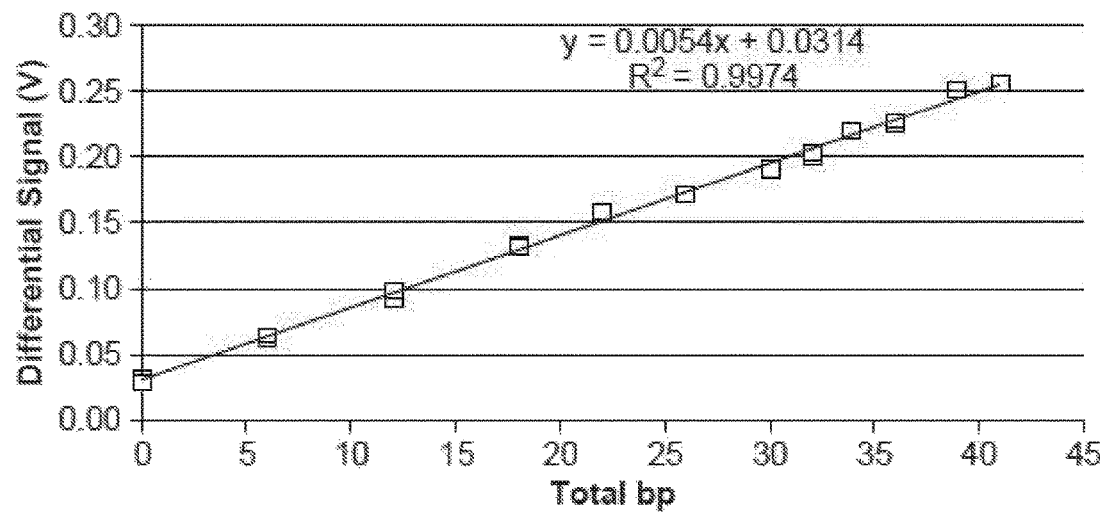
FIG. 19A shows example results of homopolymer reads in DNA sequencing with a NanoNeedle sensor.

The transient profile may be different for homopolymer additions, whereas the steady state can show a linear response, so there may be a reason that the homopolymer error rate could be reduced. FIG. 19A shows the results of homopolymer reads in DNA sequencing with the NanoNeedle sensor where there is an increase in the differential signal each time there is a correct incorporation of a nucleotide (an incorrect base pair results in a data point that stays at approximately the same height on the graph as the previous data point). The differential signal shows that the conductivity has a near linear relationship with base pair additions. The differential signal shows a 5.4 mV change per base addition during DNA extension. The homopolymer template after primer was: 3'- AAA AAA CCC CCC TTT TTT AAA ATT TTC CCC AAC CAA CCC AAC TCA GTC GTC AAT CAC CAG A-5' (SEQ ID NO: 1).

Figure 19B:
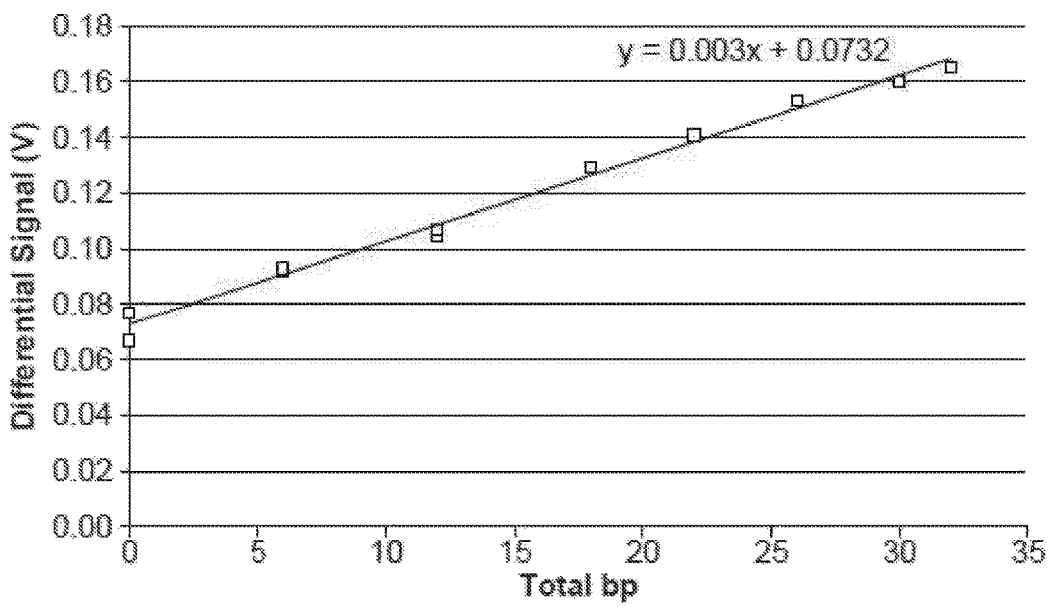
FIG. 19B shows example raw unprocessed data from a homopolymer run.
Figure 19C:
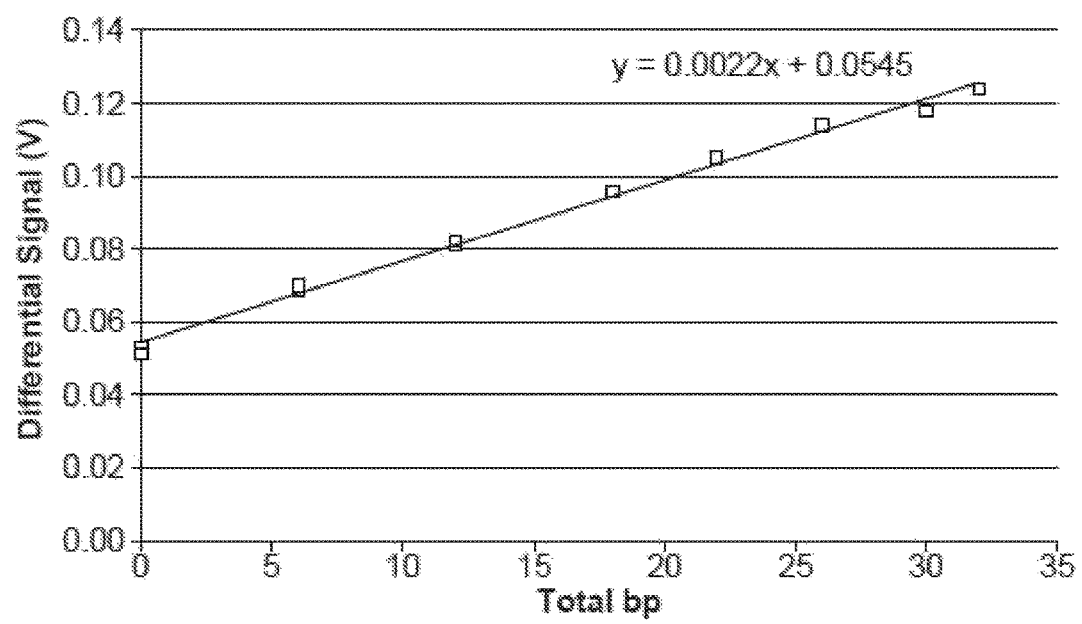
FIG. 19C shows an example repeat run of the hompolymer run of FIG. 19B.

FIGS. 19B and 19C show another embodiment of raw unprocessed data from a homopolymer run, wherein FIG. 19C is a repeat run of the homopolymer run of FIG. 19B with a different nanosensor. The template being sequencing in FIG. 19B is: A AAA AAC CCC CCT TTT TTA AAA TTT TCC CCA A (SEQ ID NO: 2).

Figure 20:
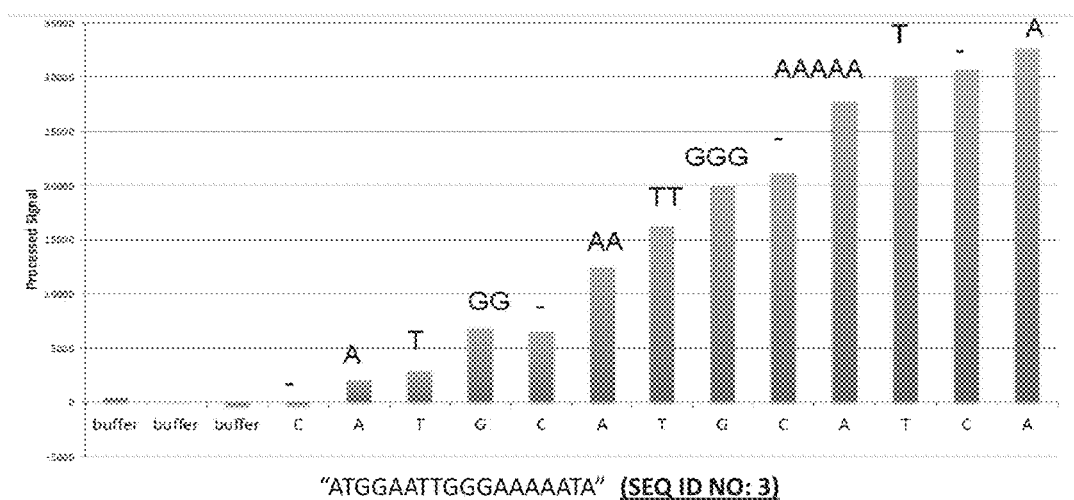
FIG. 20 shows example results of a sequencing experiment.

In a further embodiment, in an exemplary sequencing experiment, the order of the nucleotides being injected into the sequencing module is "C, A, T, G" and the results of the sequencing data indicate that nucleotides being incorporated are "ATGGAATTGGGAAAAATA" (SEQ ID NO: 3), as shown in FIG. 20, which matches with the sequence of used DNA template in the experiment.

In one embodiment, the effective read length may be increased by performing a sequencing reaction to the full length possible while utilizing said low ionic concentrations, melting off the extended primer strand, introducing new primers and dNTPs, and proceeding with the synthesis reaction while using optimal ion concentrations for synthesis, for a number of bases that may be statistically less likely than the number of bases that have been previously sequenced, followed by changing the conditions to those appropriate for detection. Said process of melting off the extended primer strand, introducing new primers and dNTPs, and proceeding with the synthesis reaction while using optimal ion concentrations for synthesis, for a number of bases which may be statistically likely to be less than the number of bases that have been previously sequenced, followed by changing the conditions to those appropriate for detection may be repeated multiple times, until the process no longer results in useful data. As the determination of how many synthesis steps to utilize is statistical, the process may be reversed, performing a synthesis with conditions optimal for synthesis, followed by performing synthesis utilizing conditions appropriate for detection. This may then be followed by melting off the extended primer strands, introducing new primers, and utilizing ionic concentrations appropriate for detection.

Figure 21:
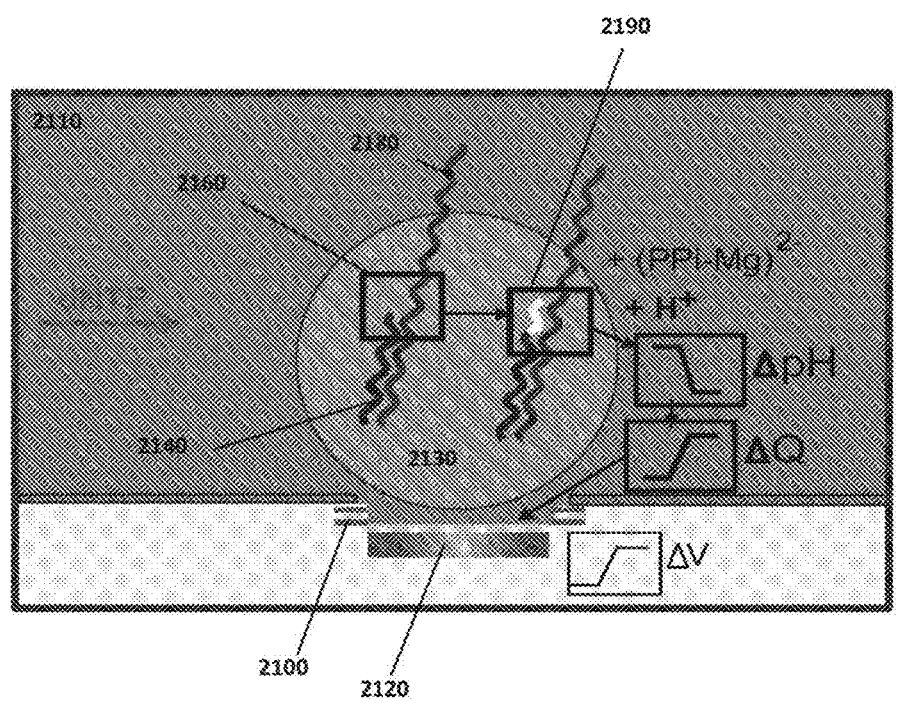
FIG. 21 schematically illustrates an example of using NanoNeedle and NanoBridge sensors in conjunction with each other on the same nano-senor array.

In a further embodiment, both the NanoNeedle and the NanoBridge sensors may be used in the same pixel, as shown in FIG. 21. In one embodiment the bead may be held on a flat or nearly flat surface. In some embodiments, the bead may be located on a depression. The NanoNeedle sensor 2100 can be optimized for steady state detection and the NanoBridge sensor 2120 can be optimized for transient signal detection. As the figure illustrates, in one embodiment, the two sensors may be proximal to a bead 2130 wherein there is template DNA 2180 attached to the bead. dNTPs and other reagents can be delivered via bulk solution 2110, such as DNA primer 2140. In some embodiments, hybridization 2160 between the DNA primer 2140 and template DNA 2180 may occur. Then, nucleotide incorporation and DNA extension 2190 may occur. The incorporation of nucleotides can lead to one or more of a change in pH, generation of H+ ions, generation of pyrophosphate (PPi), and a change in impedance (Z), and/or charge (Q), and/or conductance (Y). One or more of these changes can be detected by NanoNeedle sensor 2100 and NanoBridge sensor 2120. The output signal may be represented as a change in voltage (V) or change in current (I). Two sensors can permit detection based on complementary detection modalities (both steady state and transient signal detection), may allow for independent signal confirmation, can increase read accuracy, and may increase signal to noise ratio. Two sensors can permit detection based on two orthogonal or independent read outs. In some embodiments, one or more sensors can be used for detection at different operating conditions, such as different frequencies, to provide different, orthogonal, and/or independent read out signals. For example, NanoNeedle can be used at different frequencies to measure different impedance conditions, for example, at one frequency measuring mostly conductance modulation, while in another frequency detecting capacitive changes due or after the nucleotide incorporation.

In some embodiments, an integrator may be incorporated with the sensor in order to maximize the amount of time given to each sensor and in order to reduce the read noise of each sensor. The integrator may include a capacitor associated with each sensor in the array. In other embodiments, the sensor may be configured as a capacitive sensor, where there is no current flow, but rather an accumulation of charge during a chemistry cycle. In some embodiments, utilizing either an integrating device or a capacitive device, the sensor may have local amplification electronics for each pixel.

Figure 22A:
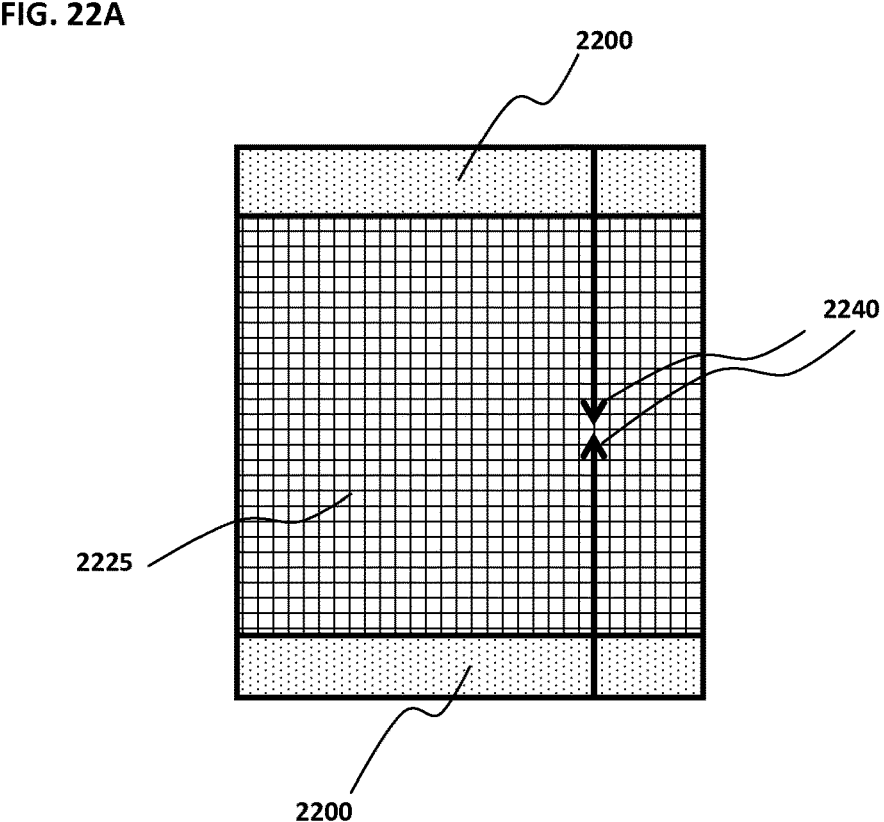
FIG. 22A schematically illustrates an example of a device with readout ports on opposite sides.
Figure 22B:
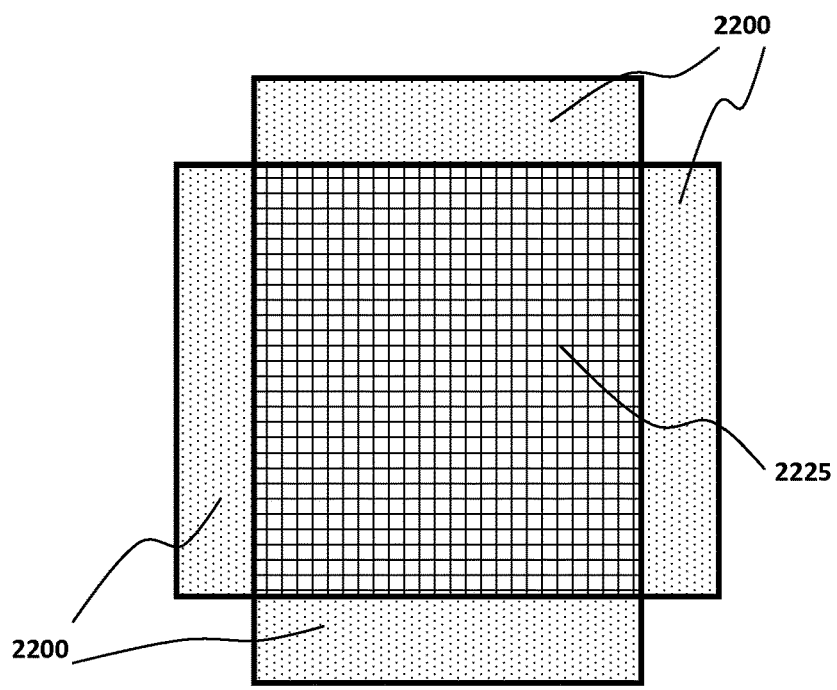
FIG. 22B schematically illustrates an example of a device with readout ports along four sides.

In other embodiments, the charge or signal may be moved, in a manner similar to that of a CCD to a readout port. There may be one or more readout ports associated with each microfluidic device, said device containing a nanosensor array. In some embodiments, the circuitry at the readout ports may include one or more of an analog to digital converter, a row selector, a column selector, shift register, serial read out, multiplexer, etc. In one embodiment, as shown in FIG. 22A, there may be readout ports 2200 on opposite sides of the device 2225. This figure illustrates that the sampling rate may be reduced and the integration time may be increased by using more than one readout port. Arrows 2240 represent the distance covered by the readout ports 2200 on opposite sides of device 2225. Since there are two readout ports, the amount of data from the device that must be sampled is halved for each chip and the integration time is doubled. Reducing the amount of data and the rate of sampling for each readout port may enhance signal quality and increase the signal to noise ratio. In some embodiments, each corner of the device may have a readout port; in other embodiments, there may be ports along all four sides of the chip, as shown in FIG. 22B, allowing for a reduced readout rate and an associated improved signal to noise ratio. It can be also allocated in the middle sections of the chip or a combination of these.

Figure 23:
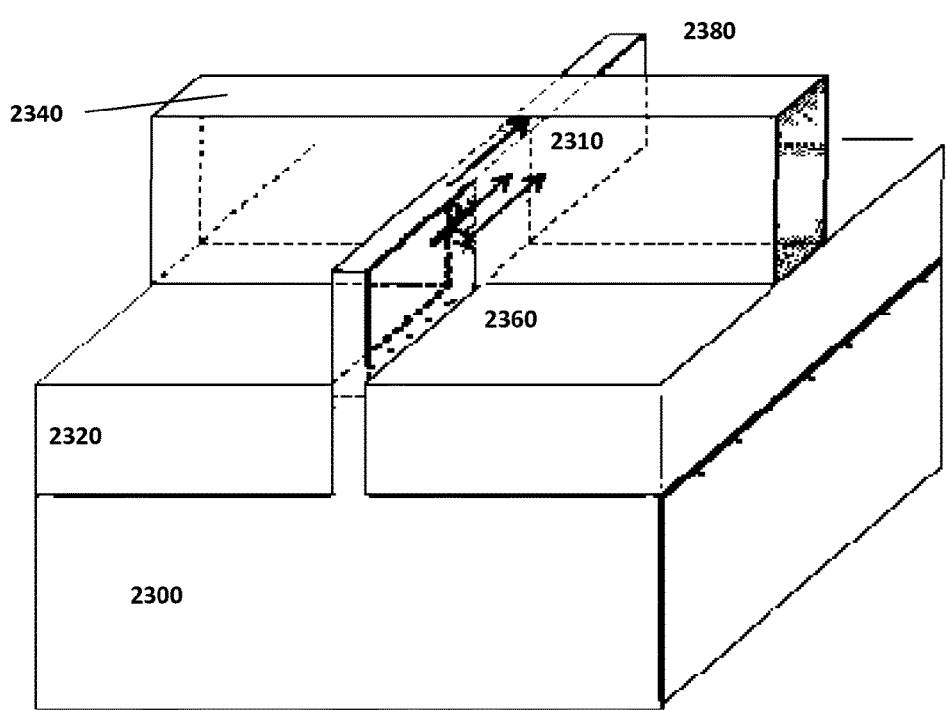
FIG. 23 schematically illustrates an example of a system that utilizes a sensor arranged in a manner similar to a Fin field effect transistor (FET) type sensor.

In some embodiments, the system may utilize a sensor, such as a bridge sensor, which is arranged in a manner similar to a Fin FET, shown in FIG. 23. In some embodiments, the Fin FET type sensor is comprised of a silicon substrate 2300 covered by an oxide layer 2320. There may be a gate 2340 on top of the oxide layer, as well as a sensor fin 2310, a source 2360 and a drain 2380. In some embodiments, the three sided gate 2340 may be accessible to interact with the target molecules in the surrounding environment, such as, for example, DNA that is bound to the surface of the fin, channel, bead, etc. The sensor fin 2310 may have a vertical dimension perpendicular to the substrate 2300, said vertical dimension being greater than the horizontal cross section of fin 2310. Such a device may have greater sensitivity than a device which has but a single surface accessible to the surrounding environment. The Fin FET sensor can be fabricated from or on a Silicon-on-Insulator or SOI structure.

Chamber Free Amplification

In the process of amplifying DNA in a chamber-free system as described in provisional application 61/491,081, various factors are potentially subject to optimization. As explained in the application, in some embodiments, electric fields are used to attract template DNA, dNTPs, and primers to a "confinement cell" region or "chamber-free amplification" region. Amplification then begins in the region of each cell where template DNA is located. During the amplification process, the electric fields may also aid in preventing cross contamination between different confinement cells undergoing amplification by retaining amplicons. In order to insure that polyclonal regions are not generated, the concentration of input DNA may need to be low enough such that most confinement cells have one or zero sample DNA molecules. DNA samples can be single stranded or double stranded depending on the amplification methodology. In some embodiments, DNA molecules may be added to the beads prior to loading in the chamber free amplification array. Some factors potentially subject to optimization include the frequency, voltage, type of signal input, shape of signal input, absolute value of voltage, duty cycle, and dimensions of the electric field confinement cell used to confine the polymerase, template DNA, and generated amplicons. If confinement were the only consideration, it would be possible to confine almost any size of amplicon, without regard to the small size of said amplicon. A field that is strong enough to ensure proper confinement, however, may also prevent proper activity of the polymerase incorporation of bases during the PCR or isothermal amplification process. Proper arrangement in the field and applied voltage, frequency and duty cycle and reaction conditions, may ensure that the field does not pull the polymerase and/or extended primer from the complex of the target DNA extended primer and polymerase.

In one embodiment, it may be desirable to optimize a combination of frequency, voltage and size of the confinement cell, depending on the size of the amplicon. For example, the size of the confinement cell can be 1, 3, 5, 10, 12, 20, 25, etc. μm in length or diameter and different shapes, for example, squares. The frequency can range from a DC signal (0 Hz) to an AC signal of a few Hz to several kHz or MHz. The voltage can consist of, for example, 1V AC with 500 Hz frequency with a 1.2 V DC offset. Chamber-free amplification can be achieved using either electrophoresis or a dielectrophoretic field, or both.

In order to induce dielectrophoresis, an array of electrodes can be used to create non-uniform electric fields. The electrode configuration may take various forms, including an outer electrode that defines the outside of the confinement cell and an inner electrode, or there may be two inner electrodes proximate to a bead, for example, the magnetic bead, with a magnet located such that it retains the bead proximate to the electrodes.

In generating a dielectrophoretic field, typically a sinusoidal waveform is utilized. While this may be ideal for an application that is intended strictly for confinement or separation of different species, it may cause issues for a system wherein a biochemistry reaction may be performed within the confinement volume. If a system utilizes a sinusoidal waveform, the speed of the charged species may be highest as it passes the center of the confinement volume; thus, at the point where it may be most desirable for polymerase activity to occur, the polymerase may be least likely to be able to function as intended.

In an alternative embodiment, a modified sinusoidal waveform may be utilized. For example, the modified sinusoidal waveform may have the voltage removed at the top of the sinusoid, allowing for localized diffusion, permitting hybridization of the amplicons to primers, binding of polymerase to the duplex DNA, and binding and incorporation of nucleotides or nucleotide analogs. The field may then be reinstated after an appropriate period of time. The same process may occur at the peak with the opposite sign in the modified sinusoidal waveform. Alternatively, the interruption in the sinusoidal waveform may occur only once per cycle, or may occur once in every several cycles, or once in many cycles, so that any "stray" amplicons may be captured in the regions with lowest field strength and returned to the main volume of the confinement volume. Alternatively, other wave forms such as square, trapezoidal, non-symmetrical wave forms, etc. maybe used.

Dielectrophoresis may present challenges with respect to voltage requirements and size limitations on the target particles. The effective confinement and separation of smaller particles may be problematic. In another embodiment, electrophoresis can be used, either alone or in conjunction with dielectrophoresis, for confinement or separation of various species by the application of a uniform electric field. This method may allow for more effective control over small particles.

Figure 24:
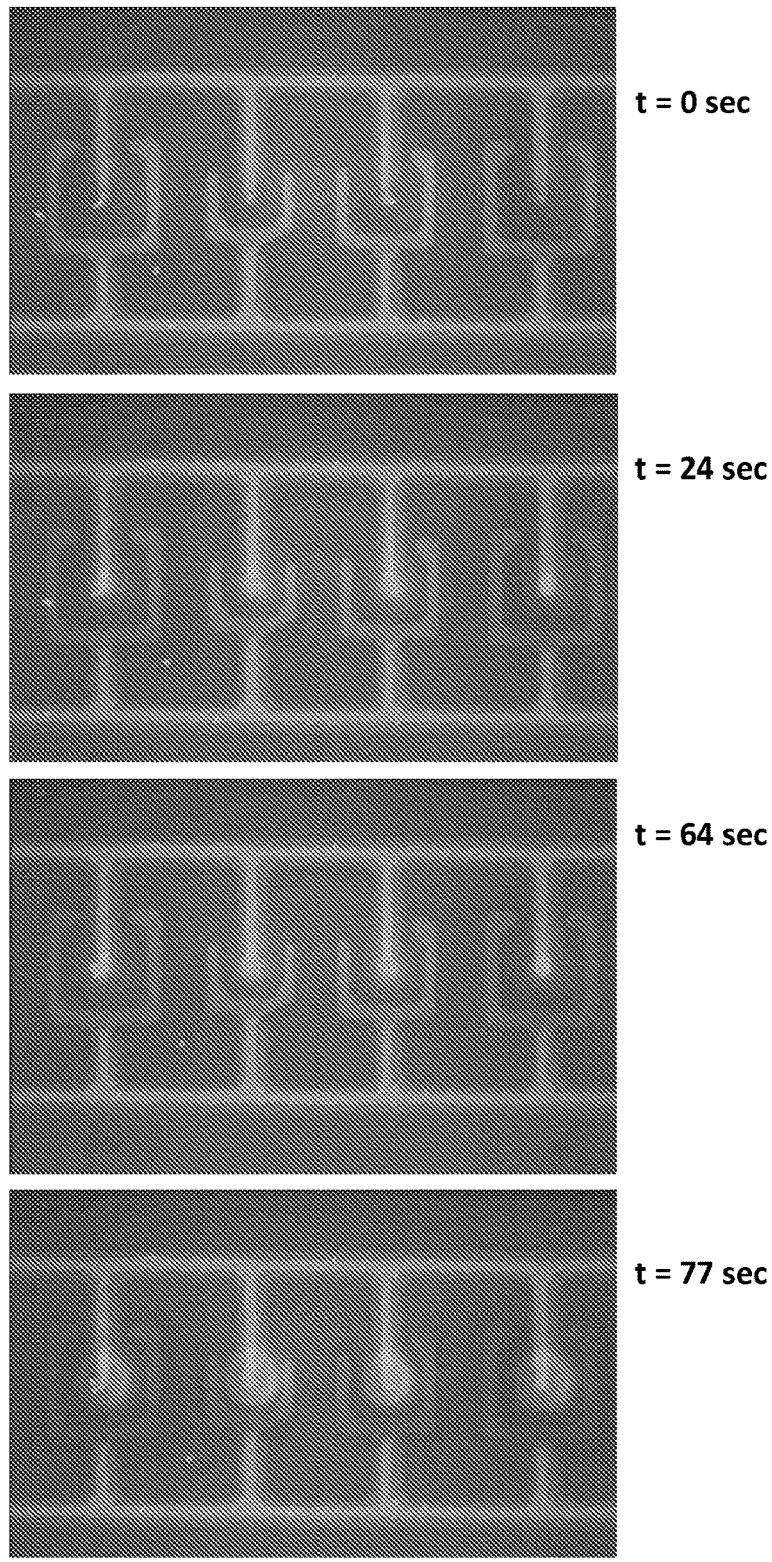
FIG. 24 illustrates an example of the effect an electric field has on DNA concentration over time.

In one embodiment, a DC signal is applied between one or more electrodes to generate one or more DC electric fields. Furthermore, an AC signal is applied between one or more electrodes to generate one or more AC electric fields. The function generated may be a combination of two or more of a DC signal, a DC pulse, and an AC signal. FIG. 24 illustrates, in one embodiment, the effect the electric field has on DNA concentration over time (t) in a confinement cell. The photographs illustrate the different intensity of DNA concentration over time from 0 seconds (where there is no electric field) to 77 seconds after the electric field has been turned on. For example, the photograph at 0 seconds has fewer, less intensely lit areas around the confinement cell than the photograph at 77 seconds.

The frequency of the DC pulse can range from, for example, 1 Hz to 10 kHz. The voltage can oscillate between approximately, for example, +/−1.3 V, allowing for electrolysis at the upper range. In this manner, the field may be removed in order to allow for biochemical reactions to progress without any potential interference and then later the field may be reinstated at an appropriate time.

Figure 25:
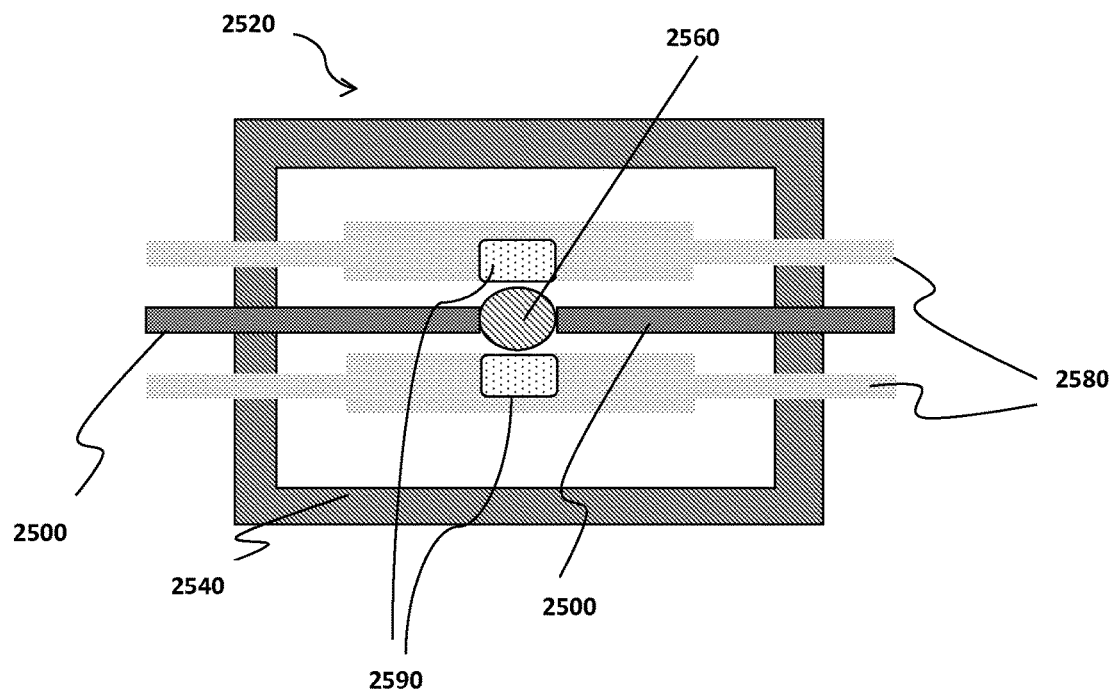
FIG. 25 schematically illustrates an example of a magnet associated with a confinement cell.

The confinement cell functions in such a manner to both contain and concentrate the target particles of interest, such as for example DNA for DNA amplification. In one embodiment, a carrier, such as a magnetic bead, is loaded into a microfluidic channel. As depicted in FIG. 25, in some embodiments, a magnet 2500 associated with a confinement cell 2520 retains a bead 2560. Reagents, such as for example DNA template strands, DNA polymerase, primers, etc. are then passed through the microfluidic channel and contained by an outer electrode 2540 of confinement cell 2520. This outer electrode 2540 may have a negative charge in order to keep the negatively charged DNA molecules within the area of confinement cell 2520. The bead 2560 may be located between two inner electrodes 2580, a portion of which remain uncovered 2590 by a dielectric layer, and the DNA plus reagents may be concentrated in that region. The template DNA may be bound to the bead through the use of a linker, such as a biotin-streptavidin bond. Amplification of the template DNA strand on the bead can then occur through techniques such as PCR or isothermal amplification. For example, a method based on an isothermal amplification using nick restriction enzyme and strand displacement DNA polymerase can be used. The amplicons may be contained by the inner and outer electrodes, facilitating a more effective amplification process by limiting the diffusion of particles away from the bead.

In a further embodiment, the template DNA strands that are delivered in a low concentration in order for most beads to have one or zero template DNA strands per bead. In an alternative embodiment, the loading step is modified such that DNA template strands are bound to beads so that there is approximately one DNA template strand per bead. The beads are then loaded into the microfluidic channel and captured by the magnets associated with the confinement cells. Reagent delivery/concentration and DNA amplification occur in the same manner as described in the previous embodiment. In a further embodiment, the target molecule, such as DNA, may be bound to a surface of the substrate, or may remain unbound as part of the solution.

Figure 26:
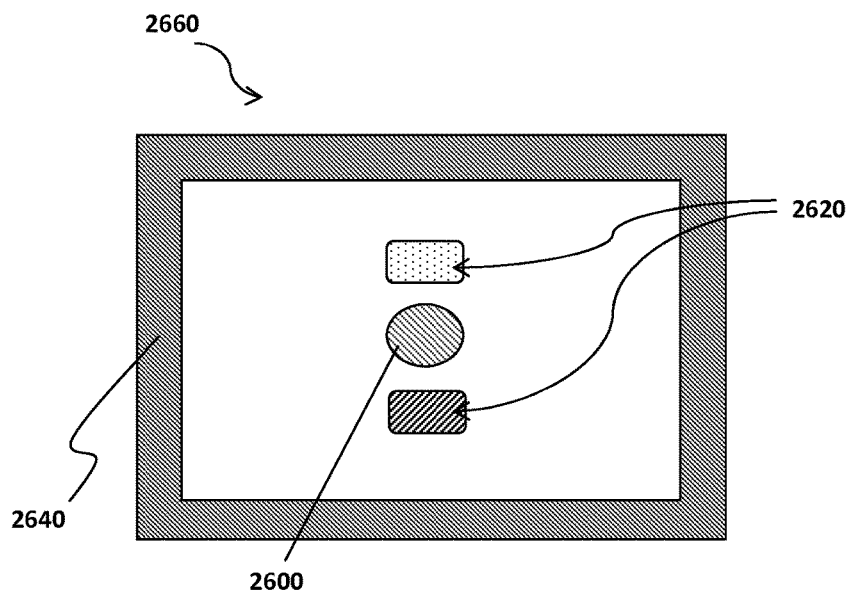
FIG. 26 schematically illustrates an example of inner electrodes with alternative positive and negative polarities.

In some embodiments, the inner electrodes may have alternating positive and negative polarities or charges, as shown in FIG. 26, so as to concentrate the template DNA and reagents in close proximity to the bead 2600 located between the inner electrodes 2620. Said inner electrodes 2620 alternate back and forth between positive and negative charges. In this manner, DNA and reagents used for amplification may be passed back and forth between the inner electrodes 2620, concentrated in an area on or proximate to bead 2600, and prevented from attaching to an electrode of opposite charge. The electric field generated by the negatively charged outer electrode 2640 can be an additional barrier, preventing the diffusion of the negatively charged DNA away from the confinement cell 2660. In this manner, DNA and reagents may be concentrated on or near the bead, allowing for an increase in efficiency of the amplification reaction. In some embodiments, the impact of local pH change around the bead may be controlled with the distance of the inner electrodes from the bead.

Figure 27A:
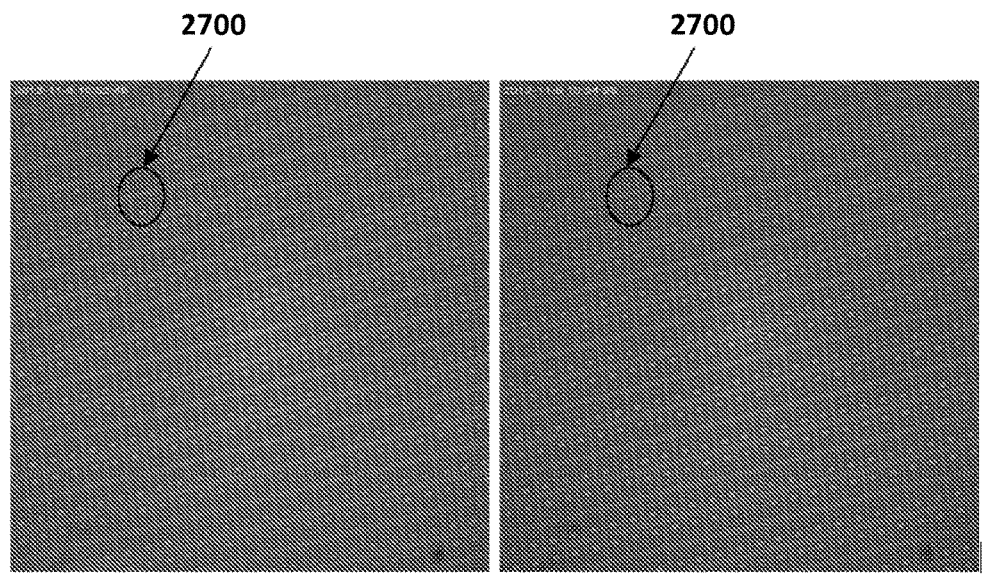
FIG. 27A shows an example of alternating positive and negative charges of an inner electrode coordinated between neighboring cells.

In a further embodiment, as shown in FIG. 27A, the process of alternating the positive and negative charges of the inner electrodes is coordinated between neighboring cells 2700, as can be seen by the alternating lit regions in comparing the left and right photograph. This process may be coordinated such that the neighboring electrodes of adjacent cells may have the same polarity or charge (positive or negative) at the same time and then the electrodes may switch to the opposite polarity or charge at the same time. In this manner, the electric field between adjacent cells points inward, preventing diffusion of particles outside of the confinement cell.

Figure 27B:
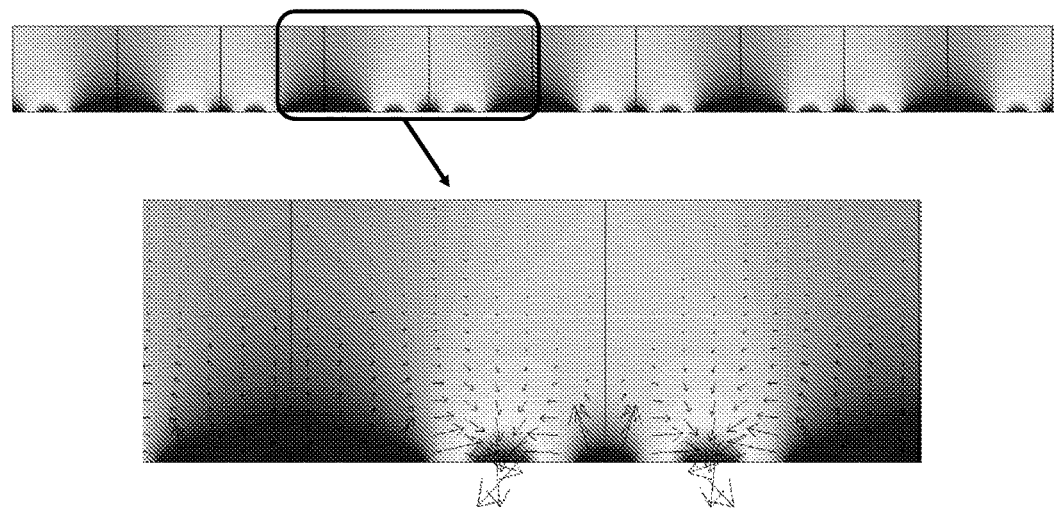
FIG. 27B shows an example of a two-dimensional depiction of neighboring cells with coordinated alternating charge.

In some embodiments, the effect of having the electrodes of neighboring cells with coordinated alternating charge is shown in the 2-D depiction in FIG. 27B, wherein the electric field lines (AC=1 V, 2 Hz; DC=1V) of adjacent cells are pointing inward due to the neighboring electrodes having the same charge.

Figure 27C:
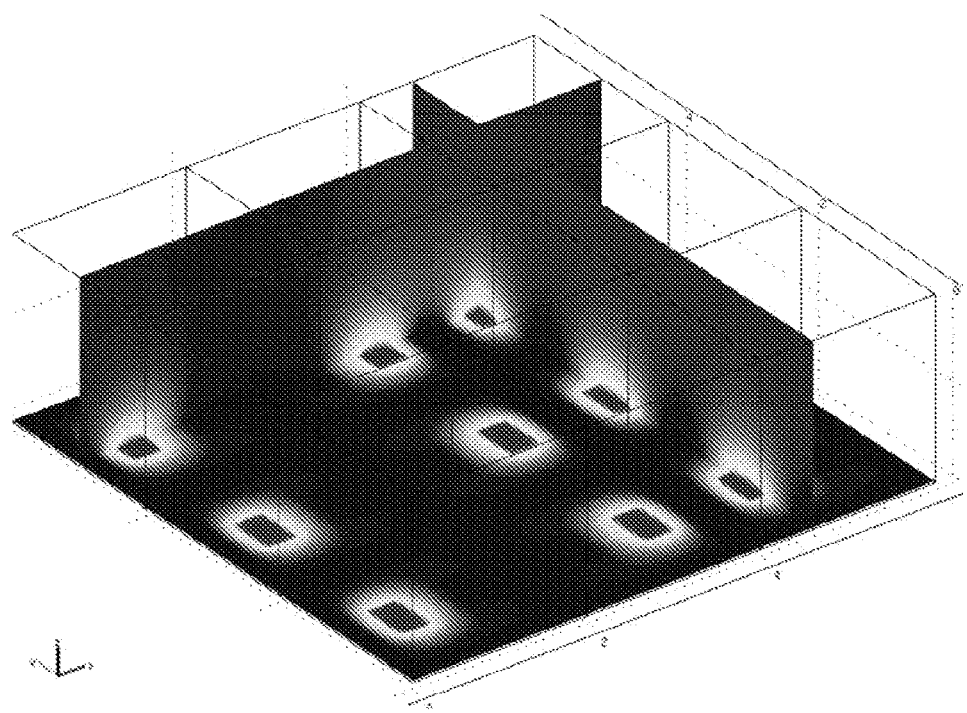
FIG. 27C shows an example of a three-dimensional depiction of neighboring cells with coordinated alternating charge.

In a further embodiment, FIG. 27C illustrates the same concept as in FIG. 27B, but in a 3-D representation. The lit up regions of the diagram represent neighboring electrodes of different pixels, said neighboring electrodes having the same during the same time period.

Potential problems may arise if the distance between the target particles and the electrodes is not sufficient. At higher voltages, electrolysis may occur and this may cause issues such as, for example, bubbles and/or a drop in pH in the area proximate to the electrode. These changes may have an effect on the DNA amplification or biochemical reaction of interest. In a further embodiment, the placement of the electrodes may be such that there is sufficient distance between the electrodes and the particles to allow for the prevention of undesirable interactions due to a change in pH or bubble formation, yet the electrodes are in close enough proximity to the particles in order to allow for their confinement or separation.

There may be optimization with respect to the configuration of the electrode edges, shape, dimensions, configuration, materials, number of inner electrodes, etc. In some embodiments, the edges of the electrodes may be sharp. In other embodiments, the edges may be more rounded. All or some of the electrodes may have the same edge shape or all of the electrodes may have different edge shapes. The shape/sharpness of the electrodes may have an impact on the strength and direction of the associated electric field and can be optimized for an application of interest.

In some embodiments, the electrodes may have a rectangular shape. In other embodiments, the electrodes may be curved, circular, square, etc. or any other shape.

The outer electrode may have a pitch size of 2 µm, 5 µm, 10 µm or smaller, or it may have a larger size such as 12 µm, 15 µm, 20 µm, 25 µm, or more. The pitch size may have an impact on the efficacy of DNA confinement. For the same applied voltage, a confinement cell with a larger pitch size has a smaller field strength associated with it as compared to the field strength of a cell with smaller pitch size. If the confinement cell proportions are designed to maintain the same ratio, said difference in field strength may be due to the closer proximity of the inner electrodes to each other in a cell with a smaller versus a larger pitch size.

A larger pitch size, however, may be desirable in that its proportions create a longer path for diffusion of target molecules outside of the confinement cell. Furthermore, a larger pitch size allows for a larger range of the associated electric field. In this manner, a larger pitch size may be desirable in order to capture or prevent the diffusion of target molecules towards the top of the channel.

The electrodes may be composed of, for example, 10/200 nm Ti/Pt to have minimal corrosion during electrolysis, or they may be composed of gold, iridium, etc., or another metal or material. In some embodiments, some portion of the inner or outer electrodes may be covered with a dielectric material in order to prevent unwanted contact or interference from adjacent electrodes, reagents, bulk solution, etc. There may be optimization with respect to the shape and size of the dielectric layer on the electrode. Depending on the desired electric field strength, the uncovered portion of one or more electrodes may be, for example, 100 nm×100 nm, 500 nm×500 nm, 1 µm×1 µm, 4 µm×3 µm, etc. or another dimension. The uncovered portions of one or more electrodes may also very in shape, such as rectangular, square, circular, or any other shape.

In some embodiments, the confinement cell consists of an outer electrode and two inner electrodes. The outer electrode may define the outer perimeter of the confinement cell, for example, forming a square border. The thickness of this outer electrode may be 30 nm, 100 nm, 1 µm, 2 µm, 3 µm, etc. In a further embodiment, one or more inner electrodes may be located within the outer electrode and have dimensions of, for example, 4 nm×12 nm, 6 nm×15 nm, 80 nm×200 nm, 3 µm×9 µm, 6 µm×11 µm, 10 µm×25 µm, etc. or another dimension. The dimensions of the inner and outer electrodes can impact the strength and range of the electric field, and thus the efficacy of confinement of target particles.

Figure 28:
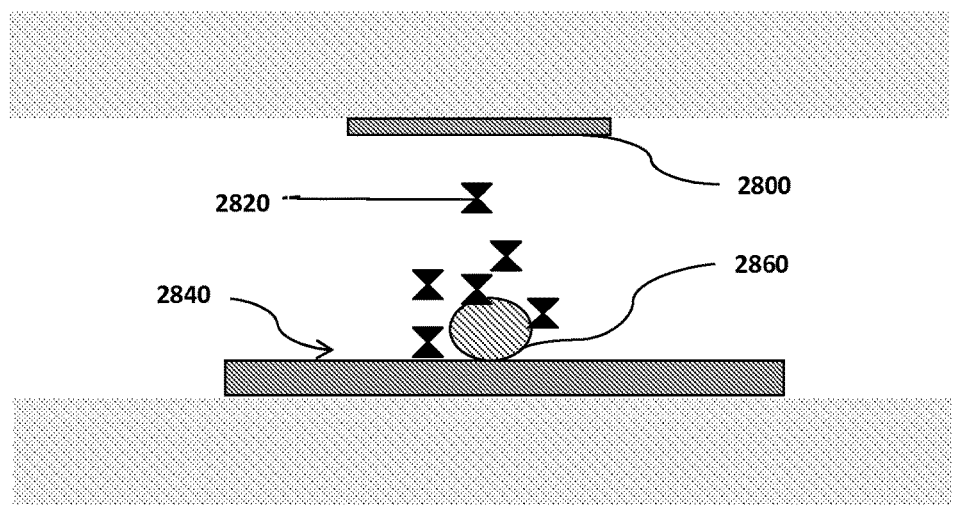
FIG. 28 schematically illustrates an example of an electrode placed outside of the confinement cell.

In a further embodiment, there may be one or more electrodes placed outside of the confinement cell, such as for example at the top of the channel, as shown in FIG. 28. The electrode 2800 may have a negative charge such that it provides another electric field to help drive the negatively charged DNA molecules 2820 into the confinement cell 2840 and onto the bead 2860.

In some embodiments, the channel height may be optimized for factors such as loading beads, clearing beads, injecting reagents, washing reagents, ideal flow conditions, preventing blockage of the channels, keeping reagents within range of the electric field, etc., or other aspects. In one embodiment, the minimum channel height required to avoid blockage or other potential problems is about 3 to 5 times the height of the bead. In other embodiments, a higher channel height may be used.

In some embodiments, one or more magnets can be used to retain the magnetic carrier, such as for example a magnetic bead. The magnets may be composed of, for example, Ni, Fe, Co, CoPt, CrCoPt, NiCoPt, or another combination of materials. Various aspects of the magnets may be altered in order to gain the desired magnetic force and field. Such aspects subject to optimization may include, for example, the magnet material, number of layers, thickness, length, sharpness of edges, shape, configuration etc. The magnet may be composed of a paramagnetic material, for example aluminum, platinum, etc., or any other paramagnetic material or a ferromagnetic material, for example, iron, nickel, etc., or any other ferromagnetic material, or a combination of materials.

An adhesion layer may be deposited below or on the magnetic region that has, for example, a "bar" shape, prior to deposition of the magnetic layer. The adhesion layer may consist of, for example, Chromium, Titanium, or another adhesive material. This adhesive layer may be 1, 3, 5, 10, 15, or 20 nm in thickness or another thickness. The bar may be magnetized through sputtering of a magnetic layer. The magnetic layer may consist of, for example, platinum or any other magnetic material. The sputtered magnetic layer may be more or less than, for example, 30 nm, 50 nm, 70 nm, 150 nm, 200 nm, 410 nm, etc. in thickness.

In some embodiments, there may be "n" number of magnets such that the number of beads equals "n+1". In an alternate configuration, there may be "n" number of beads and "n+1" bars or any other combination such as n beads and b bars or 2×n beads with n bars, etc. In some embodiments, depending on the desired configuration, there may be, for example, one, two, etc. beads per magnet.

Figure 29:
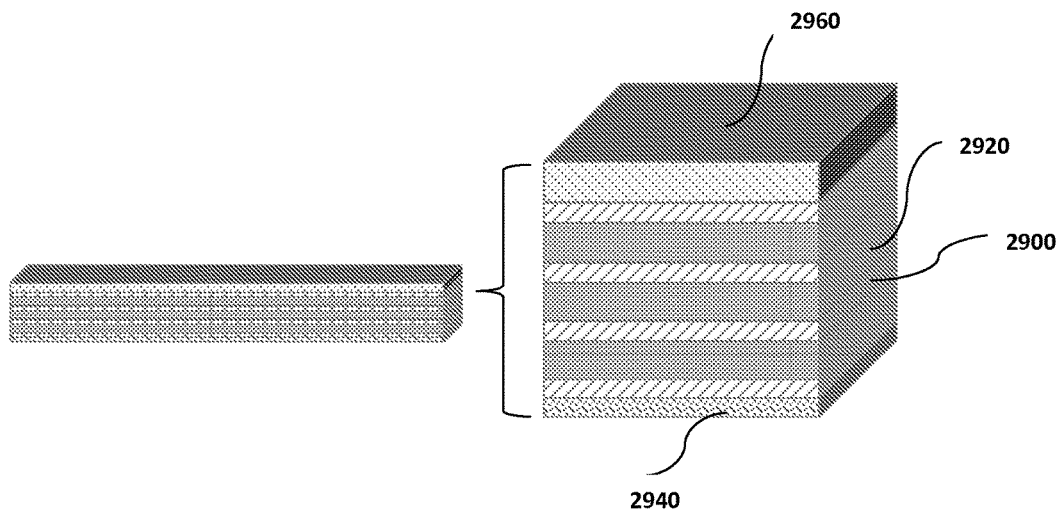
FIG. 29 schematically illustrates an example of a magnet with a layer composition.

In one embodiment, the magnet may have a "sandwich" layer composition, shown in FIG. 29, wherein the figure illustrates a close-up view of the layers. The sandwich layers may be composed of, for example, alternating layers of non-magnetic 2900 and magnetic 2920 materials. This configuration may allow for a stronger magnetic force because isolating the magnetic layers through the addition of alternating non-magnetic layers increases the probability that the magnetic domains may align to maximize field strength without interference from other magnetic domains. These alternating layers can be, for example, Chromium and/or Platinum or another material. In some embodiments, the magnetic layer can be 10 nm or less and the non-magnetic layer can be 2 or 4 nm, or 12 nm and 10 nm respectively, or any other dimension. In some embodiments, the magnetic layer can be more than 10 nm, such as 20 nm, 35 nm, 70 nm or any other dimension.

Furthermore, in some embodiments, there may be a base layer 2940 composed of Chromium/Titanium, that may be, for example, 3 nm, 6 nm, 8 nm, 14 nm, etc. thick.

In some embodiments, there are eight layers, which may include a top oxide layer 2960, plus an additional layer for the base.

In further embodiments, the magnet may be, for example, 70 nm, 7 µm, 10 µm, 20 µm, etc. in length. The height of the magnet, which may be composed of multiple sandwich layers, may be 10 nm, 70 nm, 200 nm, 0.5 µm, 1 µm, 2.8 µm, 5 µm, 10 µm, etc.

The sharpness of the edges of the one or more magnets may vary depending on the magnetic force that is desired. In some embodiments, the edges of the magnets may be sharp such that a stronger magnetic field and/or force is generated. In other embodiments, the edges of the magnets may be less sharp in order to achieve a smaller magnetic force. The strength of the magnetic force may affect the efficacy of bead capture and the ease of bead washing.

Figure 30:
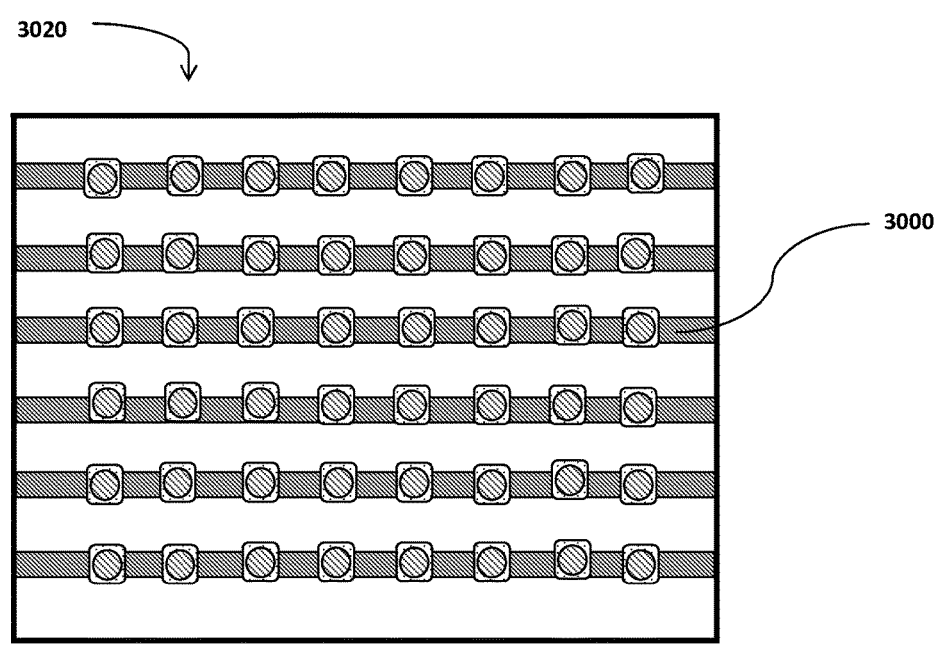
FIG. 30 schematically illustrates an example of magnetic bars that run along the length of a confinement cell array.

The shape of the one or more magnets may also vary. In certain embodiments, for example, the magnets may have a square, rectangular, circular, etc. shape. The shape may also have an effect on the force of the magnetic field. As depicted in FIG. 30, in some embodiments, there may be magnetic bars 3000 that run along the length of the confinement cell array 3020.

Figure 31:
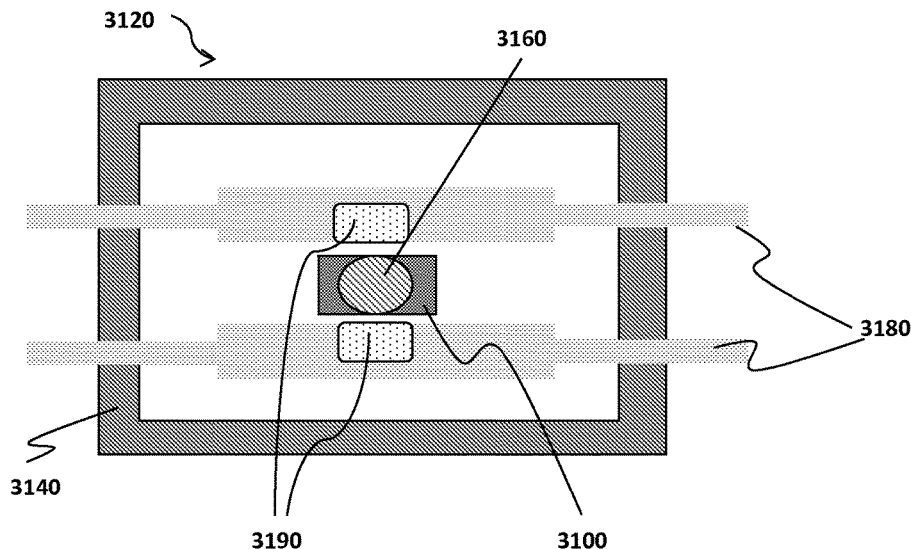
FIG. 31A schematically illustrates an example of a magnetic bead associated with a confinement cell.
Figure 32:
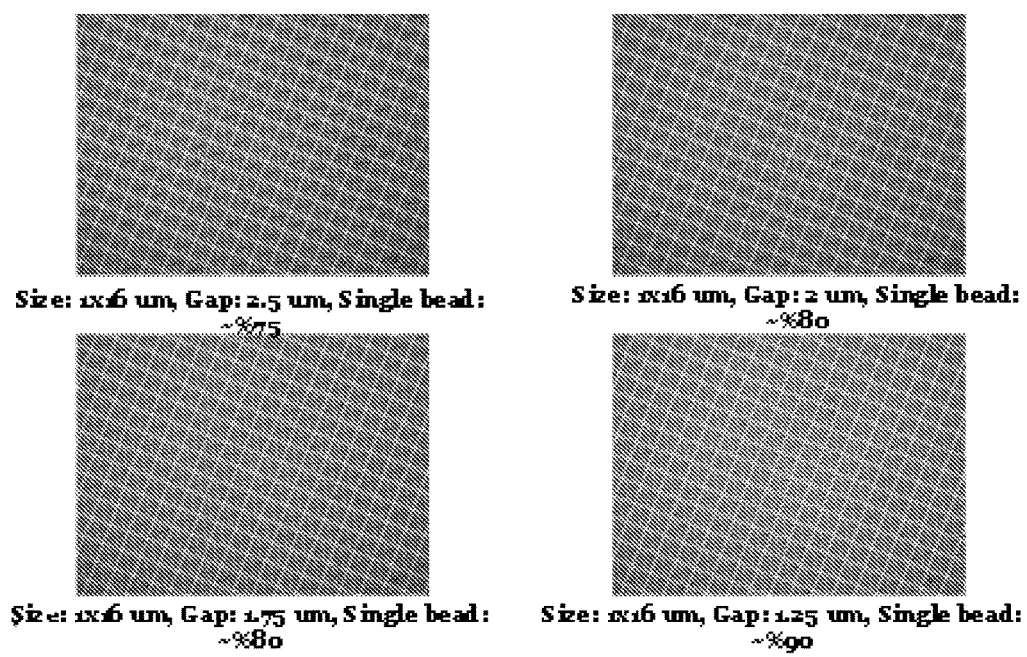
FIG. 32 shows an example of the effect of gap size on bead capture efficiency.

In FIG. 31A, in some embodiments, the magnetic bead 3160 associated with a confinement cell 3120 is located above one magnet 3100. The bead 3160 is proximal to an outer electrode 3140 and two inner electrodes 3180. Some portion 3190 of the inner electrodes may not be covered by dielectric material. In an alternative embodiment, there are two magnets associated with one confinement cell, as shown in FIG. 25. These two magnets 2500 may run through the middle of the cell 2520, with the end of the magnets facing each other at or near the middle of the cell. This configuration may create a gap (not shown) between the two magnets, near the middle of the cell. A magnetic force may result from this configuration, and a carrier, such as a bead, may be retained by this force, resting on or within the gap. This gap size can be, for example, 50 nm, 100 nm, 0.25 µm, 1 µm, 1.5 µm, 2 µm, 2.5 µm, etc. wide. The gap size may be optimized to allow for a desired magnetic force upon the bead. Varying parameters such as, for example, gap size can lead to optimization of such factors as bead capture efficiency, as shown in FIG. 32. In one embodiment, as shown in the figure, using a 1.25 µm gap size may result in single bead capture efficiency of approximately 90% for the bead size of 2.8 µm in diameter. In some embodiments, the confinement cell axes and the axis of magnetic bars may have an angle, for example, 11°, 15°, 18°, or 30° for optimization of high efficiency magnetic bead capturing and fill factor.

Figure 33A:
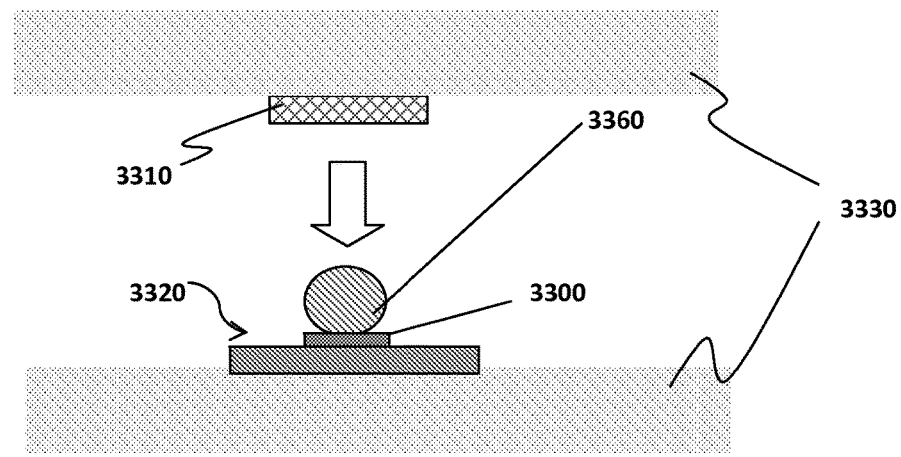
FIG. 33A schematically illustrates an example of a magnet located on top of or outside of the confinement cell.

In FIG. 33A, in another embodiment, in addition to one or more magnets 3300 located in the confinement cell 3320, there may be one or more outer magnets 3310 located on top of or outside of confinement cell 3320, for example, at the top of the channel 3330. In one embodiment, the outer magnet 3310 at the top of the channel 3330 may be ferromagnetic, for example, composed of iron. In an alternative embodiment, the outer magnet 3310 may be an earth magnet, for example, composed of samarium-cobalt. It can be inside or outside of the fluidic channel.

In a further embodiment, the outer magnet may be part of a mechanism that allows for it to be lowered close to or into the microfluidic channel at an appropriate time, and then allows for it to be removed out of range of the confinement cell by lifting or otherwise distancing it from the cell.

In some embodiments, at the appropriate time, the magnet outside of the cell may interact with the magnet inside of the confinement cell in order to generate a magnetic field that reaches a wider area. For example, a magnet that is placed at the top of the channel can interact with magnets inside of the confinement cell such that the magnetic field reaches to the top of the channel. This configuration may allow for a larger magnetic field range and thus an increase in bead capture efficiency. In another embodiment, the magnet on the outside of the confinement cell may not be a physical magnet, but instead a magnetic layer that is deposited on the channel.

In some embodiments, any of the magnetic regions or fields described herein may be created via electromagnetic structures or techniques, for example, a coil with passing current or other types of electromagnetic field generation. In some embodiments, permanent magnets may be used.

Figure 33B:
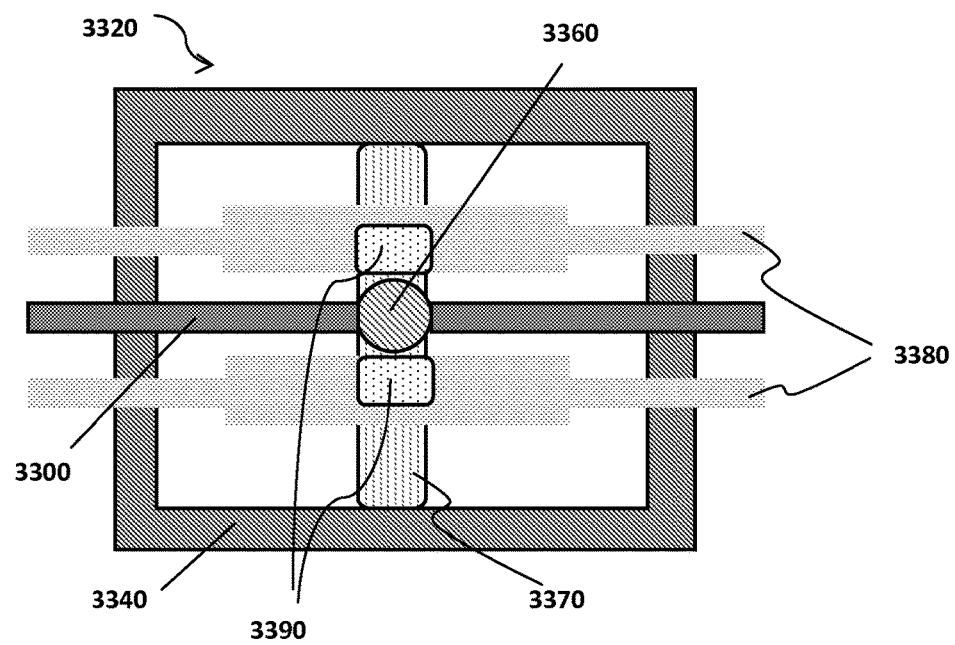
FIG. 33B schematically illustrates an example of one or more trenches located beneath a bead.

As shown in FIG. 33B, in a further embodiment, one or more trenches 3370 may be located beneath the bead 3360, such that the bottom surface of bead 3360 is made available for the delivery or the binding of the target molecules. In this manner, additional surface area is made available for the desired reaction, such as DNA amplification. The trench 3370 may have dimensions of, for example, 3×1 µm, 4×1 µm, 5×1 µm, 4×2 µm, etc. In another embodiment (not pictured), the trench 3370 may run across the length of the confinement cell array 3325, allowing for ease in delivery of reagents and improved washing.

There are a plurality of possible embodiments for the configuration of the confinement cell and associated aspects.

Figure 33C:
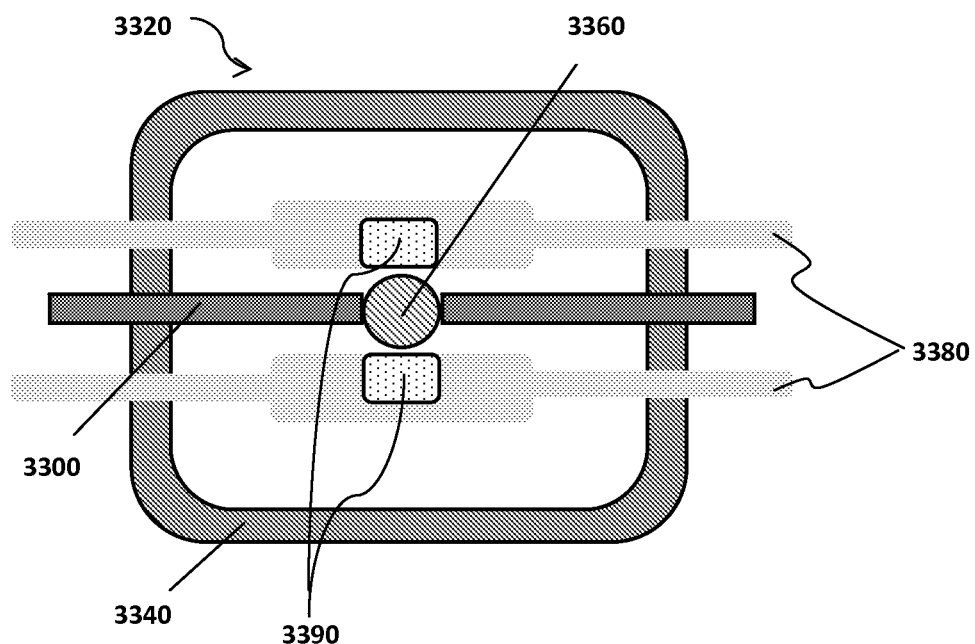
FIG. 33C schematically illustrates an example of rounded edges for both inner and outer electrodes.

In one embodiment, as shown in FIG. 25, the confinement cell 2520 consists of two inner electrodes 2580 surrounded by one outer electrode 2540, with both inner and outer electrodes having sharp edges. In alternative embodiments, as shown in FIG. 33C, the edges of both inner 3380 and outer electrodes 3340 are rounded or the inner electrodes have sharp edges and the outer electrode does not or vice versa. Some portion 3390 of the inner electrodes may not be covered by a dielectric material.

Figure 33D:
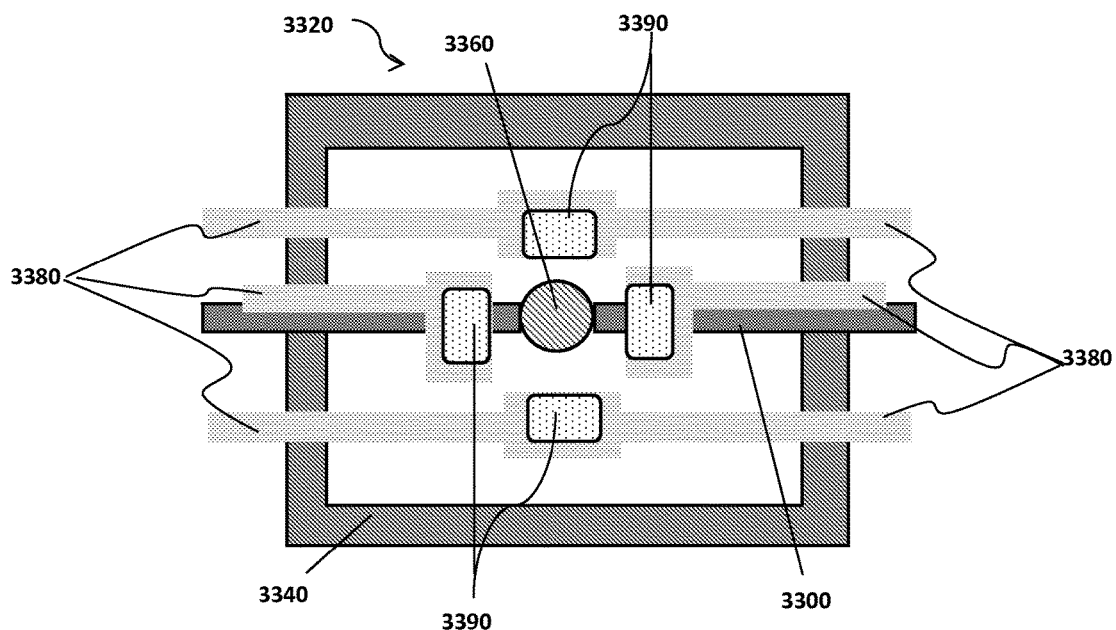
FIG. 33D schematically illustrates an example of a confinement cell with multiple inner electrodes.

In an alternate embodiment, as shown in FIG. 33D, confinement cell 3320 has multiple inner electrodes 3380, for example, it consists of four inner electrodes 3380. In a further embodiment, the multiple inner electrodes may vary in shape, for example, the electrodes may be circular, square, arched, etc. or any other shape.

Figure 33E:
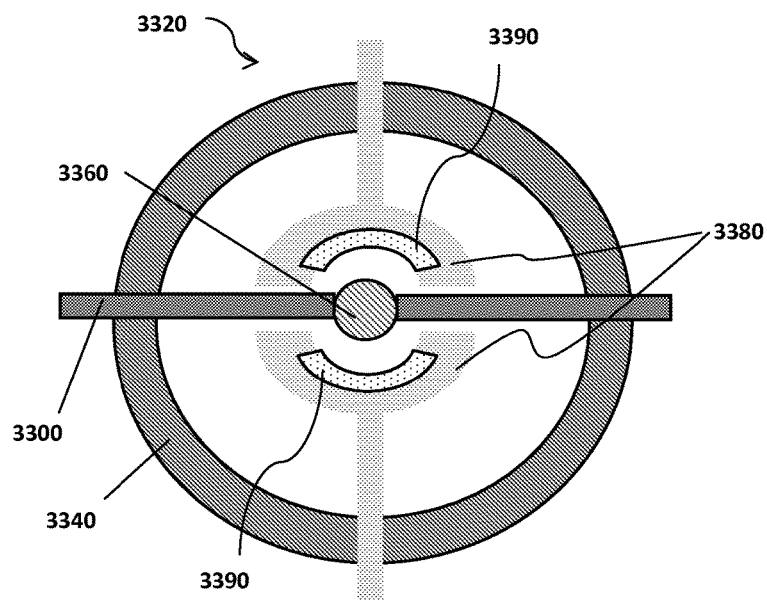
FIG. 33E schematically illustrates an example of inner electrodes in the shape of a semi-circle.

In a further embodiment, as illustrated in FIG. 33E, the inner electrodes 3380 may be in the shape of a semi-circle and the outer electrode 3340 may also be rounded.

Figure 33F:
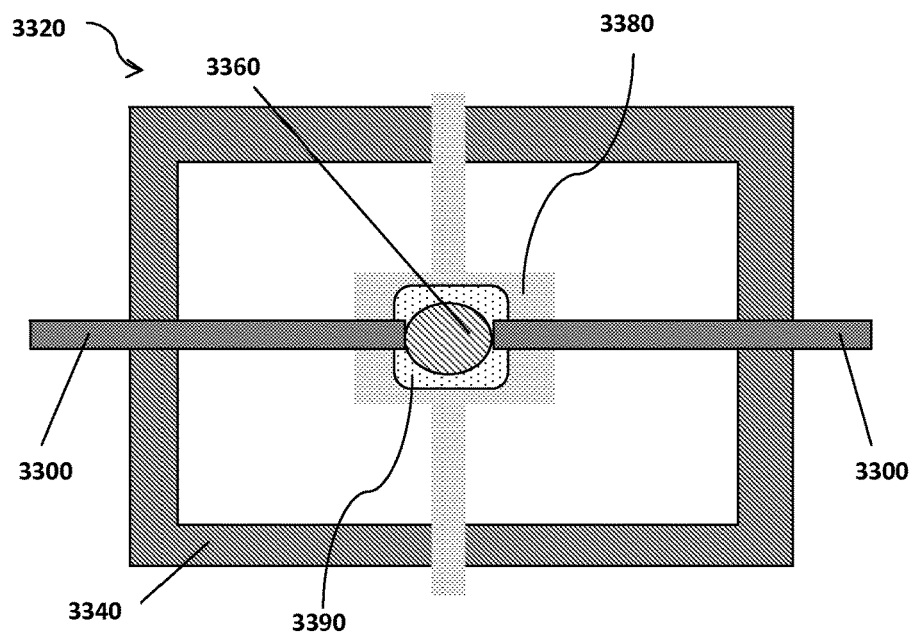
FIG. 33F schematically illustrates an example of an inner electrode with a bead located proximal to the inner electrode.

FIG. 33F illustrates that, in some embodiments, there may be one inner electrode 3380, with the bead 3360 located proximal to or above the one inner electrode 3380, and an outer electrode 3340 that surrounds said inner electrode 3380.

Figure 33G:
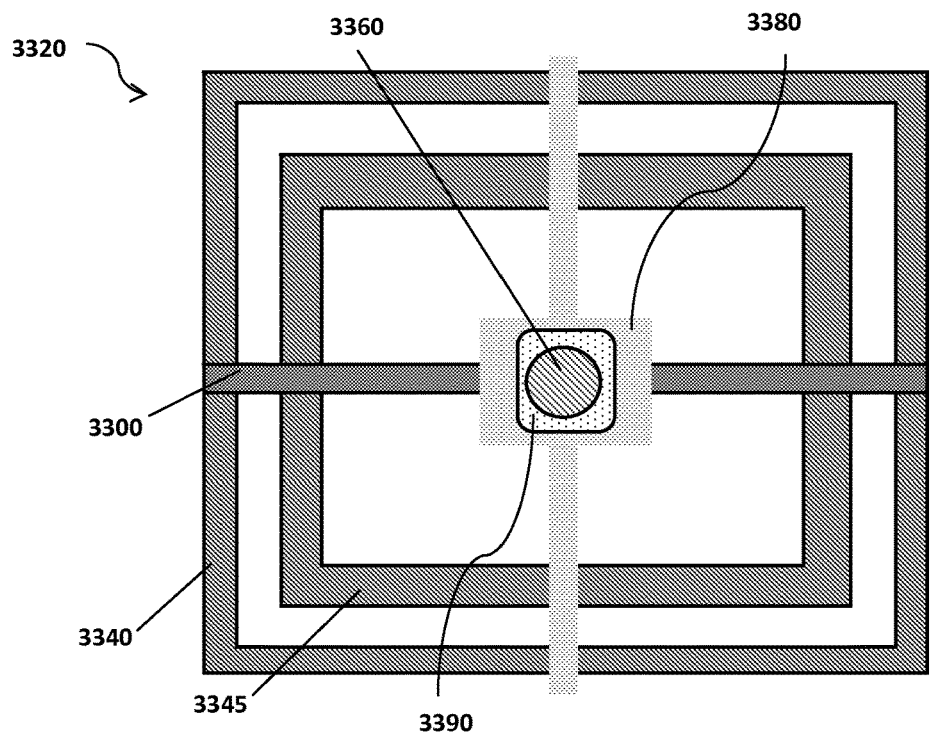
FIG. 33G schematically illustrates an example of an outer electrode that surrounds a smaller middle electrode that surrounds an inner electrode.
Figure 33H:
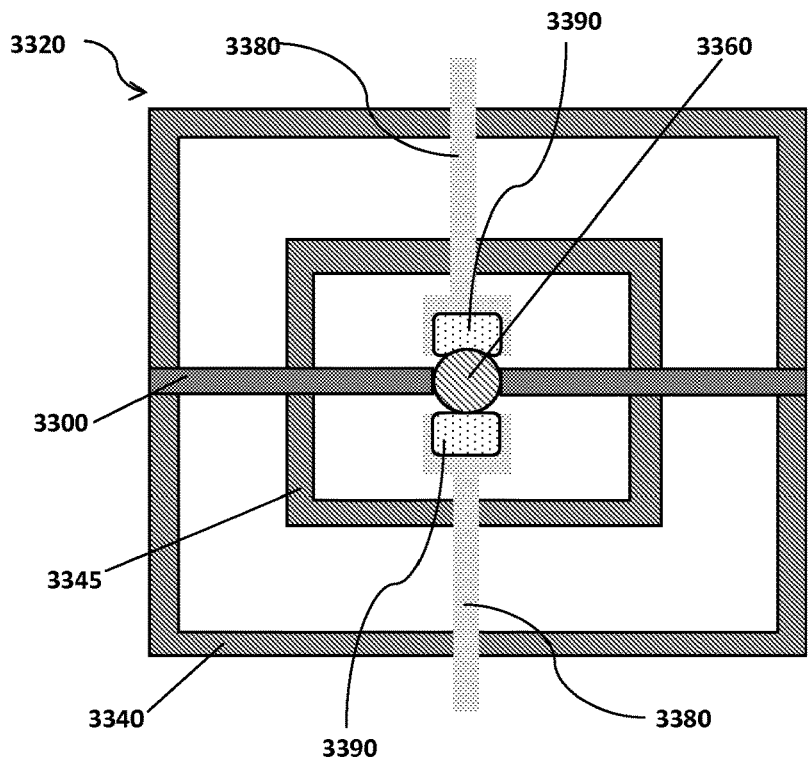
FIG. 33H schematically illustrates an example of more than one inner electrode.
Figure 33I:
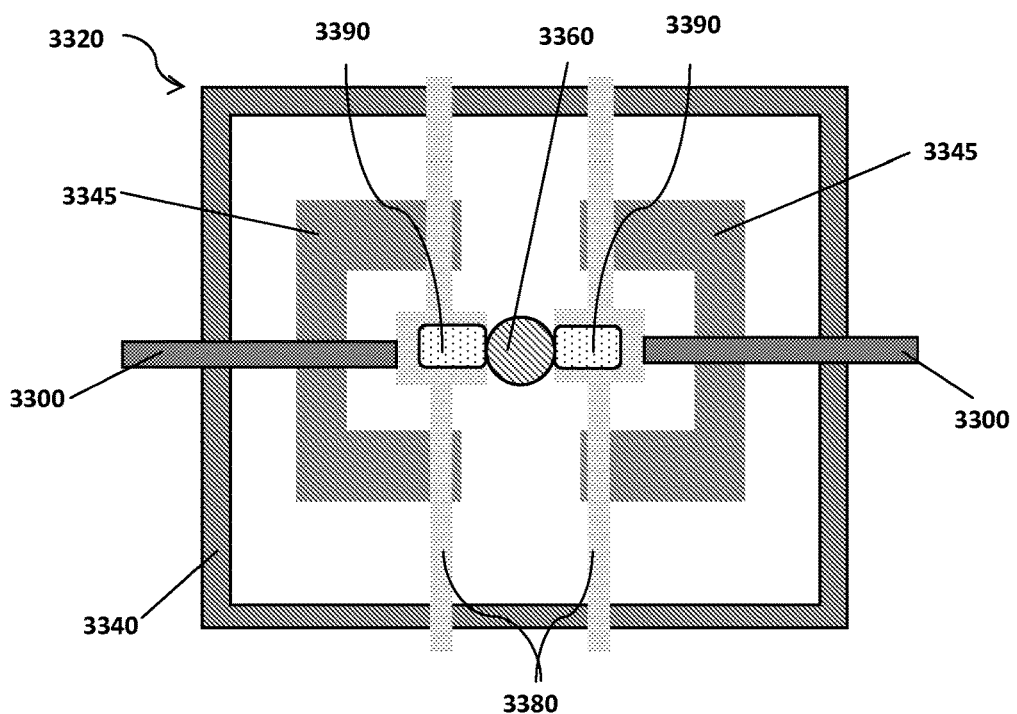
FIG. 33I schematically illustrates an example of an outer electrode along the perimeter of a confinement cell.

In alternate embodiments, there may be nesting electrode configurations wherein there are outer, middle, and inner electrodes. In one embodiment shown in FIG. 33G, for example, there may be an outer electrode 3340 that surrounds a smaller middle electrode 3345, wherein the said middle electrode surrounds one inner electrode 3380. In a further embodiment, shown in FIG. 33H, there may be more than one inner electrode 3380. In another embodiment, illustrated in FIG. 33I, there may be an outer electrode 3340 along the perimeter of the confinement cell 3320, and then two more middle electrodes 3345 that bracket two inner electrodes 3380.

In some embodiments, the confinement cell may be designed with a trench 3370, as was shown in FIG. 33B, or without a trench 3370, as was shown in FIG. 25. Some embodiments, as shown in FIG. 25, may have a configuration such that there is a gap between the magnets 2500 wherein bead 2560 may rest, or the cell can be designed such that the magnets 2500 are flush with the surface of the confinement cell (not shown).

Figure 33J:
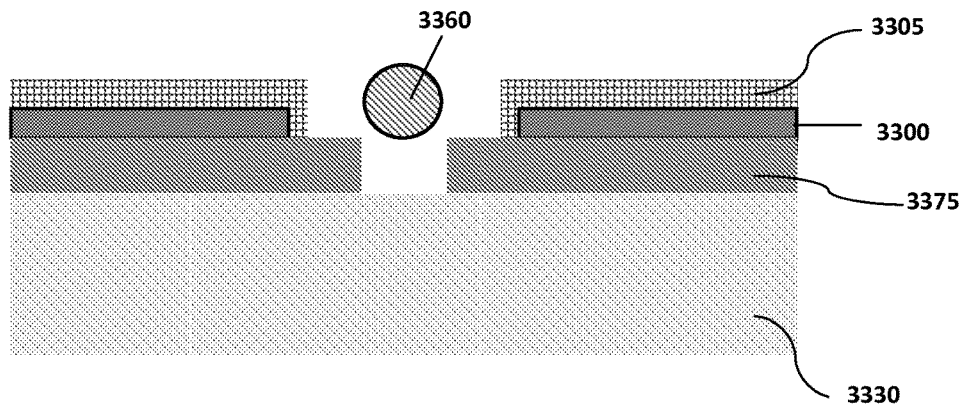
FIG. 33J schematically illustrates an example of magnets located on top of the electrodes.
Figure 33K:
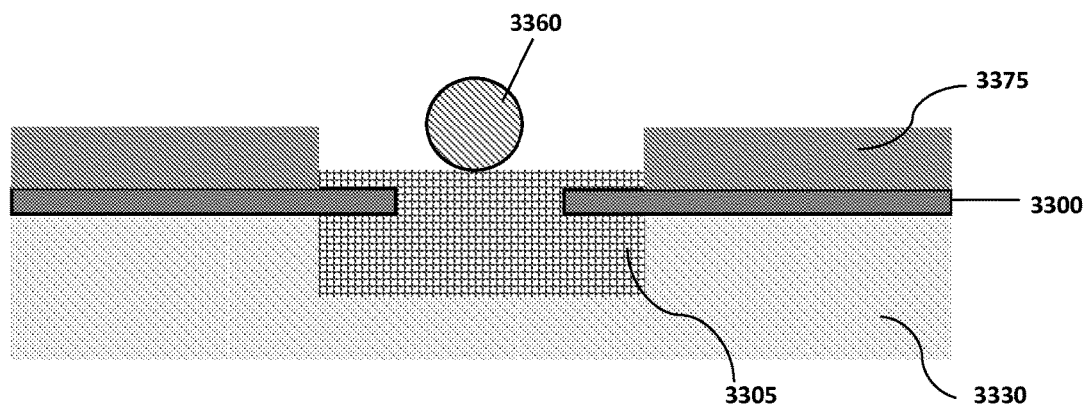
FIG. 33K schematically illustrates an example of electrodes located on top of magnets.

There may also be a variety of possible configurations for the location of the magnets with respect to the location of the electrodes. There may also be optimization with respect to which portion of the magnet is covered with an oxide layer in order to prevent or slow corrosion. In FIG. 33J, in one embodiment, the magnets 3300 may be located on top of the electrodes 3375, such that there is an overhanging portion where the electrodes 3375 are exposed and there is an oxide layer 3305 on top of the magnets 3300. In an alternate embodiment, as shown in FIG. 33K, the electrodes 3375 are on top of the magnets 3300 such that there is an overhang exposing the magnets 3300 and the magnets 3300 are covered by an oxide layer 3305. A portion of electrodes may be covered with an insulator layer (not shown). In both example embodiments, the bead 3360 may be located in the gap produced by the configuration.

Figure 33L:
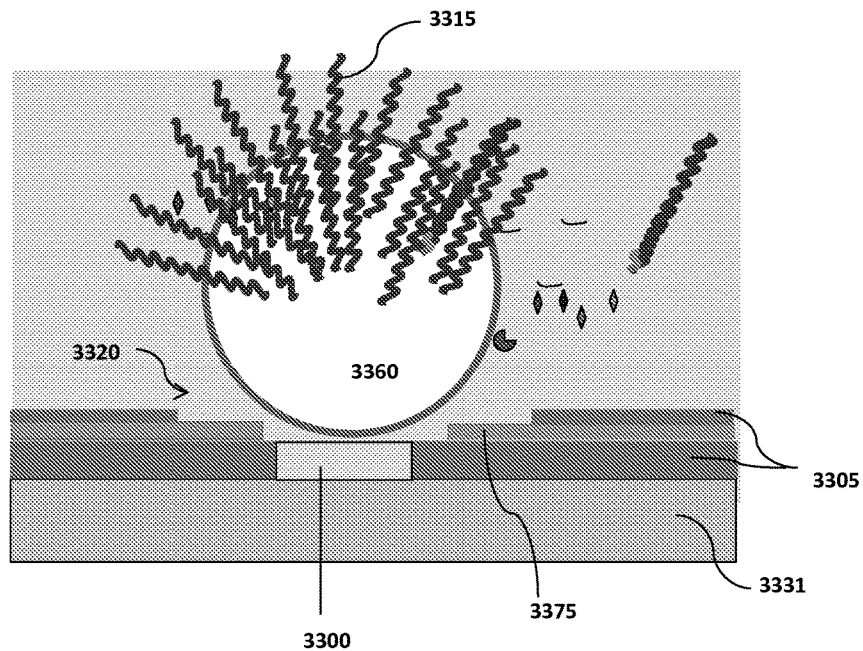
FIG. 33L schematically illustrates an example of a confinement cell above a substrate where a target reaction is occurring.

FIG. 33L illustrates one embodiment of a confinement cell 3320 above a substrate 3331 wherein a target reaction is occurring, such as for example DNA amplification, and the amplicons 3315 are bound to the bead 3360, located above the magnet 3300 and electrodes 3375 of the confinement cell 3320.

Figure 33M:
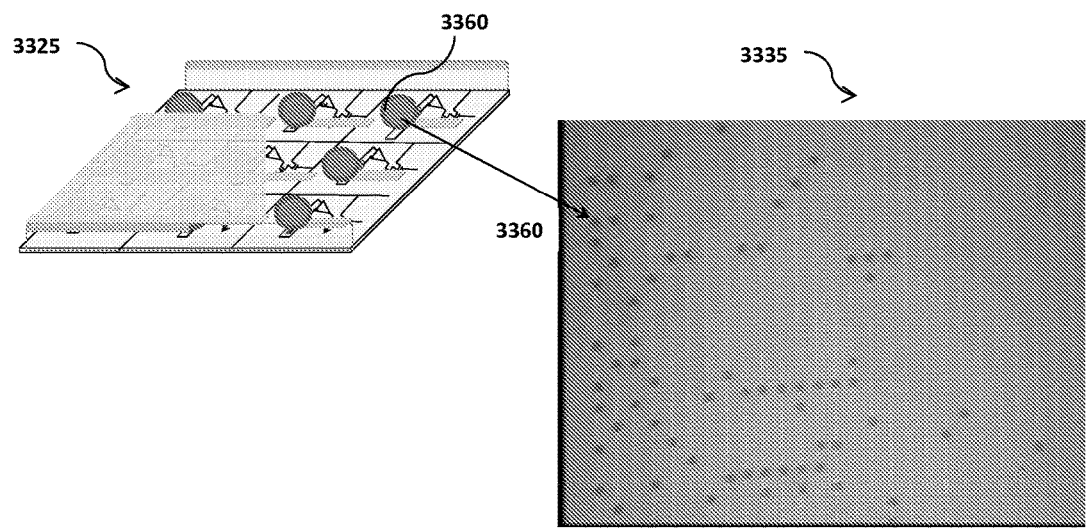
FIG. 33M schematically illustrates an example of a confinement cell array and corresponding image.

FIG. 33M shows a diagram of a confinement cell array 3325 and one embodiment of the corresponding proof of concept photo 3335. In some embodiments, magnetic beads 3360 are contained in an array, as seen in the proof of concept photo.

Figure 33N:
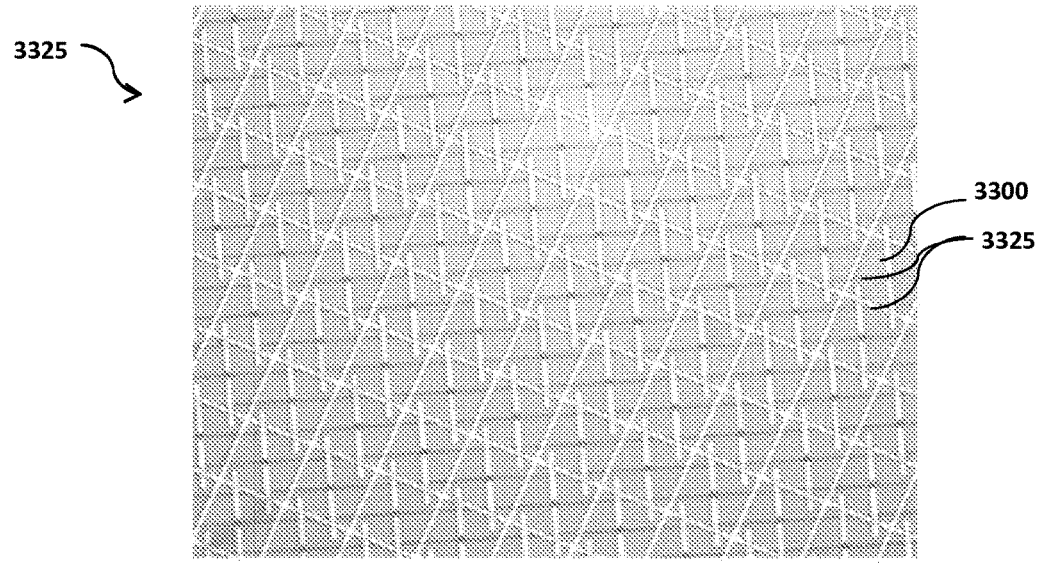
FIG. 33N shows an example of a confinement cell array arranged as part of a microfluidic chip.

FIG. 33N depicts, in a further embodiment, the confinement cell array 3325 arranged as part of a microfluidic chip for chamber-free amplification. This microfluidic chip configuration allows for the input and washing of reagents and target particles, such as DNA, nucleotides, primers, etc. for DNA amplification. The array density can be 30×30 or 100×100 or 1000×1000 or any other arrangement.

The methods described above can be utilized with a variety of DNA amplification methods, for example, Polymerase Chain Reaction (PCR) or isothermal amplification. Amplification may be solid phase amplification, wherein one primer is on the surface of the bead, and a second primer is in solution, or the amplification may be solid phase wherein all primers are on the bead. In an alternative embodiment, amplification may be performed whereby both primers are present in solution, and one primer, or both primers, are also present on the bead. After amplification has occurred, the electric field strength may be allowed to change in intensity or frequency, potentially being turned off.

Enrichment Module

When generating clonal beads a large percentage of the beads may have no DNA template. In addition, other beads may have poor amplification. These beads do not provide useful sequencing data so it may be desirable to remove these beads for better efficiency. In some embodiments, an enrichment module may be used that separates the beads with no or minimal amounts of template by using an electric field. Other enrichment or separation of the "null" beads from clonal beads via the charge, electrical or physical characteristics of the beads may be used.

Figure 34A:
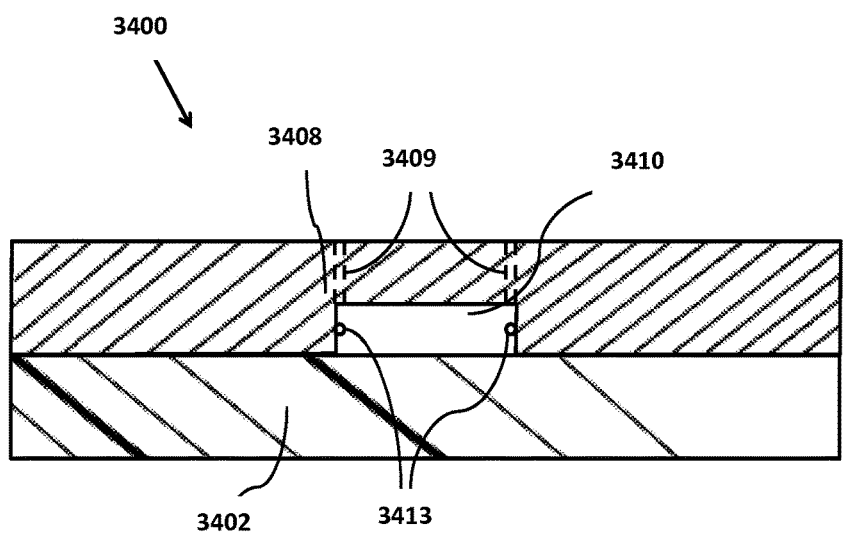
FIG. 34A schematically illustrates an example of a front view of an example module.
Figure 34B:
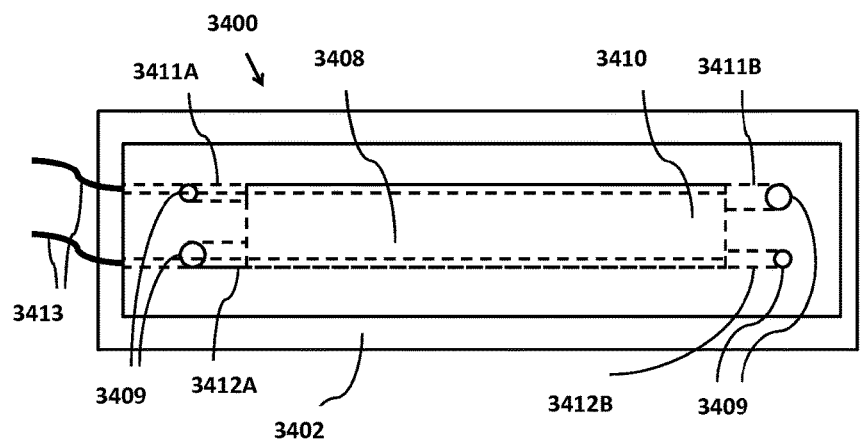
FIG. 34B schematically illustrates an example of a top view of an example module.

Beads fully loaded with templates have a higher charge, and so may move farther in an electric field than beads with only primers or a few templates or short or incomplete PCR products. In some embodiments, as shown in FIG. 34A (front view) and FIG. 34B (top view), this separation may be achieved through module 3400. A first fluidic input 3411A allows the injection of mixed beads. A second inlet 3412A allows the injection of a buffering solution without beads. A first outlet 3411B may be downstream from the second inlet 3412A. Fluids may be brought into or out of the module through ports 3409. The fluidic system may have a substrate 3402 and a channel 3410 formed in a layer of PDMS 3408 glass or other material.

The fluidic flow rates can be set by fluidic resistance or pumping speed such that more liquid flows in the second inlet. In one embodiment, the inlet and outlet widths may be varied to create different fluidic resistances, but other methods of modifying the fluidic resistances, such as different length or height are anticipated. Similarly, the fluidic resistance of the first outlet 3411B and second outlet 3412B can be modified so more liquid flows out of the first outlet 3411B. In such a setup, beads without a small velocity perpendicular to the flow may exit via the first outlet port 3411B. Additional output channels can be added to facilitate separation of beads with medium levels of template.

In one embodiment, for the separation of beads with different charge density, for example, due to different concentration or length of DNA molecules which are bound to or the surface charge of the beads, the beads may experience a different force in the electric field, and therefore a different velocity that is perpendicular or near perpendicular to the flow. In this type of configuration, beads with a smaller velocity perpendicular to the flow may exit via the first outlet port 3411B. The beads with higher charge and therefore increased perpendicular velocity to the flow may deflect more and exist from the other outlet port, resulting in the separation of the two beads types with different charge density. Similarly, additional output channels can be added to facilitate separation of beads with medium levels of template.

A pair of electrodes 3413 may be provided that enable generation of an electric field perpendicular to the fluid flow such that the template loaded beads migrate out of the flow path towards second outlet 3412B. Fluidic ports 3409 allow connection to the system plumbing.

Figure 34C:
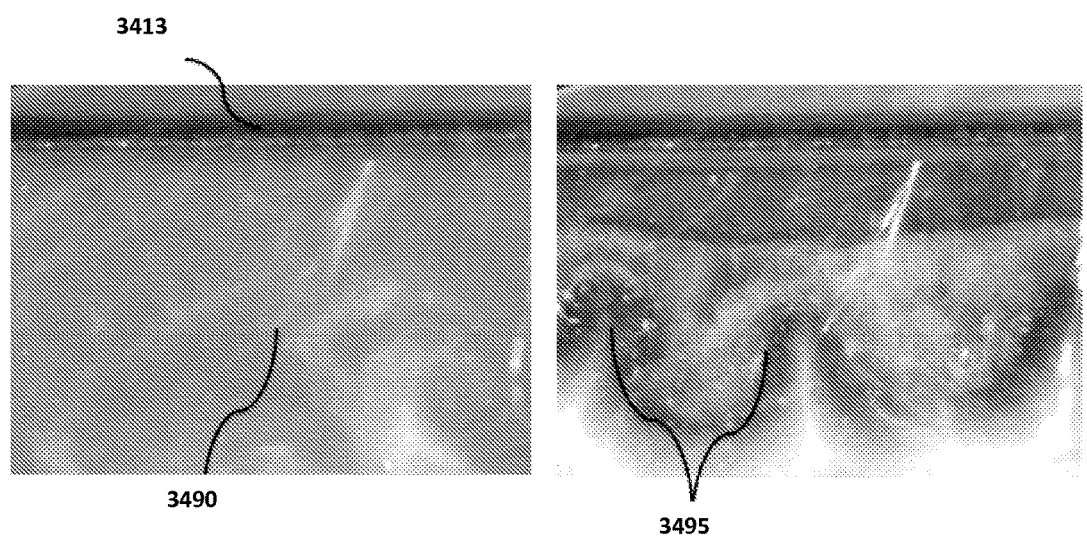
FIG. 34C shows an example of electro-osmotic flow.

One potential problem that may arise from the application of electrophoretic force (electric field) is electro-osmotic flow, as shown in FIG. 34C. When an electric field is applied to the microfluidic channel, electro-osmotic flow may occur due to the double layer that occurs at the interface of the solution with a wall of the microfluidic channel. This creates a movement of the fluidic medium 3490 of the microfluidic channel, but one problem that may arise is flow becoming circular or turbulent, as seen in a portion 3495 of fluidic medium 3490.

Figure 34D:
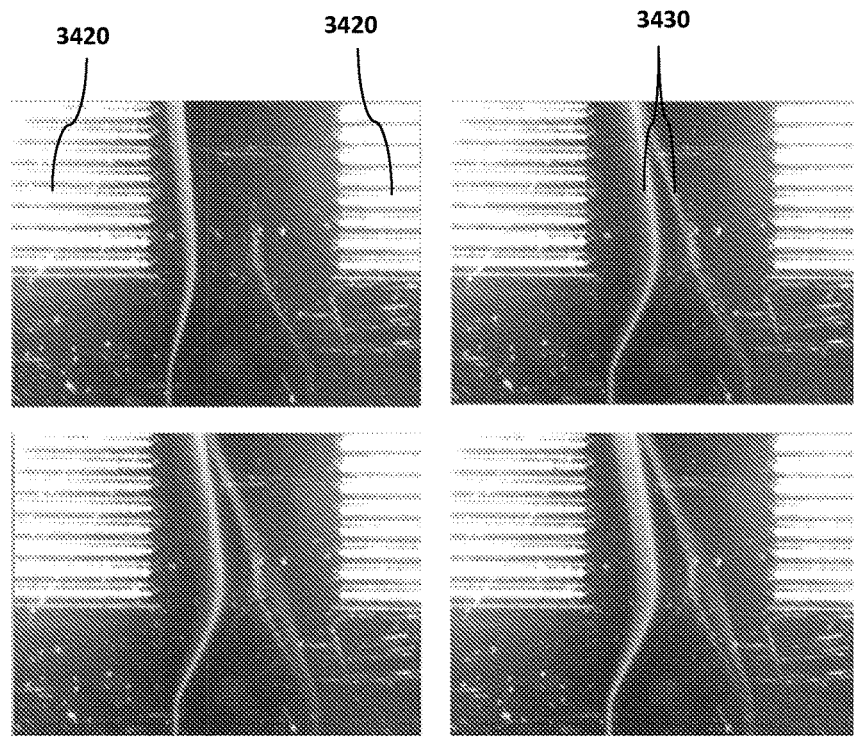
FIG. 34D shows an example of physical barriers for preventing the circular pattern that may be associated with electro-osmotic flow.

As shown in one embodiment in FIG. 34D, to prevent the circular pattern that may be associated with electro-osmotic flow, physical barriers in flow restraining sections 3420, such as micro-poles or walls, may be embedded in the microfluidic channel to help ensure that the flow remains linear. The figure illustrates the successful proof of concept and the progression of bead separation 3430 over time when an electric field is applied through the channel. This separation may be based on the charge density of the bead.

In another possible embodiment, the shape or structure of the electrodes may change in a manner such that the flow from the other section of the electrodes in the fluidic media cancels most of the electro-osmotic flow caused by one section. The shape of the electrodes, for example shapes such as triangles or saw tooth, or saw blades shapes or other shapes, can provide this property. In other embodiments, gel or other polymer materials may be used to reduce or prevent electro-osmotic flow.

Figure 34E:
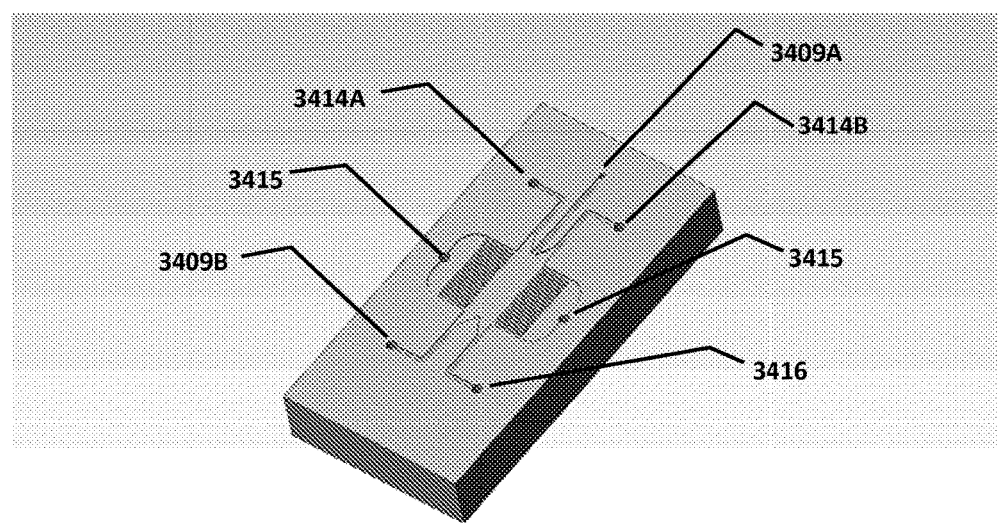
FIG. 34E schematically illustrates an example of an enrichment module as part of a chip.

In some embodiments, the enrichment module may be part of a chip, as shown in FIG. 34E, wherein there may be an inlet port 3409A, collection port 3409B, right buffer port 3414A, left buffer port 3414B, electrode reservoirs 3415, and a waste port 3416. The figure shows the channel side of flow through an enrichment module chip.

Improved Chemistry for Improved Detection

In general, for most clonal DNA sequencing systems, it is desirable to have as much DNA as possible on a surface, in order to maximize the amount of signal which may be obtained. In a sequencing by synthesis system where a change in charge or impedance resulting from nucleotide incorporation is being measured, for example, the more DNA that is present near the sensor, the more charge accumulates as a result of dNTP incorporation and the greater the resulting signal. The surface can be a sensor, a magnetic bead, or another carrier of any shape including planar, spherical, crystalline, etc. However, as the DNA is randomly placed on the surface, the spacing of the DNA may cause steric hindrance in a polymerization reaction. Steric hindrance occurs when the spatial properties of a molecule prevent or delay biochemical reactions occurring within or near the molecule. DNA and RNA polymerases vary noticeably in size, ranging from approximately 4 nm to 15 nm or more, and thus in order to optimize a given polymerization reaction, there must be adequate space for the polymerase activity. Here we present a novel method to provide such spacing.

In many different sequencing applications, target DNA or primers are bound to the surface of the substrate. These target molecules may be bound to the surface of the substrate in a variety of ways including covalent bonding or through linkers such as biotin-streptavidin, for example, where biotinylated DNA is bound to streptavidin coated beads. As a result of the attachment methods, the target DNA and primers are randomly placed on the surface, and may be in sufficiently close proximity that steric hindrance occurs for the polymerase extension. Even if a Biotin-Streptavidin bond is utilized, in case of high concentration of streptavidin on the bead, the size of the streptavidin (3 nm) is insufficient to properly space the DNA molecules such that there is room for the polymerase (7 to 10 nm).

In one embodiment, the target DNA may be appropriately spaced such that steric hindrance cannot occur. This may be achieved by, for example, using a complex with double stranded DNA and a polymerase which is larger than the polymerase which will be utilized for the sequencing reaction. In this manner, once the DNA is ready for sequencing, it will already be placed such that there is sufficient space for the polymerase used in sequencing to function properly. The initial polymerase can be one or more of BST, Phi29, Klenow exo-3', T4, etc. and the sequencing polymerase can be chosen such that it is a smaller size than the initial polymerase. The differences in size of the respective polymerase range from 1 nm to 10 nm.

Figure 35:
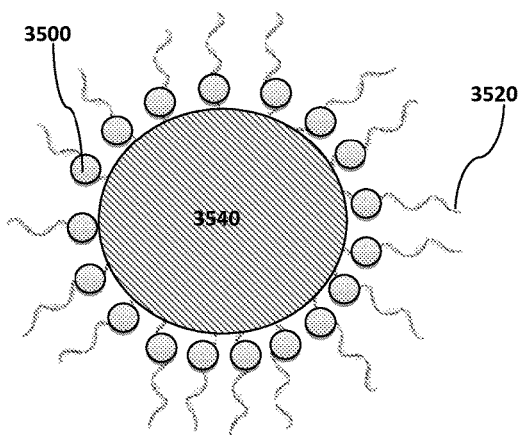
FIG. 35 schematically illustrates an example of proteins that bind DNA attached to a bead.

In an alternative embodiment, as shown in FIG. 35, other proteins 3500 that bind to double stranded or single stranded DNA 3520, which may be attached to a bead 3540, and are of appropriate size may be utilized. Such proteins can include, for example, Single-Strand DNA Binding proteins, transcription factors, etc.

The initial polymerase may be processive, so that it remains bound during the attachment process. Some examples include Bst and Phi29. After the attachment process occurs, the polymerase may be removed, degraded, or washed, leaving behind an appropriate amount of space for the sequencing reaction to occur. In an alternative embodiment, the polymerase may remain on the DNA, to be used as a spacer, and another polymerase may be used to sequence the DNA. In a further embodiment, the polymerase may be attached near the bead or carrier.

Alternatively, moieties other than proteins can be used to space out the DNA. These other moieties can then be removed, resulting in a DNA distribution that is designed to avoid steric hindrance.

In some embodiments, it may be desirable to use very low ionic strength reagents in order to maximize the Debye length. For such embodiments, it may be desirable to utilize reagents which have no more salt than is needed for the enzymatic reaction. For such reagents, it may be advantageous to minimize the amount of salt which is utilized, for example by reducing or minimizing the amount of NaCl or KCl which may be used, and using sufficient Mg. Sufficient Mg may include a concentration equal to the concentration of nucleotides used in the reagent, with additional Mg acting as a counter ion for the DNA, and the rest of the Mg for polymerase function in the flow cell that is associated with the DNA. Thus, the concentration needed will be a function of the amount and length of DNA in the flow cell, the number of polymerase molecules, nucleotide concentration, and the volume of reagent used.

In some embodiments wherein the ionic concentration is very low, the pH may be influenced by the surrounding air, for example, with $CO_2$ forming carbonic acid, which may reduce the pH. Buffering reagents contribute to the ionic concentration, so minimizing the amount of buffering may also be desired, depending on the method of detection. Mitigating the conflict between requiring sufficient buffering, yet having sufficiently low ionic strength may be accomplished by several possible embodiments. One embodiment involves using two buffers together. These buffers may be, for example, combined Tris and HEPES, as opposed to TRIS HCL, whereby both Tris and HEPES can contribute to buffering. In another embodiment, organic reagents that are miscible with water may be utilized, for example, alcohols such as ethanol.

In some embodiments, the charge associated with a bead may diminish the range of an electrical charge or conductivity sensor. The bead used may be M270, M280, dynal beads, etc. As a result, in some embodiments, it may be desirable to minimize the amount of charge present on the surface of the bead. This may be accomplished, for example, by changing the amount of $SO_4$ on the bead surface. In some embodies, it may be desirable to have a small amount of negative charge, which prevents DNA or nucleotides from binding to the surface of the bead, but not an excess amount of charge, which results in a significant reduction to the dynamic range of the sensor. An excess amount of negative charge will result in charge accumulation such that there is an increase in the number of counter ions associated with the bead and DNA, thus diminishing the sensitivity of the sensor.

Reducing Phasing Errors

When a polymerase is provided with a single nucleotide or nucleotide analog at a time, the error rate is typically significantly higher than when all four nucleotides or nucleotide analogs are provided, despite the enormous difference in the catalytic efficiency, measured as $k_{pol}/k_{d,app}$. This catalytic efficiency may be four logs or more lower for a mismatched nucleotide versus a matched nucleotide. Most of this is due to the difference in $K_{d,app}$. For example, Klenow polymerase has a misincorporation rate of one base in every $10^6$ to $10^8$ bases. In comparison, the polymerase extension reactions of current commercial systems that utilize the incorporation of single native dNTPs are limited to 100 to 1000 bases. The polymerase in these systems spends almost all of its time exposed to incorrect bases. Even when a nucleotide added to the system is the next nucleotide to be added, the reaction time must be long enough to complete the reaction for a homopolymer, which may be as long as eight or more nucleotides, or to complete the reaction with those DNA strands that are less accessible due to steric hindrance.

In some embodiments, the reaction can be made to be a competitive reaction by providing all four nucleotides or nucleotide analogs, wherein three of the four nucleotide or nucleotide analogs are unincorporable nucleotide analogs. As a result, the polymerase will spend most of its time futilely trying to correctly incorporate an unincorporable nucleotide. The unincorporable nucleotide may be a PNA nucleotide, a LNA nucleotide, adenine monophosphate, adenine diphosphate, adenosine, deoxyadenosine, guanine monophosphate, guanine diphosphateguanosine, deoxyguanosine, thymine monophosphate, thymine diphosphate5-Methluridine, thymidine, cytosine monophosphate, cytosine diphosphatecytodine, deoxycytodine, uracil monophosphate, uracil diphosphate, uridine, deoxyuridin, or other nucleotide analogs that may be bound, but not incorporated by a polymerase.

In one embodiment, the concentration levels of the different nucleotides or unincorporable nucleotide analogs may be matched to the relative polymerase activity for each of the nucleotide or nucleotide analogs. For example, the dTTP binding rate has been measured to be different by a factor of greater than two with respect to the other nucleotides. The other three nucleotides are much closer in their polymerase binding rates, but still vary by over 10 percent with respect to each other. It is likely that the difference may be even larger in comparing the polymerase binding rates for different unincorporable nucleotide analogs relative to native nucleotides.

In a further embodiment, the concentrations of the unincorporable nucleotides may be higher than the concentration for equivalent polymerase binding efficiency for the one or more incorporable nucleotide or nucleotide analog that is provided for a sequencing reaction. The probability of misincorporation of nucleotides or nucleotide analogs in this embodiment is lower than in an alternate approach of providing concentrations of unincorporable nucleotides such that polymerase binding rates are matched, or if the unincorporable nucleotide analogs are provided at concentrations with lower polymerase binding rates relative to the incorporable nucleotides or nucleotide analogs.

Alternatively, the unincorporable nucleotide analogs may be provided at concentrations with lower polymerase binding rates relative to the incorporable nucleotides or nucleotide analogs, such that the reaction may proceed at a higher rate than would occur if the polymerase binding rates of the unincorporable nucleotides were the same, or higher, than the incorporable nucleotide analog binding rates.

The above approach may be utilized for reaction conditions wherein there are three unincorporable nucleotide analogs and one incorporable nucleotide or nucleotide analog, or wherein there are two unincorporable nucleotide analogs, and two incorporable nucleotides or nucleotide analogs, or wherein there may be one unincorporable nucleotide analog, and three incorporable nucleotide or nucleotide analog.

Detection methods that may be utilized for the above reaction conditions, which use unincorporable nucleotide analogs, might include any form of electronic sensing of incorporation or incorporation events. For example, this electronic sensing method may include: ISFETs, CHEMFETs, NanoNeedles, NanoBridges, cantilever based sensors, electronic pH sensors, charge sensors chemilumenescence detection, fluorescence detection (including detection of Qdots or other nonstandard fluorophores), as well as detection of intercalating fluorophores, by use of fluogenic moieties.

Rephasing

Similarly, rephasing as described in provisional application U.S. 61/491,081 may be performed for any clonal sequencing system, including those which utilize four incorporable nucleotides, as well as all of those described above with respect to minimizing dephasing. As described in the previous application, leading or lagging sequence incorporation error may occur through incorrect additions of nucleotides or through missed additions of the correct nucleotides. This may occur because of non-optimal reaction conditions, steric hindrance, secondary structure, or other sources of polymerase inhibition. Several methods may be utilized for rephasing such as providing sequencing by incorporation nucleotides in different orders than might otherwise be done, using reversible terminator dNTPs, using a molecular "clamp", or any combination of these methods.

In some embodiments, in order to permit shorter hybridization probes, which may be utilized for rephasing, stabilizing compounds such as hydralazine or antitumor antibiotic cc-1065 may be utilized. Similarly, the probe may contain LNAs, PNAs, or other nucleoside analogs that increase the melting temperature of double stranded DNA. This probe may provide the dual function of allowing for tighter binding and precluding the need to prevent the probe from being extended by polymerase, for example, by using a terminator at the 3' end of the probe. The probe may act to block the incorporation reaction from occurring on the template DNA past a certain point. This allows for rephrasing such that lagging strands "catch up" and leading strands are temporarily blocked from proceeding with incorporation past the certain point where the probe is bound. Additionally, the probe may be a single plex, a duplex that may hybridize to the target DNA to create a more stable triplex, or a triplex that may hybridize with the target DNA to form a quadraplex.

Frequency-Dependent Oscillator

Figure 58:
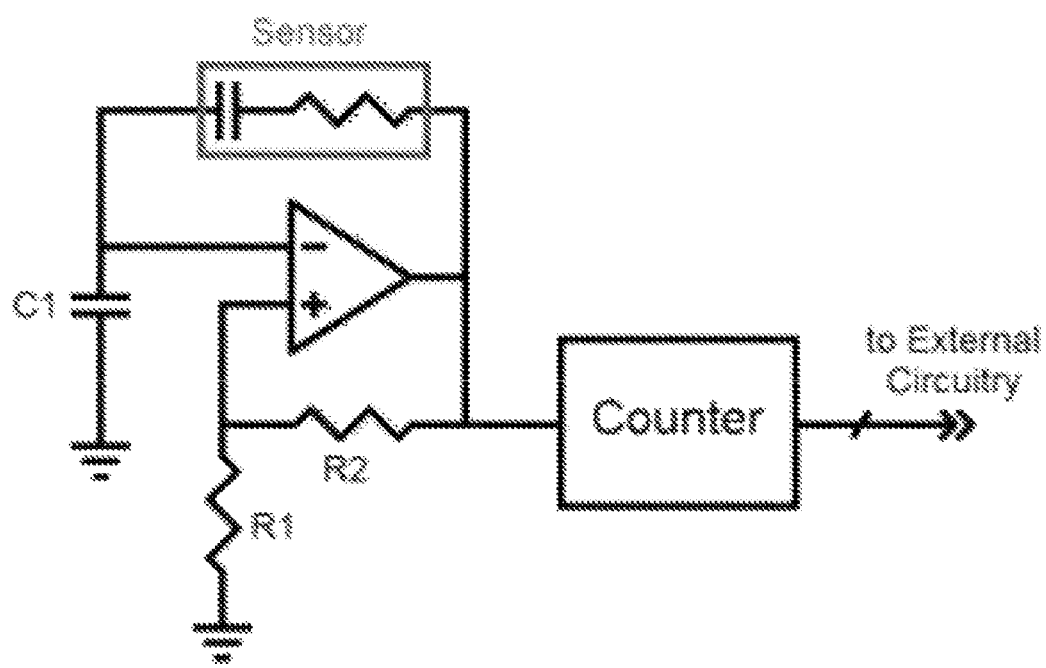

Both the NanoNeedle and the NanoBridge sensors require an accurate conductance measurement. In some embodiments, a relaxation oscillator circuit, as shown in FIG. 58, may be used to generate a clock signal with frequency proportional to the sensor conductance. This frequency may then be measured by counting the number of transitions within a defined period of time and this count will be proportional to the sensor conductance.

This approach has significant advantages over other measurement circuits that use a lock-in amplifier. The relaxation amplifier circuit does not require a large silicon area, as it lacks multipliers, analog to digital converters, and filter capacitors. Thus, it may be reasonably implemented on a small area of each pixel and in a high density array. Alternatively, input multiplexing may be used to reduce the number of circuits.

The nominal frequency may be adjusted by changing the capacitor (C1 in FIG. 58). A smaller capacitor may allow both a smaller area and a higher operating frequency for increased precision. Using a small capacitor can also reduce the ability of the NanoNeedle double-layer capacitor to contribute noise to the measurement, as its contribution to the impedance may be reduced. Increasing the number of counter bits may also allow for increased precision while requiring only a minor increase in area. If the result is known to fall within a relatively limited range, the number of counter bits may be reduced for a smaller circuit. The counter may then be free to roll over several times during a measurement and since the allowed range is known, these bits may not be necessary to deduce the true result. The number of bits need only be large enough to cover the range of conductance levels which may be expected.

The Schmidt circuit, a comparator with positive feedback, can be implemented using a two transistor differential pair amplifier. Better results, however, may likely be achieved using a CMOS differential amplifier with additional gain and output stages. The counter circuit may be implemented using comparatively small digital transistors. The counter may be synchronous, or it may be an asynchronous (ripple) counter to reduce transistor count. Thus, it may be implemented with only one flip-flop for each bit.

Despite some embodiments, data acquisition circuitry for the NanoNeedle may require a relatively large multiplier and A/D converter circuits. Two relaxation oscillators may allow for smaller silicon area requirements and improved high-frequency noise immunity. This approach may also be applicable to the NanoBridge, and it requires slight changes in the capacitor value and counter size, shown in FIG. 58. Different types of sensor and detector modalities can be used for the proposed embodiments.

The comparator output may be a square wave with frequency proportional to the sensor conductance. This frequency can be measured by counting the number of positive edges that occur during a fixed interval. Thus, the counter output may be proportional to the sensor conductance.

In one embodiment, C1 is made relatively small so that the voltage drop across C1 is larger than the voltage drop across the double-layer capacitor. This may also reduce the silicon area required for the cell. R1 and R2 can be used to adjust the nominal frequency and the peak-to-peak voltage on C1.

In some embodiments, if the counter is expected to stay within a desired range, the number of bits may be reduced and the counter may be allowed to reset several times before taking a reading. This will reduce the number of bits per counter, as well as the bus width of the multiplexer circuitry, thereby allowing for simpler circuitry to be implemented for a higher density array.

In another embodiment, if the circuitry is too large for a single cell, the circuit may be designed such that there exists a single counter and possibly comparator per row or per column, effectively moving the multiplexer between the sensors and the circuitry and effectively reducing the number of detection circuitry to the number of sensors in one column or one row.

The technique of detecting one row or one column at the time and therefore using one detection circuitry per column or per row can be applied to all embodiments listed in this disclosure and is not limited to just this embodiment.

In another embodiment, the analog circuitry could be accomplished using 2, 5, or 10, etc. transistors. The number of counter bits required may depend on the variation in bead loading and required sensing. Alternate configurations for circuit implementation may be possible, such as using 3 or 4 or other number of transistors.

Exemplary Sequencing System with Re-usable Magnetic Array and Nano-electronic Sensors In a sample embodiment, the exemplary sequencing system consists of fully-integrated DNA amplification and sequencing modules that utilize nano-magnetic-electronic platforms.

Figure 36A:
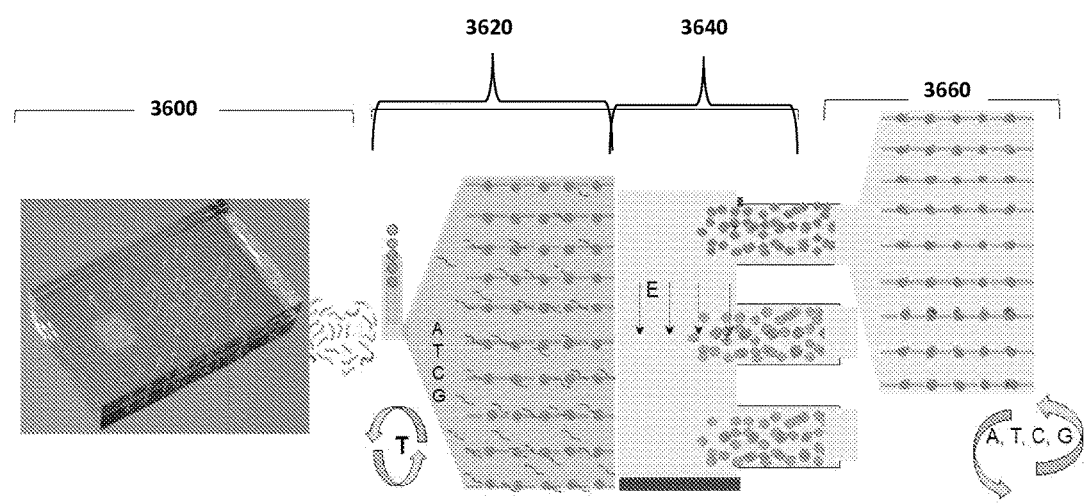
FIG. 36A schematically illustrates an example of an integrated sequencing platform.

FIG. 36A shows one embodiment of the exemplary system described below. FIG. 36A illustrates an integrated sequencing platform that may consist of a DNA library construction module 3600, an emulsion-free amplification module 3620, an electrophoretic enrichment module 3640, and a DNA sequencing module 3660.

Figure 36B:
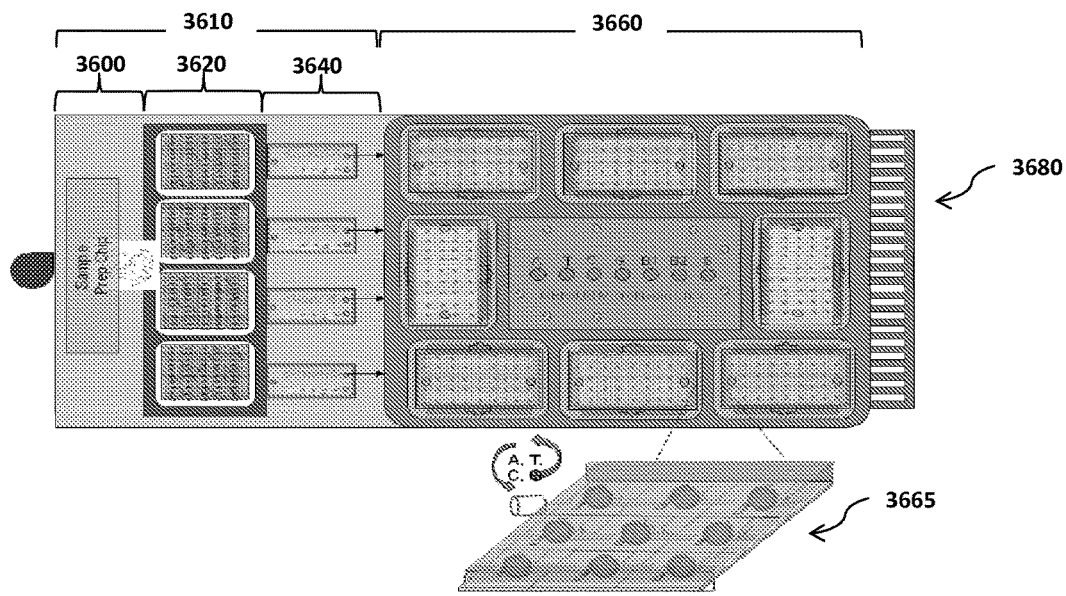
FIG. 36B schematically illustrates an example of a sample preparation module and DNA sequencing module integrated on a re-usable chip.

FIG. 36B shows some embodiment wherein a sample preparation module 3610 and the DNA sequencing module 3660 may be integrated on a re-usable magnetic-electronic chip 3680. Sample preparation 3610 may be comprised of DNA library construction module 3600, emulsion-free amplification module 3620, and electrophoretic enrichment module 3640. A close-up view 3665 of one embodiment of the sequencing array also illustrated in the figure.

In some embodiments, after amplification, the enrichment of DNA template-carrying monoclonal beads can be achieved through electrophoretic "sorting" based on DNA charge. Beads may then transferred and held using micromagnet bars integrated with a CMOS nano-electronic sequencing chip consisting of high-density arrays of sensors for electronic detection of DNA extension reactions.

Emulsion-Free Amplification

The system may use Chamber-free Nano-reactors (that can also be referred to as "confinement cells" or "virtual wells") created by an electric field containing and concentrating amplicons in close proximity to each bead, in order to provide an isolating barrier to adjacent reactions. The chip may consist of micro-magnetic components, each associated with a set of electrodes in an array, as shown in FIG. 33N. The combination of the micro-magnetic capture features with the electric field for DNA concentration and isolation may allow for more efficient amplification due to the localization and confinement of the amplicons.

Sample library DNA can be introduced and driven to the beads by an electric field, potentially increasing the efficiency of DNA library use and obviating the need for whole genome amplification. An electric field isolates adjacent virtual wells. The bead to library DNA molecule ratio can be approximately 1:1, resulting in mostly one template DNA per bead. An electric field can be utilized to concentrate the DNA amplicons in the vicinity of the beads. After amplification any null beads may be removed using electrophoretic separation. This separation process helps ensure that only beads with amplified DNA are transferred to the sequencing platform. This approach can be utilized in order to improve bead loading and reduce the amount of reagent needed.

Chamber-free Nano-reactors and Nano-electronic Sensors

In the exemplary embodiment, the sequencing platform can utilize the same microfluidic and nano-magnetic elements as described for the sample preparation and amplification modules. Nano-electronic sensors may be added in a 1:1 ratio (sensor to bead) to the magnetic array. This configuration can result in a high-density nano-electronic sensor array with nano-magnetic elements. The proof of concept for the exemplary embodiment of the chamber-free nano-reactor array is shown in FIG. 33M.

Furthermore, in the exemplary embodiment, the magnetic elements may allow for the capture of single beads for each CMOS-based, non-FET nano-electronic sensor. This configuration can allow for the elimination of wells or depressions, as shown in FIG. 3, which illustrates a confinement cell array without depressions or wells. In this manner, read lengths averaging over 1000 bases may be achieved. This may aid in the identification of haplotypes, copy number changes, and genomic rearrangements.

Figure 37:
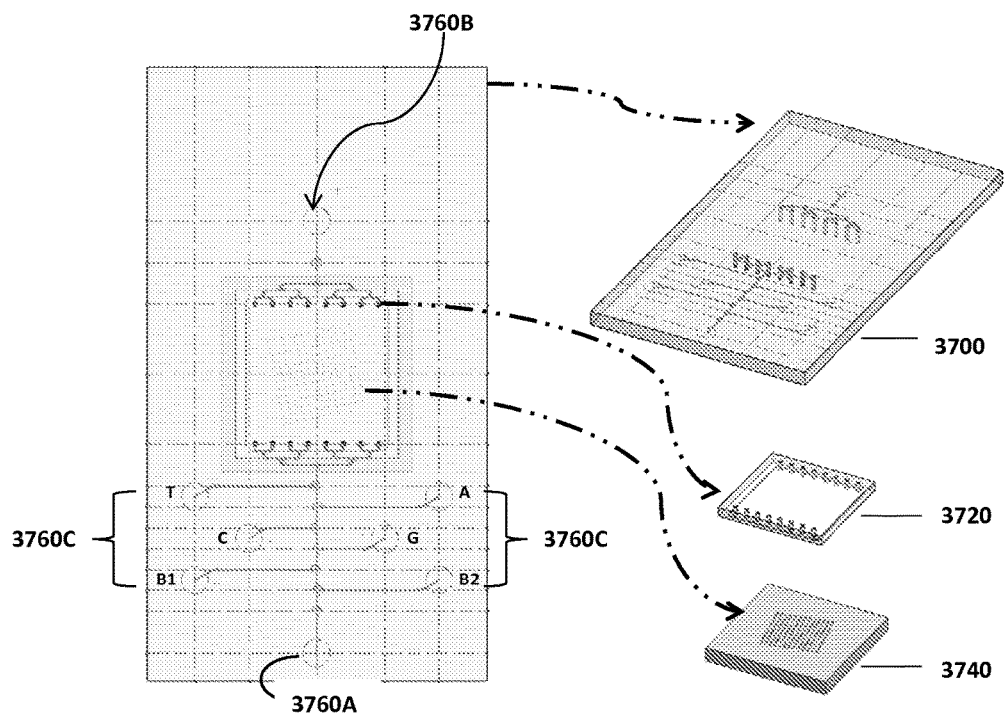
FIG. 37 schematically illustrates an example of a chamber-free approach combined with microfluidic controls.

The chamber-free approach may be combined with microfluidic controls, shown in FIG. 37. A microfluidic channel layer 3700 may be connected to a flow cell 3720 in order to allow for delivery of beads and their attached target molecules through input port 3760A. Microfluidic channel layer 3700 may also allow for the delivery of reagents, such as nucleotides (A, C, T, G) and/or buffers (B1, B2), through reagent ports 3760C. A detector chip 3740 may be connected to flow cell 3720 and microfluidic channel layer 3700 for the detection of a target reaction, which in the exemplary embodiment may be nucleotide incorporation for DNA sequencing. After the target reaction and detection is complete, waste may be removed through a waste port 3760B. This configuration may be used in order to achieve sharper reagent and wash transitions, faster cycle times, higher signal to noise ratios, lower volumes, less expensive reagent, and less expensive wash deliveries (due to the reduction in diffusion of DNA and reagents).

In the exemplary embodiment, the two types of electronic nano-sensors (NanoBridge and NanoNeedle) allow for the use of different detection modes: a) transient pH signal or b) steady state detection. The two detection mode signal outputs are compared in FIG. 16. If steady state measurement is utilized, two buffer conditions may be used, one optimized for incorporation, and one optimized for detection.

Chamber-free Nano-reactor Chip for Emulsion-free Template Amplification

Some of the most commonly used methods for generating samples for sequencing include at least one amplification step and one enrichment step to help ensure that sufficient template is available for the sequencing reaction. Emulsion PCR is widely used and the method can allow for trapping of single beads and template molecules with PCR reagents in a reverse emulsion. This method can be used to obtain clonally amplified templates.

This approach can be inefficient, however, as it may require large numbers of beads and PCR reagents. Emulsion PCR can also have significant variability in input DNA. Only when emulsion PCR droplets contain one bead with one DNA molecule can a useful clonal sequencing template be created. This method may result in a double Poisson distribution problem where fewer than $0.37^2$ of the beads will have usable template, potentially making this a costly step in the workflow. Furthermore, the formation of uniform droplets can be difficult to achieve and volume variability may limit the amount of PCR reagent. This may adversely affect the PCR efficiency, especially for amplification of longer templates. Limited droplet size can also increase the rate of base misincorporation if nucleotides become limiting. Lastly, the double Poisson distribution may be skewed such that a significant percentage of beads are multiclonal, decreasing sequencing throughput.

Figure 38A:
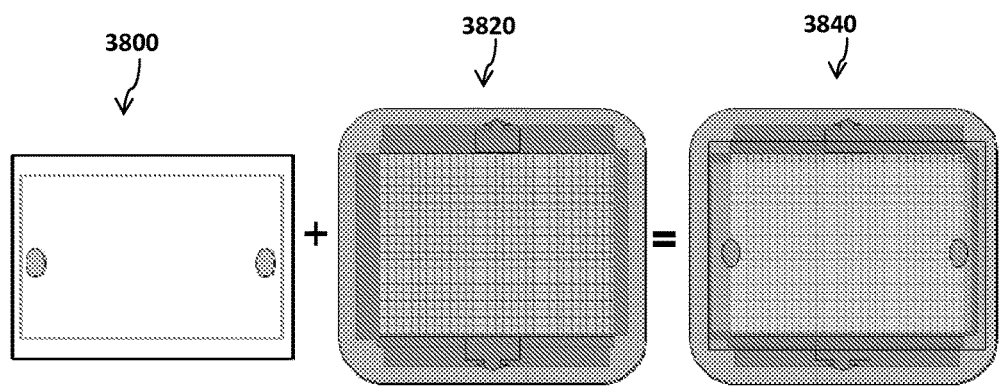
FIG. 38A schematically illustrates an example of a chamber-free nano-reactor chip.

In lieu of a reverse emulsion, the exemplary embodiment may utilize an emulsion-free, chip-based approach that can combine multiple sample processing steps into a single device. The purpose of the "Chamber-free Nano-reactor" chip, as shown in FIG. 38A in one embodiment, is to generate clonally amplified template on single beads arranged at high density on an array of micro-magnets. The amplification array chip 3820 can be embedded in a microfluidic channel chip 3800 to ensure fast and uniform reagent delivery to virtually all features. The combination of the amplification array chip 3820 and the microfluidic channel chip 3800 can allow for the creation of a chamber-free nano-reactor chip 3840.

Primer-functionalized magnetic beads may be loaded onto amplification array chip 3820 that may have millions of micro-magnetic fields for individual bead capture. A highly dilute DNA sequencing template may be added to create an optimal single template bead population using a modified Poisson distribution. DNA may then be amplified on the chip while an AC/DC electric field creates localized, chamber-free confinement cells. The applied electric field may allow for the concentration, confinement, and efficient capture of double stranded sequencing template DNA and amplification products on single beads. This approach may permit the elimination of whole genome amplification with its inherent bias. The configuration of the re-usable chamber-free nano-reactor chip 3840 can provide for control of bead numbers, DNA loading, and uniform reaction conditions across the entire chip. The device may eliminate the variability in reaction volumes and double Poisson distributions inherent in emulsion PCR.

Figure 38B:
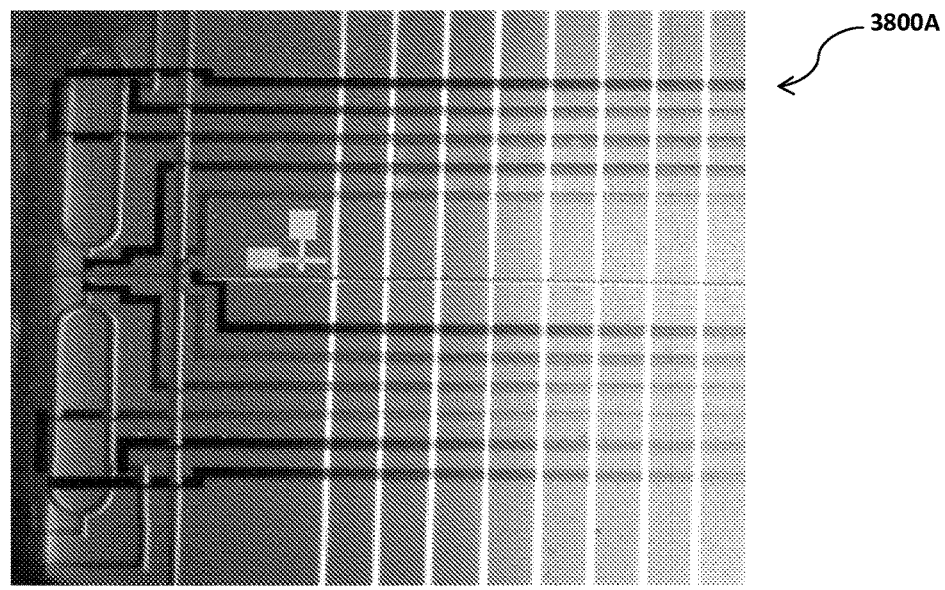
FIG. 38B shows an example of a microfluidic channel chip.
Figure 38C:
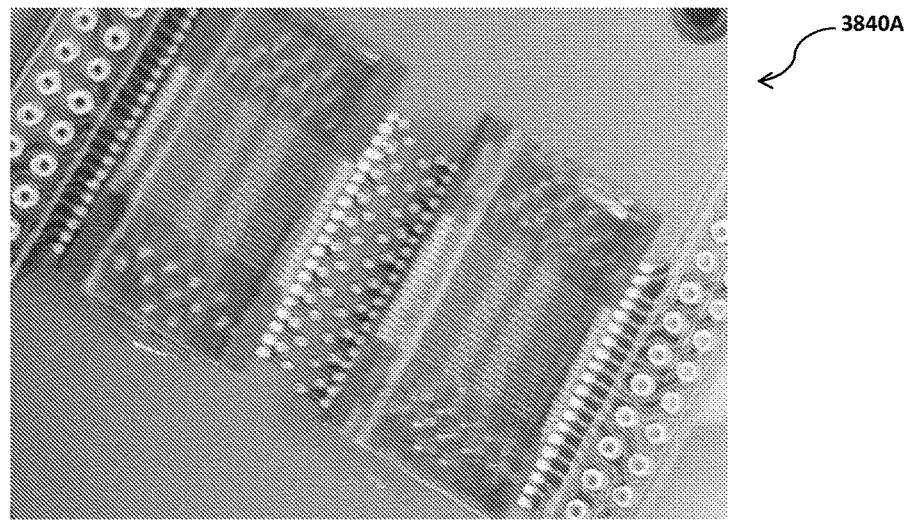
FIG. 38C shows an example of a chamber-free nano-reactor chip.

FIG. 38B shows an exemplary embodiment of a proof of concept photograph 3800A, of a close-up view of the microfluidic channel chip 3800. FIG. 38C shows a photograph of one embodiment of a prototype 3840A of a chamber-free nano-reactor chip 3840.

Figure 39:
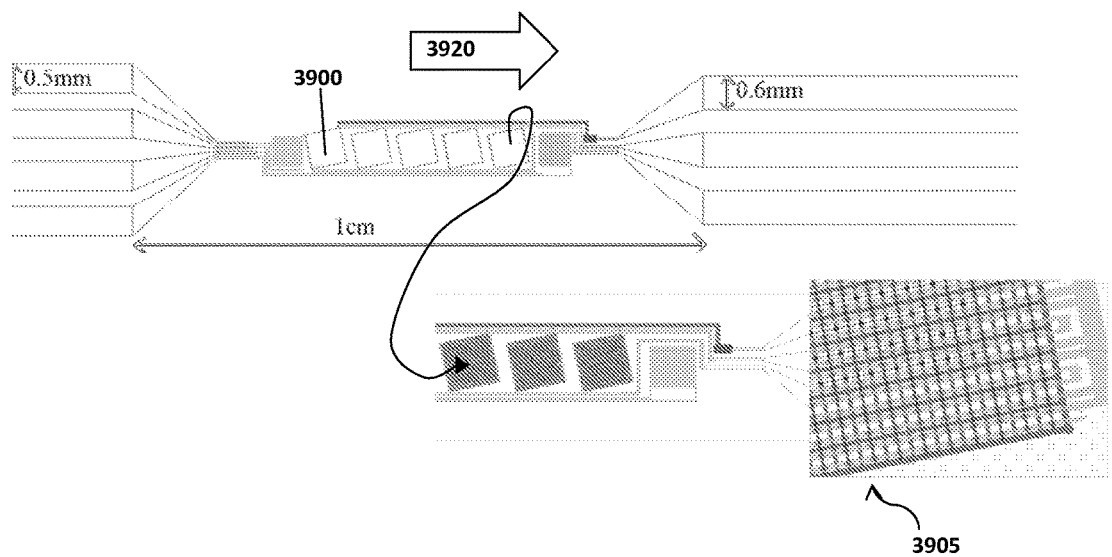
FIG. 39 schematically illustrates an example of a nanosensor array placed at an angle in comparison to the direction of flow.

In the exemplary embodiment, as shown in FIG. 39, nanosensor array 3900 may be placed at 11 degrees in comparison to the direction of the flow 3920. A close up view 3905 of nanosensor array 3900 is illustrated. Varying the angle of the array placement with respect to flow may allow for optimization of bead loading and reagent distribution. Furthermore, in the exemplary embodiment, the rows of pixels closest to the edge of the array may not have magnets in order to minimize contamination.

In the exemplary embodiment, the magnetic array can be laid out on a wafer and contain two metal electrodes located underneath and around each of the micro-magnet bead capture pixels. The chamber-free nano-reactor chip can have a multiplicity of the virtual reaction locations (with single beads) in which reactants, such as DNA polymerase, primers, and products, such as for example amplicons, can be contained and isolated from other chamber-free nano-reactors.

a) Fabrication of the Micro-magnet Array with Local Electrodes

In the exemplary embodiment, the fabrication of re-usable magnetic arrays may utilize thin film permanent magnetic bars for the capture of paramagnetic beads. These arrays can provide densities greater than $10^4$ beads/cm$^2$ to approximately $5 \times 10^8$ beads/cm$^2$ and may be integrated with microfluidics for reagent delivery and easy capture/removal of magnetic beads. One important feature may be a staggered micro-magnet arrangement that can be helpful in allowing efficient bead capture under laminar flow conditions. In the exemplary embodiment, magnetic structures may be fabricated by ArcNano (Advanced Research Corporation, White Bear Lake, Minn.) on a 100 mm silicon oxide wafer using Cobalt-Chromium-Platinum with bar sizes ranging from 10×1 to 10×2 µm in 0.25 µm (1, 1.25, 1.5, 2.0, etc.) increments with gap sizes ranging from 1.25-2.5 µm (0.25

μm increments) or 20×1 μm to 20×2 μm with gap sizes ranging from 1.25 to 3.5 μm (0.25 or 0.5 μm increments) and a bead to bead distance of 26.8 μm. In some embodiments, bead sizes may range from 1-6 μm. In a further embodiment, configurations of 4×4 micro-magnet arrays per channel, each with 30×30 features, can be utilized.

Figure 40:
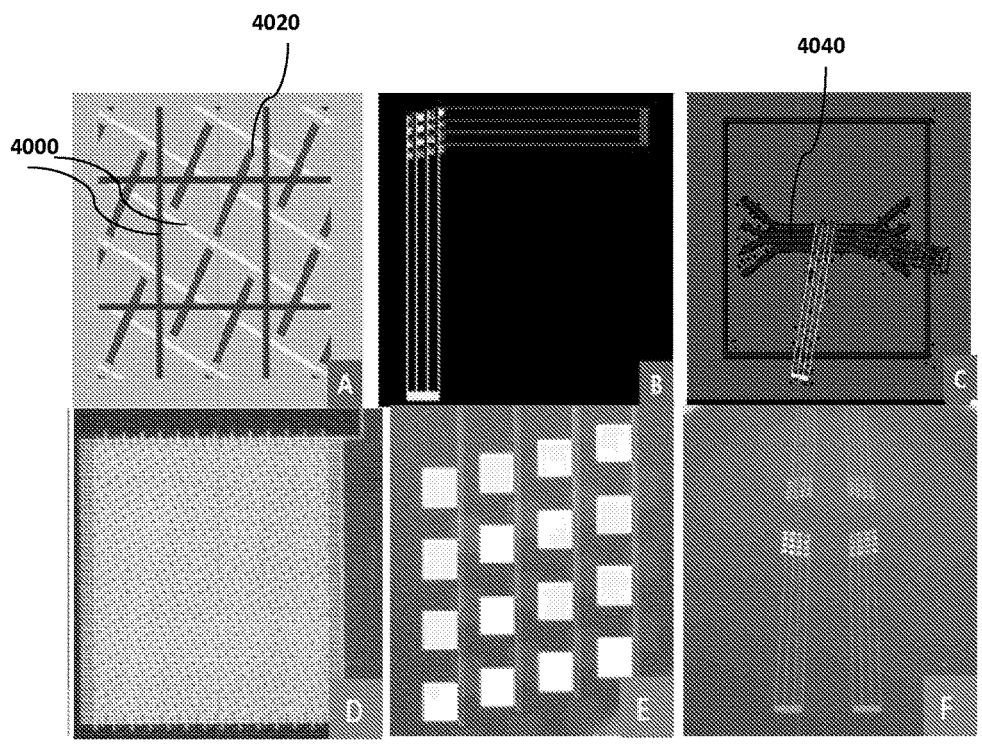
FIG. 40 illustrates an example of a mask layout for the micro-magnetic array with electrodes.

In addition, each micro-magnetic feature can be combined with 2 metal electrodes, arranged in such a manner as to create an electric field around the bead in order to concentrate the negatively charged DNA amplicons in close proximity to the bead surface and disperse (but may hold) negatively charged dNTPs and other light ions in the chamber-free nano-reactor. In the exemplary embodiment, the structure can be fabricated as follows: Layer 1: 1 μm uniform Thermal Oxide (provided with wafer), Layer 2: 50 nm patterned Metal Electrode grid and 50 nm patterned Oxide to electrically isolate the metal layer from the remaining surface, Layer 3: 115 nm Magnetic Poly-Layer, Layer 4: 200 nm Oxide, Layer 5: 50 nm Metal Electrode grid to create the electric field boundaries of the nano-reactors. FIG. 40 illustrates the mask layout of the micro-magnetic array with electrodes. FIG. 40A represents the mask layout, wherein the electrodes 4000 and magnetic elements 4020 may be fabricated in a 30×30 pixel arrangement. FIG. 40B shows a 4×4 array of a 30×30 pixel layout. FIG. 40C shows PDMS channels 4040 over a 4×4 and 30×30 pixel array. FIGS. 40D-E show the fabricated micro-magnet array with electrodes. FIG. F shows the pixel array in another orientation.

b) Microfluidic Channels and Reagent Delivery

All functional elements may be embedded in a 800 μm×20 μm single channel and visualization can be done using a fluorescent microscope. Flow conditions can be critical for the functionality of the chamber-free nano-reactor chip as they may influence the efficiency of bead capture, reagent delivery, and bead removal for re-usability. PDMS can have the advantage of rapid prototyping. Through replica molding, channels with feature sizes down to submicron dimensions can be made rapidly, with high fidelity, and this may allow for quick exploration of a large number of parameters. PDMS also has excellent optical properties when compared to other plastic materials such as PMMA, COC, and PC and exhibits minimal auto-fluorescence and absorption between 290-1100 nm, allowing for sensitive detection of fluorescent molecules.

The elastic nature of PDMS may also allow for fabrication of highly dense integrated valves that can be placed directly adjacent to reagent channels, and this may result in a decrease in dead volume. In the exemplary embodiment, fluidics may be driven by a syringe pump with 6 selector valves capable of varying flow rates from 0.02 to 10 μl/min to allow for accurate reagent delivery rates.

c) Bead Capture, Wash and Release

Figure 41:
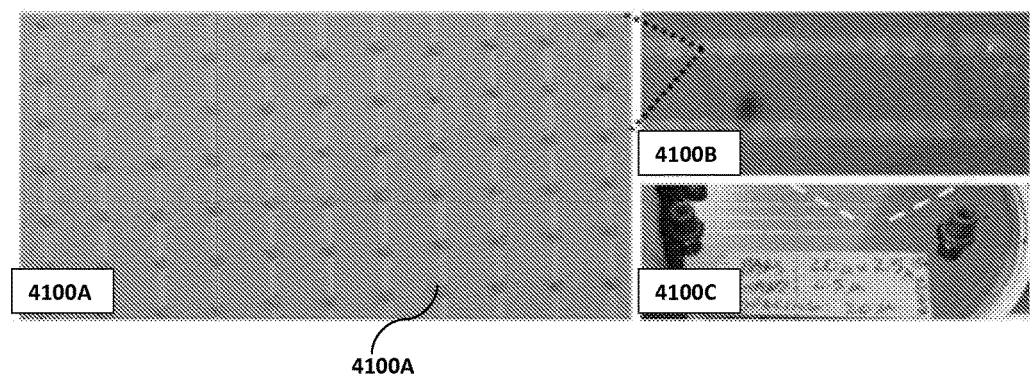
FIG. 41 shows an example of a micro-magnetic array with captured beads.

The method described above can allow for the efficient capture of single beads with a high fill rate (>90%), absence of bead relocation, and a 100% wash out for chip re-usability. The micro-magnetic feature size and magnetic properties may be linked to and may need to be matched with the bead properties to allow for efficient capture and removal under useful reagent flow rates. FIG. 41 shows photograph of a micro-magnetic array 4100A with captured paramagnetic Dynal beads 4120. Magnified views 4100B and 4100C of micro-magnetic array 4100A are shown, wherein the magnified views are at different levels of magnification and there are two channels each with 10 arrays of 30×30 pixels.

Figure 42:
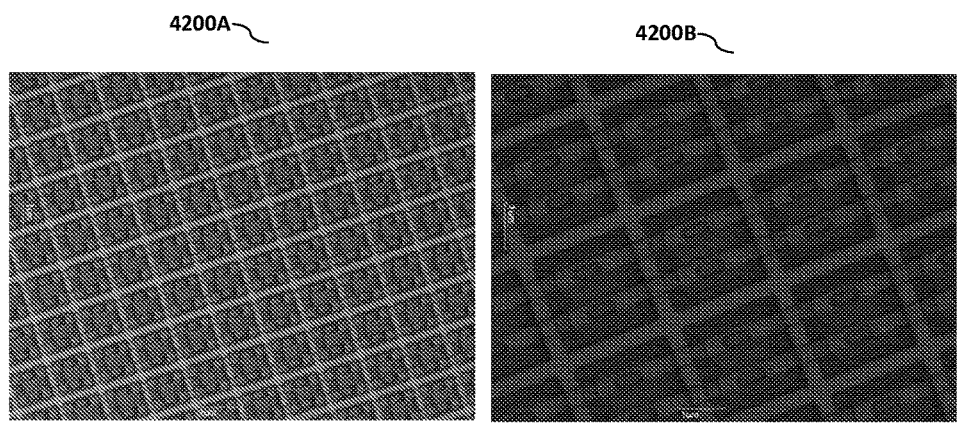
FIG. 42 shows an example of data from cells of the magnetic array with differing pitch size.

In the sample embodiment, a magnetic array consisting of 2×20 μm bars and a gap size of 2 μm can capture single 4.5 μm beads using flow rates between 0.02 and 0.45 μl/min in a 800×15 μm channel. Bead removal may be complete at a flow rate of <3 μl/min. With a single inlet port there may be flow constraints towards the outside edges of the channel. Paramagnetic beads of 1.0, 2.8 or 4.5 μm may be used. FIG. 42 shows two embodiments of experimental data wherein the pitch size of the cells of magnetic array 4200A is 12 μm and the pitch size of the cells of magnetic array 4200B is 20 μm.

d) Demonstration of on Chip Amplification:

The efficient amplification of a single template (clone) on single beads in the wafer can be critical for the generation of sufficient template captured on the bead surface to allow for subsequent enrichment and sequencing. In the sample embodiment, a machined metal adapter fitted to a commercial thermocycler for PCR cycling may be used. Using this configuration, the heat transfer to the wafer may be significantly slower than the heat transfer for thin-walled PCR tubes and the cycling conditions may be adjusted accordingly. Amplification of DNA template, ranging from 0-100 copies, may be performed on the chip, and amplification efficiency can be tested using quantitative PCR (qPCR). In some embodiments, a single channel can ultimately deliver reagents to about $5 \times 10^6$ beads of which 20% may be clonal beads, permitting the sharing of small ions such as Mg2+ and dNTPs, thereby reducing the needed concentrations.

After amplification conditions have been established and the optimal micro-magnet-bead configuration has been determined, DNA carrying beads (calibrated to various starting concentrations) may be captured on the chip by the micro-magnets. Amplification reagents can then be introduced uniformly into the chip and cycling may be performed. qPCR may be used to quantify the amount of amplicon produced. A nominal concentration may be used, for example greater than $10^5$ DNA copies/bead, and may be utilized to allow for downstream nano-sensor electronic sequencing signal detection on single beads. In an alternative embodiment, isothermal amplification can be used.

e) Electric Field Mediated Concentration and Confinement of Amplification Products In the sample embodiment, in order to capture template DNA and amplification products on a single bead, a three dimensional electric 'cage' may be created using an electric field density profile that is balanced but asymmetric. AC waveforms can induce drift of charged molecules.

Figure 43A:
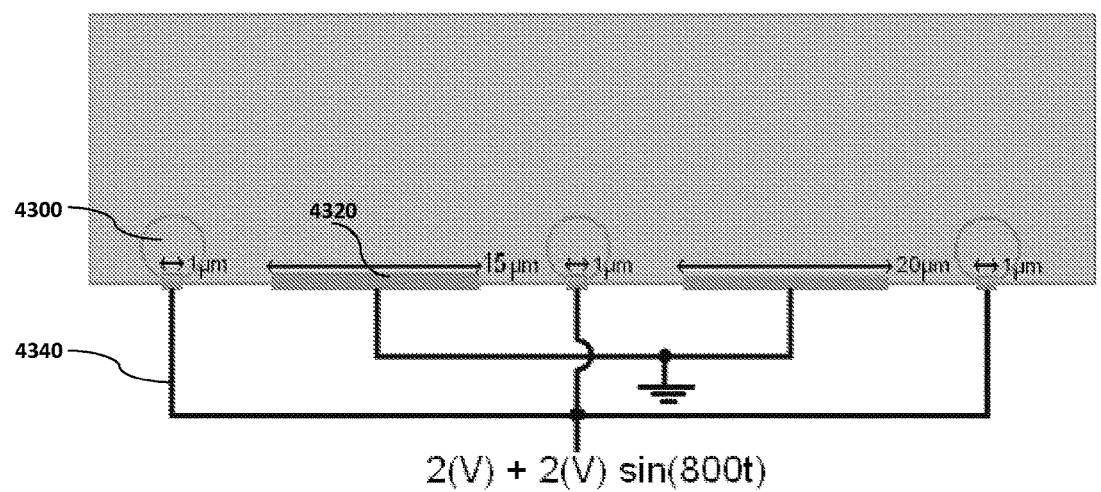
FIG. 43A schematically illustrates a side view of an example of beads and electrodes.
Figure 43B:
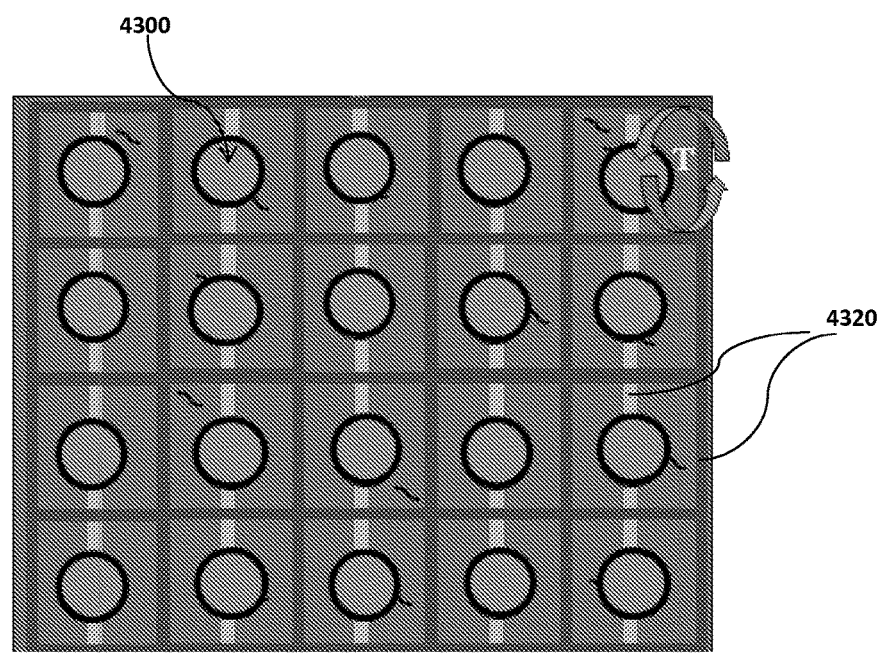
FIG. 43B schematically illustrates a top view of an example of an array configuration.

In the exemplary embodiment, in FIG. 34A, a side view of one configuration of the beads 4300 and electrodes 4320, as well as the path of the current 4340, is shown. A top view of another configuration of the electrode 4320 and bead 4300 layout is shown in FIG. 43B, as a top view of an array configuration.

The structure may be composed of a micro-fluidic channel with several conductive electrodes fabricated on the bottom of the channel for concentrating and isolating negatively charged amplicons.

In the exemplary embodiment, single beads can be captured on top of the 1 μm electrodes that may be connected to an AC voltage with a DC offset. The electrodes at the perimeter of the confinement cell may be negatively biased with respect to the bead electrode to prevent diffusion of the negatively charged DNA amplicon. In the exemplary embodiment, the distance from one bead to the next is 26.8 μm and the height of the channel is assumed to be 20 μm (by 800 μm wide).

Figure 44A:
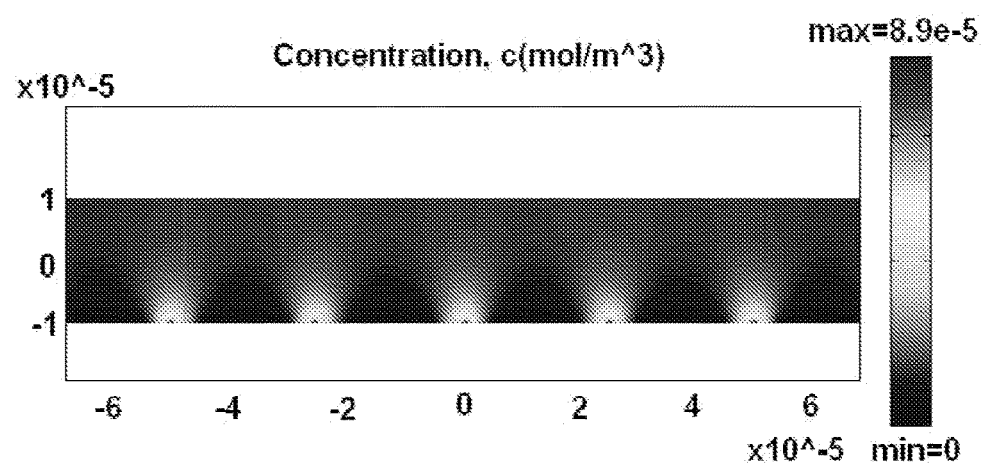
FIG. 44A shows an example of a two-dimensional concentration profile of DNA molecules.
Figure 44B:
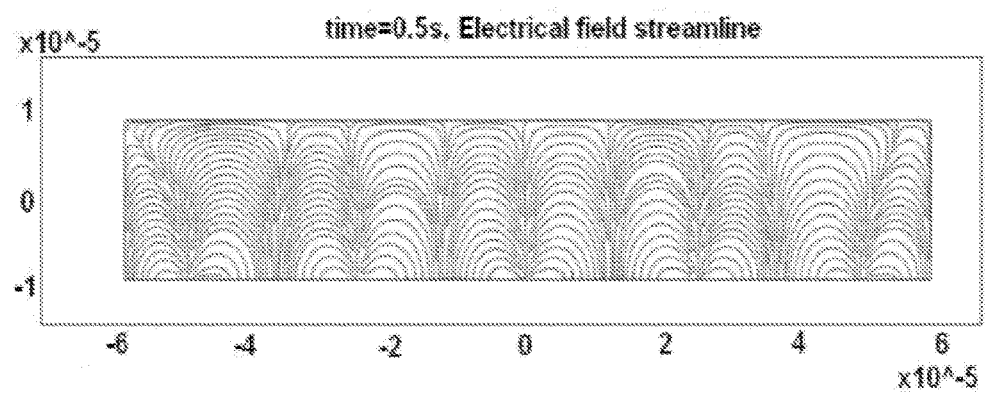
FIG. 44B shows an example of corresponding electric field streamline.
Figure 44C:
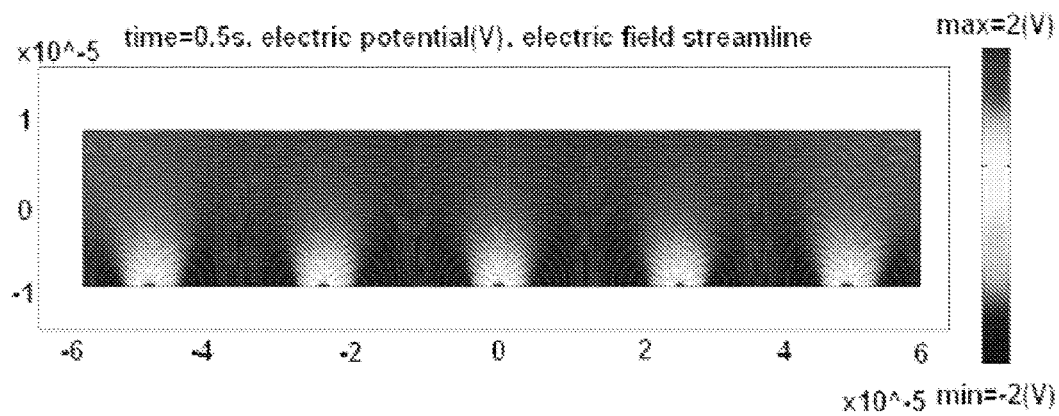
FIG. 44C shows an example overlay of the concentration of DNA molecules and electric field streamline.
Figure 44D:
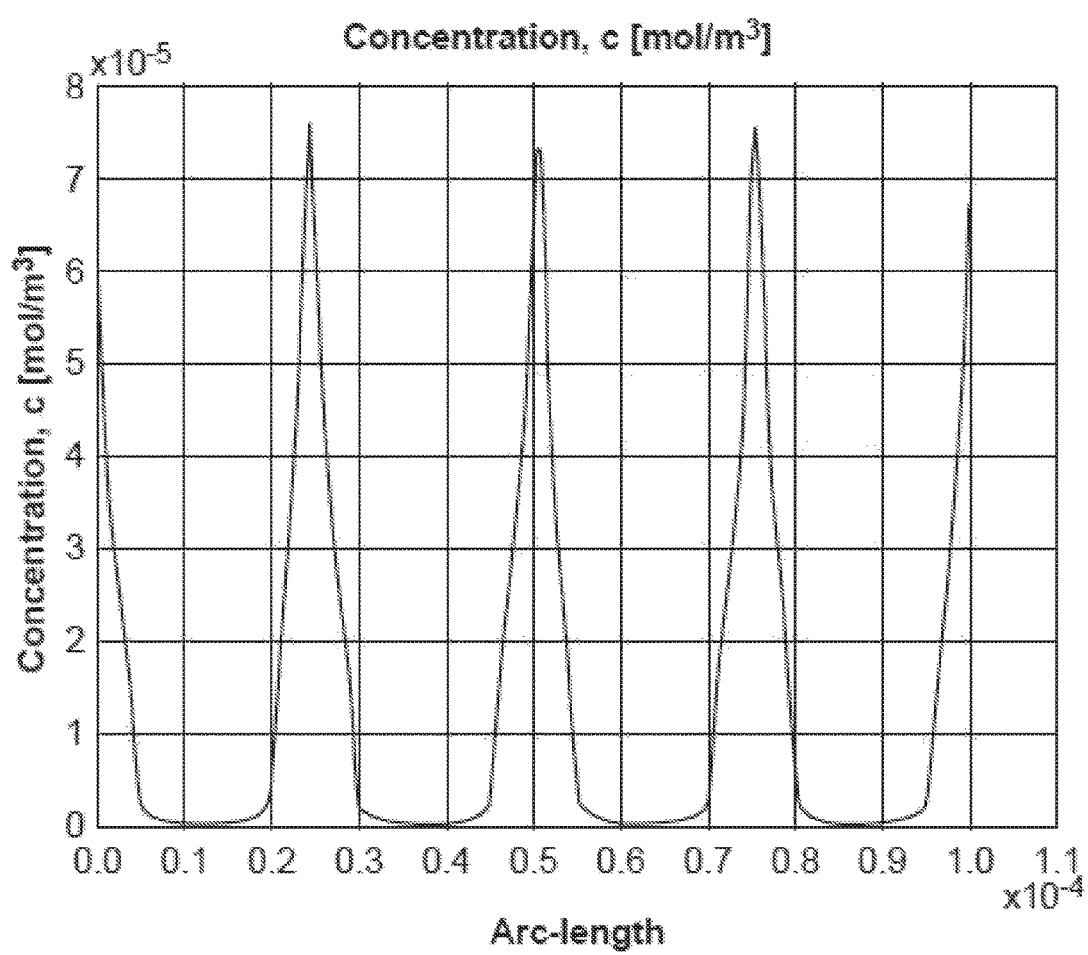
FIG. 44D shows an example of a two-dimensional profile illustrating DNA concentration.

In the exemplary embodiment, a numerical simulation of applying an electric field to the electrode grids in the microfluidic channel was performed. This results in the formation of the chamber-free nano-reactor. FIG. 44A shows a two dimensional concentration profile of DNA molecules. FIG. 44B shows the corresponding electric field streamline. FIG. 44C shows the overlay between the FIGS. 44A and 44B. FIG. 44D shows a two dimensional profile illustrating DNA concentration that may result from the application of an electric field. The starting condition can be a unified DNA concentration in a defined volume.

A numerical simulation of the exemplary embodiment was performed (using COMSOL) with the following parameters: Concentration of DNA in channel: 10e-6 M (uniform); DNA: 500 bases; Diffusion Coefficient of DNA: 5.6e-12 $m^2$/s; Mobility of DNA at 298'K: 2.2e-15 mol*s/kg (mobility=diffusion coefficient/(8.31 (J/Kmole)×T ('K))); Viscosity of solution: 1.5×10e-3 Ns/m2; Density of solution: 10e3 kg/m3; Conductivity of solution (50 mM KCl): 0.7 Ohm/m.

In the exemplary embodiment, solutions with differing DNA concentrations and sizes, similar to those expected from a fragment library and on chip amplification, may be introduced into the chip via the microfluidic channel. This may be followed by application of DC voltages ranging from 0.5-3.0V and AC amplitudes of 1-4V with frequencies ranging from 200-300 Hz. In order to initiate amplification of clonal DNA and enrichment on the magnetic beads, single DNA molecule carrying beads can be introduced. In addition, on-bead concentration can be monitored using elution and quantitative PCR. The electric field defined chamber-free nano-reactors can contain DNA locally and prevent diffusion to neighboring pixels with 99%, or greater, efficiency.

f) Electric Field Based Bead Sorter for Enrichment of Template Beads

In the exemplary embodiment, the 'bead sorter' may allow for efficient enrichment of amplicon carrying beads through a short channel using electrophoresis. Negatively charged DNA beads may be diverted preferentially and efficiently into a collection chamber and subsequently loaded onto the nano-sensor DNA sequencing chip. In one embodiment, the separation of beads with different charge density, for example, may occur due to different concentrations or lengths of DNA molecules, which may be bound to the beads, or it may occur due to the surface charge of the beads. The beads may experience a different force in the electric field and therefore a different velocity that is perpendicular to the flow. This causes beads with DNA to exit at a different outlet port location from reject (null) beads.

Figure 45:
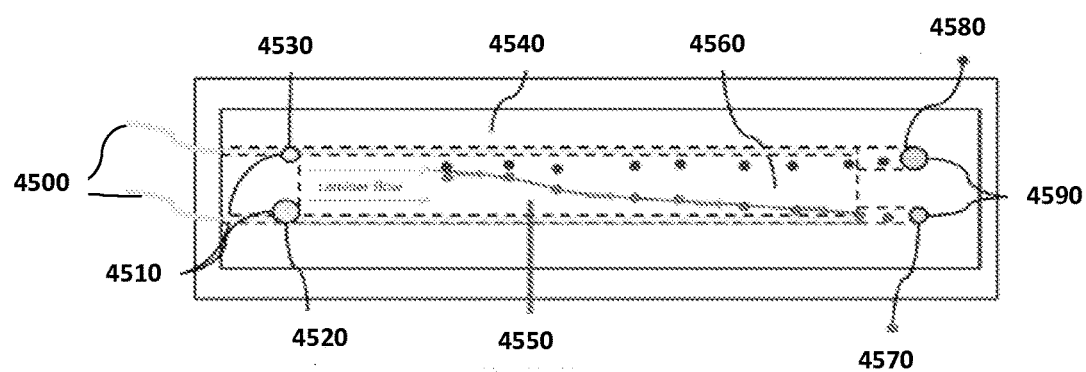
FIG. 45 schematically illustrates an example of a bead separation module.

Charge and electric field based separation of amplicon-positive and primer-only DNA beads using electrophoresis is shown in an exemplary embodiment in FIG. 45, as illustrated by a schematic of a bead separation module. A pair of electrodes 4500 supported by a channel structure 4540 may enable the generation of an electric field force 4550 perpendicular to fluid flow in the separation channel 4560 such that sequencing beads 4570, loaded with template, migrate out of the flow path towards the appropriate outlet port 4590. The reject beads 4580 also exit out of an outlet port 4590, but it is a different outlet port, designed to allow for removal of reject beads 4580. Beads and reagents enter separation channel 4560 through inlet ports 4510. More specifically, beads enter separation channel 4560 through a bead input 4530 and buffer may enter through a buffer input 4520.

In the sample embodiment, the enrichment channel has an active area length of 6 mm and width of 1 mm. The input channels are 200 and 400 μm wide and 0.075 mm high. Voltage can be applied across the 1 mm gap and may be 5-10 VDC. The fluid flow rate can be controlled by the channel widths and may be pressure driven, using the same pressure source.

Figure 46A:
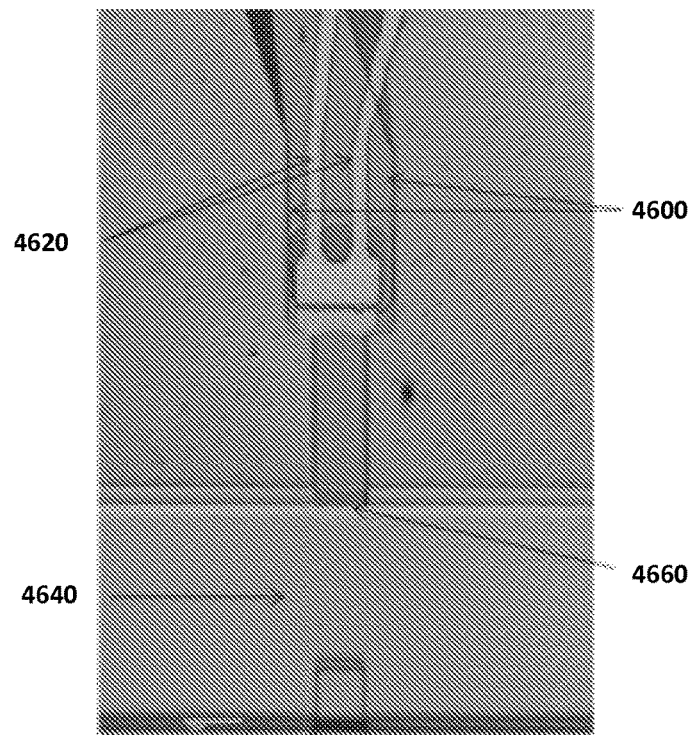
FIG. 46A shows a top view photomicrograph of an example of a NanoNeedle sensor.
Figure 46B:
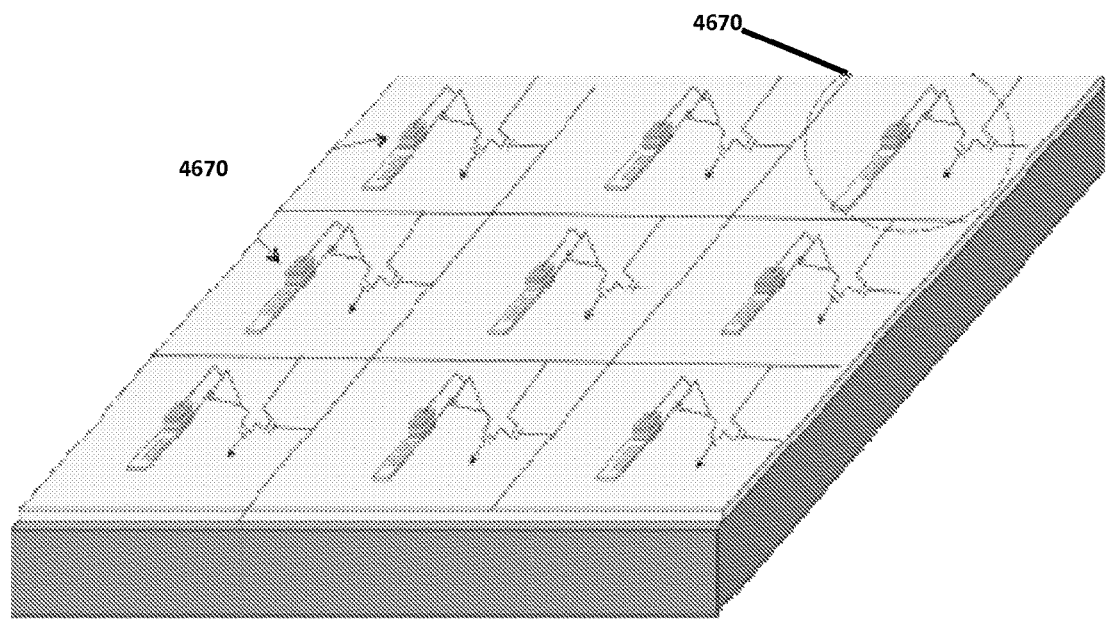
FIG. 46B schematically illustrates an example of a two-dimensional NanoNeedle array.
Figure 46C:
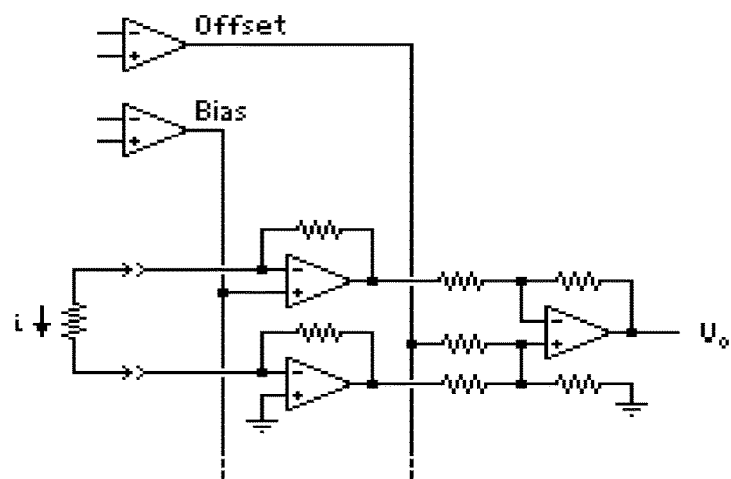
FIG. 46C schematically illustrates the corresponding circuit of the example NanoNeedle shown in FIG. 46B.

Re-usable Sequencing Chip with Electronic Nano-sensors and Micro-magnetic Capture Arrays Electrical nano-sensors can rely on label free detection of biochemical reactions that produce changes in charge and current. In one version of the sample embodiment, a NanoNeedle is used. The NanoNeedle is an ultra-sensitive, localized impedance biosensor that can allow the detection of changes in impedance via electrical current changes that occur following perturbation of the local solution resistance through, for example, proton release during the DNA incorporation reaction, protein binding, DNA hybridization, pH change, or other biochemical reactions. FIG. 46A shows a top view photomicrograph of one embodiment of the NanoNeedle sensor. A passive insulator 4600 surrounds the NanoNeedle, allowing for detection of a target reaction, such as nucleotide incorporation, via conductive electrodes 4620. The target reaction may occur in a fluidic channel 4640 and an electric field 4660 may be generated in order to concentrate target molecules in a desired area. FIG. 46B shows a schematic of a two dimensional NanoNeedle 4670 array and the corresponding circuit of the two dimensional NanoNeedle array is shown in FIG. 46C.

In the exemplary embodiment, the increased sensitivity of the NanoNeedle sensor can be achieved through its geometry, with the active (20 nm) double electrode tip in immediate contact with the reaction solution. The NanoNeedle sensor may have the ability to measure minute changes in resistance, down to the fM concentration level. In one embodiment, the NanoNeedle sensor can be used to detect the transient signal of a DNA extension reaction for pH-Sequencing with a signal to noise ratio of approximating 5.

In a second version of the sample embodiment, a NanoBridge may be used. In the exemplary embodiment, the NanoBridge is a depletion mode resistor of the N+/N/N+ type, and it can detect charge modulation using electrical current as readout. The NanoBridge differs significantly from FET-based design with respect to sensing, signal generation, geometry, and operational mode.

Figure 47A:
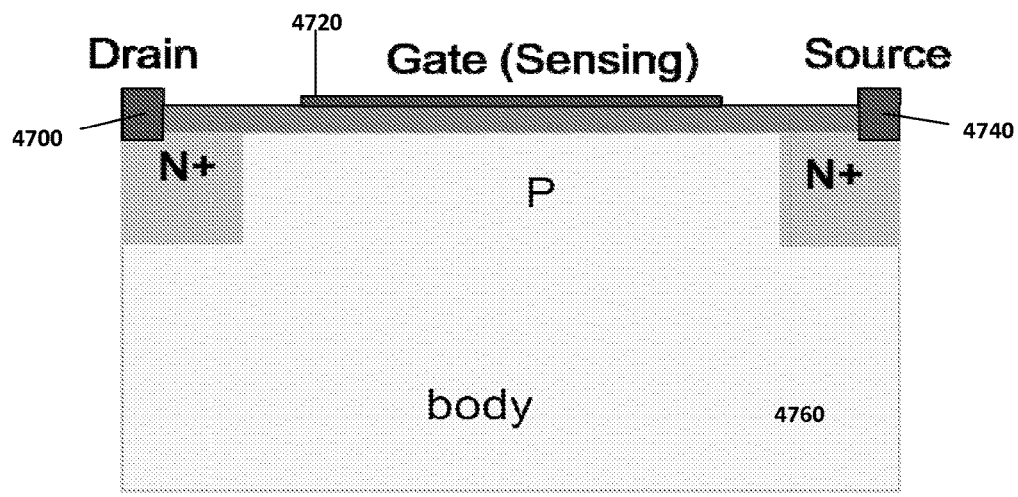
FIG. 47A schematically illustrates an example of a metal-oxide-semiconductor field-effect transistor (MOSFET)
Figure 47B:
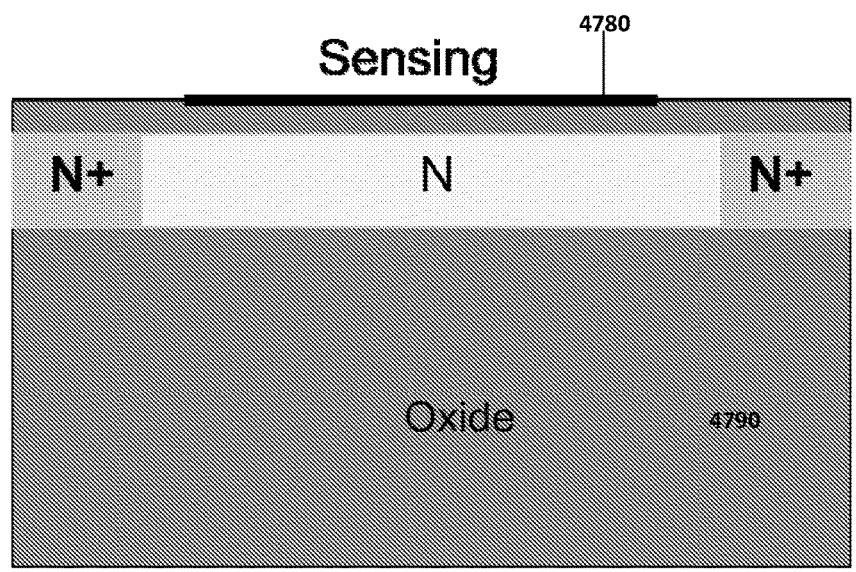
FIG. 47B schematically illustrates an example of a depletion mode nano-resistor.

FIG. 47A shows a MOSFET wherein there is a body 4760 that supports a gate 4720 for sensing, and there is a source 4740 as well as a drain 4700. FIG. 47B shows a depletion mode nano-resistor wherein there is a sensing area 4780 supported by an oxide structure 4790. The conceptual difference of a MOS FET, shown in FIG. 47A, and the depletion mode nano-resistor, shown in FIG. 47B, can be seen by comparing FIGS. 47A and 47B.

One of the key differences is that the NanoBridge may be made of lightly doped semiconductor on a thin SOI (Silicon Over Insulator) wafer, which significantly reduces the depth of the channel. As a consequence, the channel depth is shallower, and the device sensitivity can be higher. The depth of doping across the semiconductor "body" may be 600-1000 nm for the MOS FET versus 60 nm for the NanoBridge, and this may result in a better signal to noise ratio and faster response times.

Figure 47C:
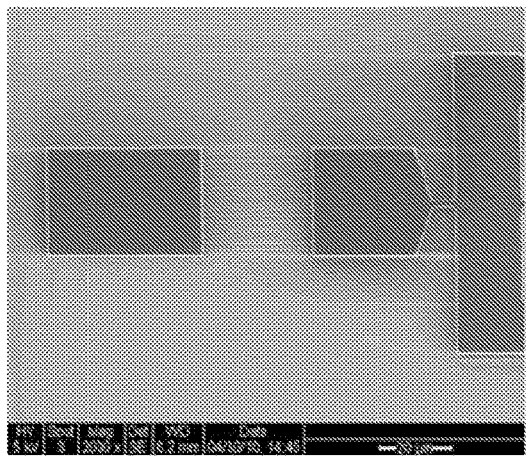
FIG. 47C shows an example of a NanoBridge sensor.

FIG. 47C shows an electron microscopy based photo of the NanoBridge.

Figure 47D:
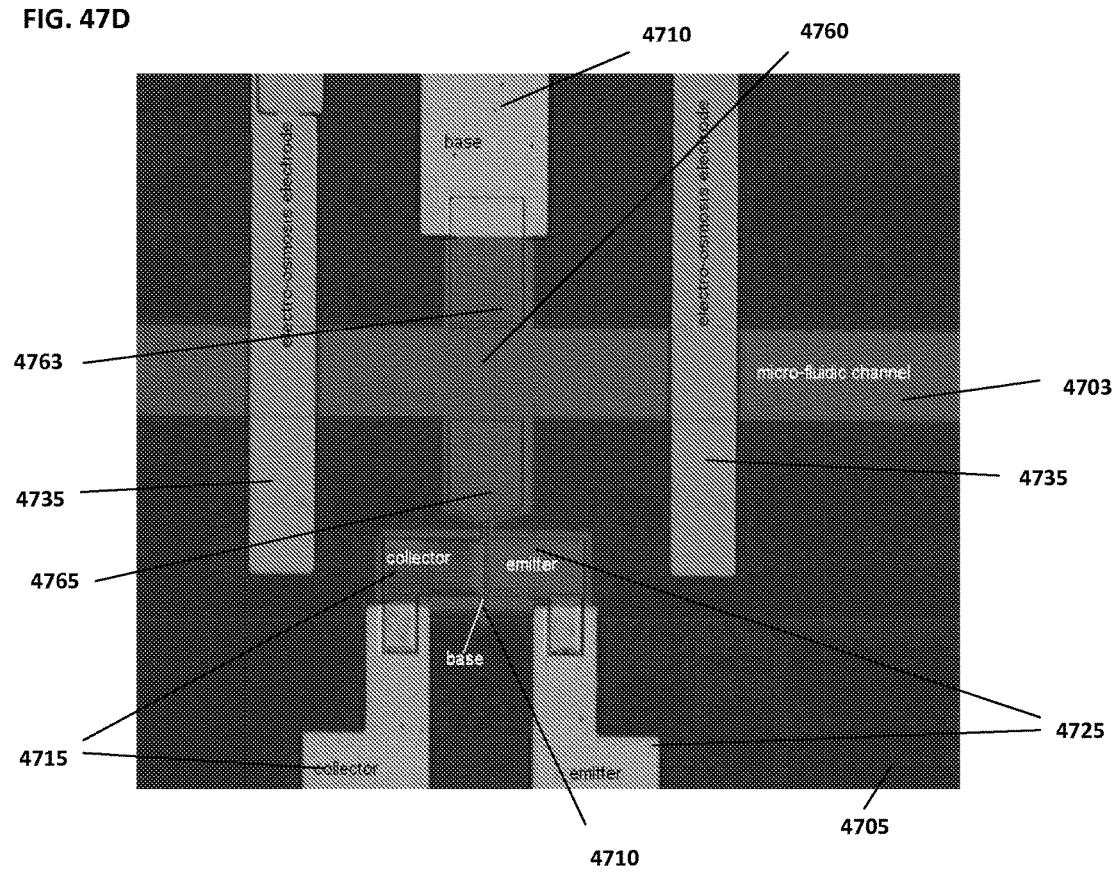
FIG. 47D shows another example of a NanoBridge sensor.

In the exemplary embodiment, FIG. 47D shows a more detailed picture of a NanoBridge sensor, where a SOI structure 4705 is in contact with a microfluidic channel 4703. There is also a sensing portion of the NanoBridge, which includes three semiconductor regions that may be doped to a common polarity, wherein sandwiched semiconductor region 4760 is between two outer semiconductor regions 4765 and 4763. The two outer semiconductor regions 4765 and 4763 may be doped to a higher concentration than sandwiched semiconductor region 4760. Sandwiched semiconductor region 4760 may have a surface directed towards the microfluidic channel 4703 underneath. Microfluidic channel 4703 may pass target materials through the channel, and the target molecules may induce a voltage which changes the surface potential of the semiconductor and the sandwiched region may respond by changing the conductance of said semiconductor region. Also on SOI structure 4705 is an amplification circuit that may comprise at least a bipolar transistor, including a base 4710, a collector 4715, and an emitter 4725 which facilitates sensing of the target materials flowing through microfluidic channel 4703 by way of amplifying the current which passes through sandwiched semiconductor region 4760. Metal electrodes 4735 may be used to bring current in or out of SOI structure 4705.

Figure 48:
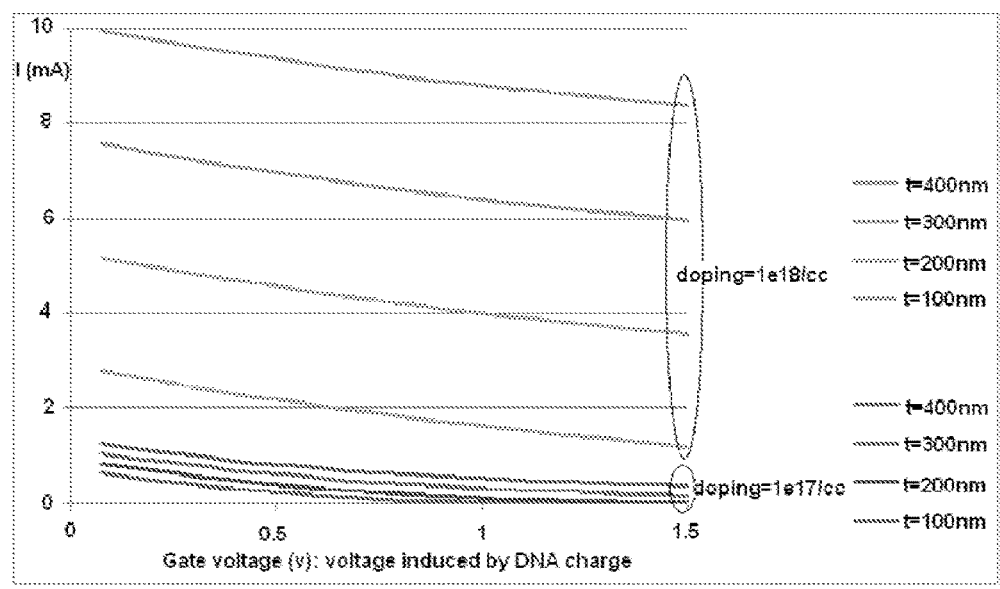
FIG. 48 shows an example of a simulation of signal level as a function of doping levels and silicon on insulator (SOI) thickness.

Thus, for the same voltage applied, the change in signal level can be as much as 3-4 times higher, as shown by the simulation data in FIG. 48. This sensor can also be used to detect pH changes and monitor DNA hybridization events when probe DNA is attached to the sensor surface with a sensitivity of 10 fM. Nano-resistor values may be close to 5 KOhm across the sensor.

In the exemplary embodiment, the NanoBridge sensor channel may have the same polarity as its highly doped (N+) regions. Hence, in contrast to a FET, this device is always in the "ON" state. A reference electrode can be used to provide for consistent measurement in the linear range and minimal signal calibration may be needed due to its naturally linear I-Vg response in low gate voltages (Vgs). The design may be optimized for maximal $\Delta I/I$ where both doping levels and SOI (silicon on insulator) thickness are used as variables, as shown in FIG. 48, wherein the length equals 5 μm, the gate oxide is 6 nm, and the source/drain voltage equals 1.5V. Total current increases proportionally with increasing doping levels and silicon thickness. The linearity of the response shows that the design can allow measurement of charge induced changes over a wide range with low threshold and excellent signal to noise ratios.

In the alternative, for the exemplary embodiment, both the NanoNeedle and the NanoBridge sensors may be used in conjunction. Using the two sensors can permit detection based on complementary detection modalities, may allow for independent signal confirmation, and can increase read accuracy. Both the NanoNeedle and NanoBridge sensors can be used in conjunction with each other on the same nano-sensor array, as shown in FIG. 21. The sensing method of the exemplary embodiment may be dual sensing or multi-sensing detection, and this dual or multi-sensing detection method can be referred to as "SensePlus".

The re-usable sequencing chip in the exemplary embodiment can consist of three major functional components. 1) A CMOS nano-sensor layer above the magnetic capture pixel for electronic detection of single base incorporation. 2) A layer of micro-magnets that may allow for the capture of single magnetic beads loaded with >$10^6$ copies of single stranded sequencing template. 3) A PDMS microfluidic structure that can provide necessary fluidic controls using a valve and channel configuration for single port reagent delivery, with minimal dead volume and fast transition times directly to the sensor array. One embodiment of the re-usable sequencing chip and associated microfluidic channels for input and output flow of regents/target molecules is in the same basic structure as for the re-usable amplification chip, as shown in FIG. 38A, except instead of an amplification array chip there may be sequencing array chip.

Figure 49A:
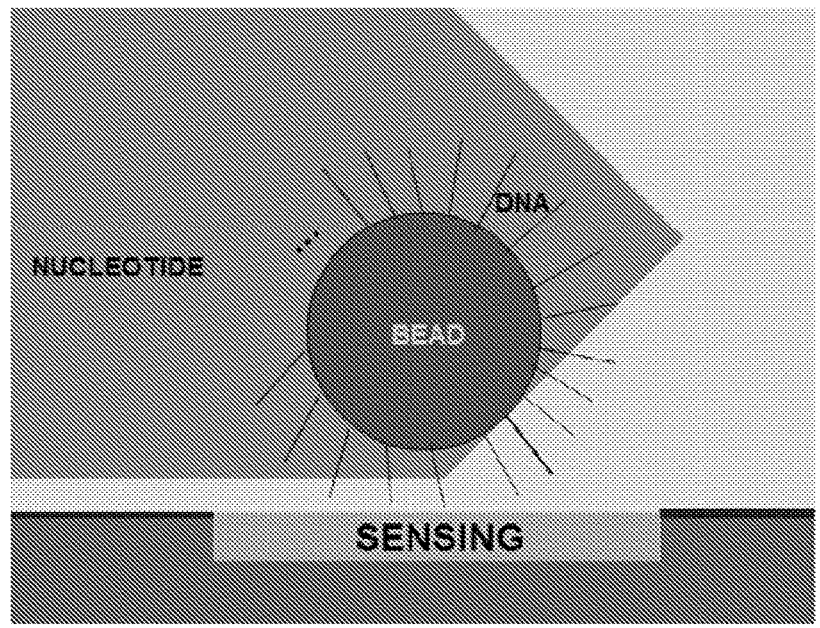
FIG. 49A schematically illustrates an example of a well-less bead capture configuration of a confinement cell.
Figure 49B:
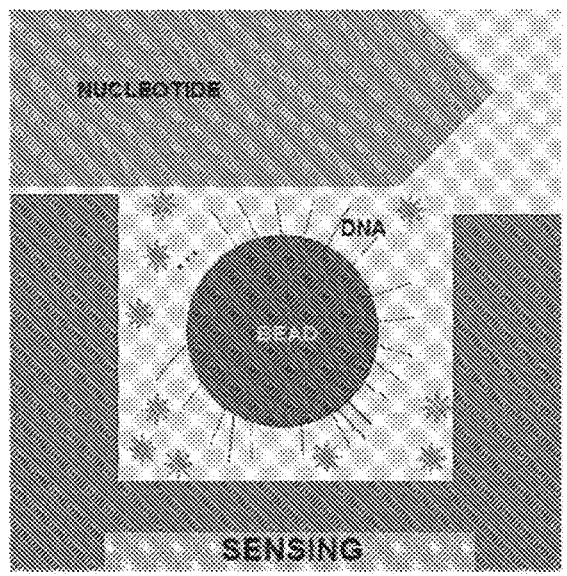
FIG. 49B schematically illustrates an example of a well structure bead capture configuration.

The efficient and uniform reagent delivery and washing, combined with the well-less bead capture of the array of confinement cells, may minimize de-phasing and can provide uniformity of reaction, permitting longer reads and more accurate data, enabling re-use of the chip, and lowering reagent consumption and cost. In an exemplary embodiment, FIG. 49A shows a diagram of a well-less bead capture configuration of a confinement cell that is part of a micro-magnetic array. This type of structure may allow for improvement in flow of reagents, such as for example nucleotides, polymerase, etc., as their flow may not be hindered by a well structure, shown in FIG. 49B. The chamber-free magnetic retention structure of FIG. 49A may permit better washing, more complete incorporation of bases, and faster cycle times than might be possible if the bead were located in a well. If a well structure, bead and associated DNA, such as shown in FIG. 49B, hinders accessibility and flow, higher concentrations of polymerase and nucleotides may be needed to permit sufficient diffusion to all parts of a bead. Said higher concentrations of dNTPs and polymerase may increase an error rate due to misincorporation by said polymerase, resulting in higher levels of leading phase error than may occur with a chamber-free structure, such as the structure of FIG. 49A.

Electronics

In the sample embodiment, each of the sensors may be brought directly out to bondouts on the silicon sensor; each of these may be wire bonded to associated pads on a Chip Carrier PCB board, which may act as an intermediary to the signal processing board, wherein the current can be converted to a voltage by a transimpedance amplifier, and may subsequently be subjected to various linear transformations as needed for the sensor type, such as, for example, reference subtraction, multiplication to remove AC, filtration, etc. The processed analog signals can then sent to a DAC card, from whence they can be stored in a hard disk.

Figure 50A:
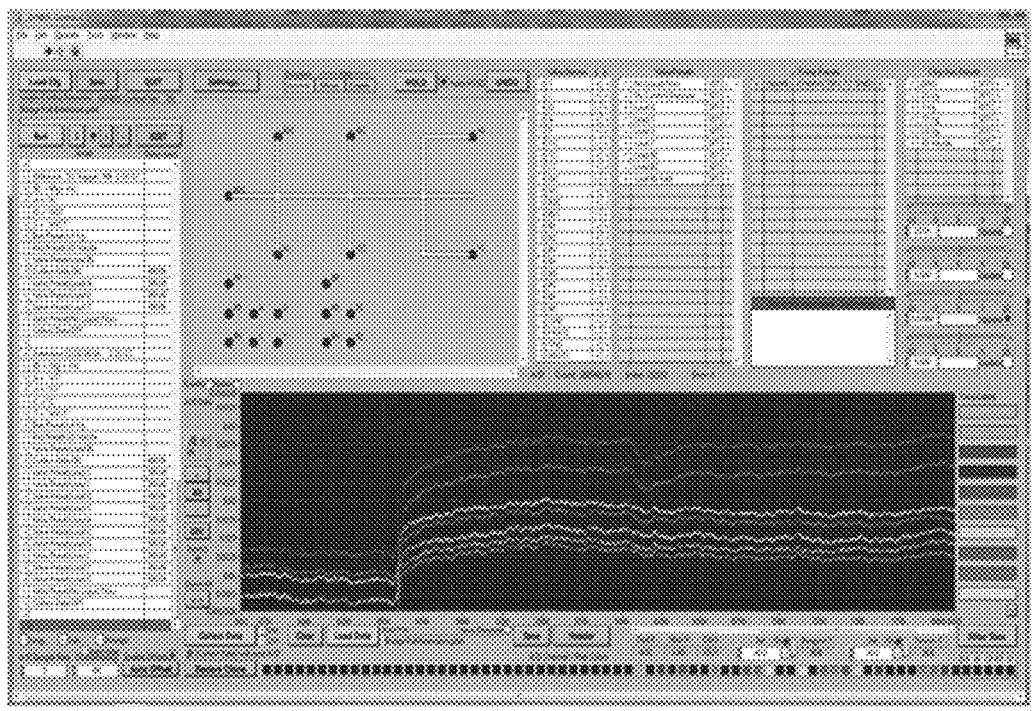
FIG. 50A shows an example of LabView software developed to allow additional signal filtration and offset adjustment.
Figure 50B:
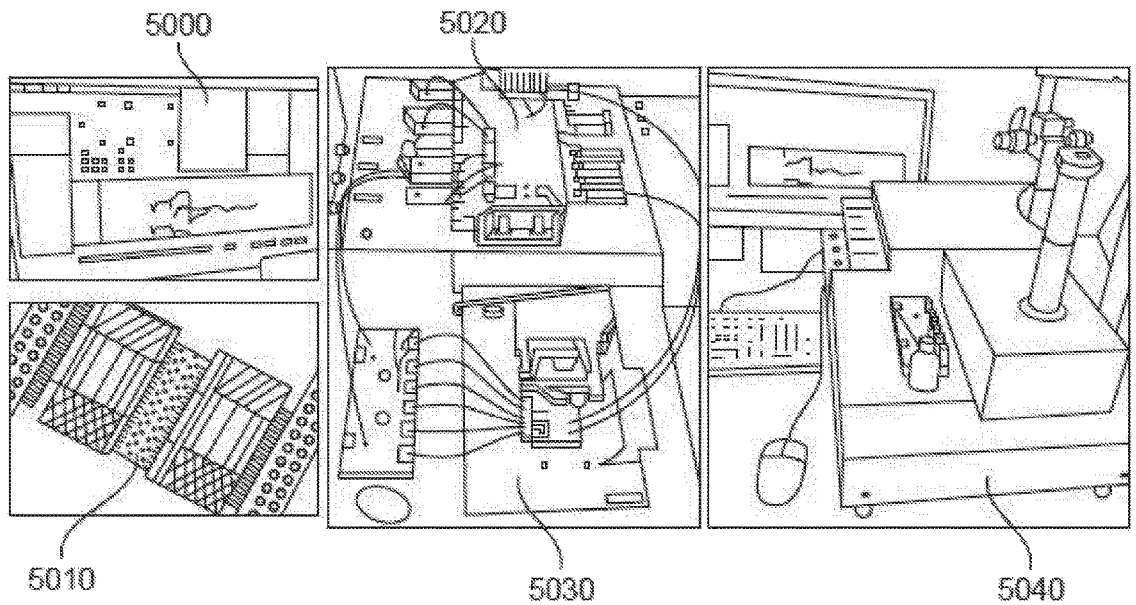
FIG. 50B shows an example of various components of a breadboard.

As shown in FIG. 50A, software in LabView has been developed that allows additional signal filtration and offset adjustment prior to storing the data on a hard drive. FIG. 50B illustrates a sample embodiment of the various components of the breadboards: Labview software display 5000, circuit boards 5010, fluidics controls 5020, chip carrier and reagent block 5030, and assembled system 5040.

In the exemplary embodiment, either in conjunction with data acquisition, or subsequently, the stored data may be baselined, and may have one of several data analysis methods performed on the data to determine the amount of charge or change in conductance that has been introduced to the sensor, and thus whether incorporation has occurred.

Figure 51:
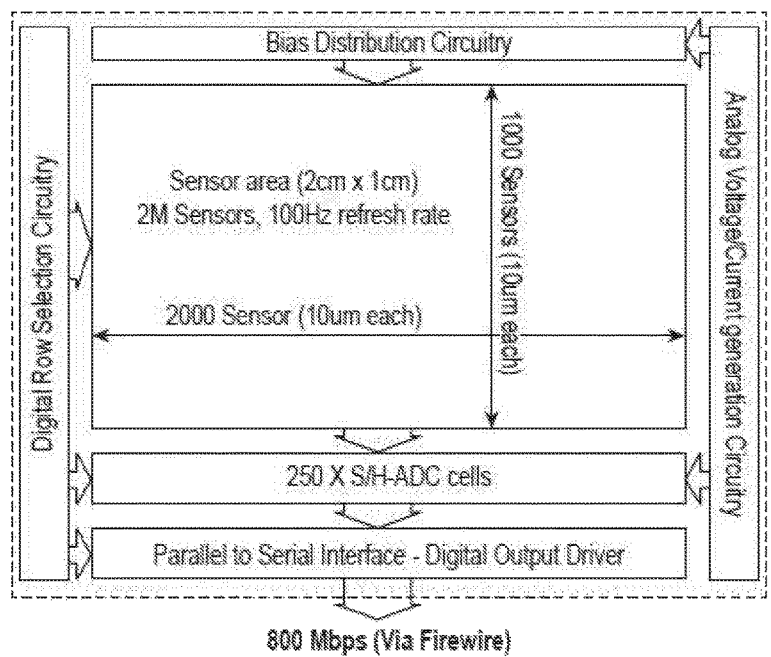
FIG. 51 schematically illustrates an example of a data acquisition card.

The characteristic time of the nucleotide incorporation signal and the number of sensors per array may dictate the data throughput requirements. Data acquisition of 20 independent channels at sampling rates of greater than 1 kHz is well within the capability of commercially available, data acquisition (DAQ) cards. Thus all 20 sensors can be monitored simultaneously, with individual trans-impedance amplifiers, multipliers, and filters as needed for the sensor type. Data can be acquired for every cycle from every sensor. Those sensors without a reaction may be used as references to remove any variation in buffer ion concentration, temperature influences on the system, or other systematic variables. All data can be acquired by a DAC card, which may then buffer the data to a hard disk on a computer prior to data analysis, as shown in FIG. 51.

Experimental Approach: Characterization of Nucleotide Incorporation Signal

The NanoNeedle and NanoBridge sensors may be used to detect the incorporation of a nucleotide by DNA polymerase using a clonal DNA template. In an exemplary process, DNA templates were attached to magnetic beads, either via a streptavidin biotin linkage or directly conjugated, and hybridized to the sequencing primer. After pre-incubation of these beads with DNA polymerase, they were introduced into the sensor device followed by the delivery of dNTP solution to initiate polymerization. The signals from multiple and single base incorporation were recorded. Sensor optimization involves factors such as total current (I), delta current ($\Delta I$), $\Delta I/I$, S/N, short and long term stability and response time. The rate limiting step for signal generation was the reagent delivery through the channel rather than the polymerization reaction (averaging 20 ms). The signal strength may be dependent on the number of DNA templates as well as polymerase, nucleotide and salt concentration.

For proof of concept studies, both sensor type chips were fabricated with an array of functional sensing units (20 to 100 for initial design and 2 million or more in the next step) in a microfluidic channel, for example a PDMS based one. With respect to the chips without integrated magnets within the sensor array, removable magnets underneath the sensor chip were used to capture beads that flowed into the channel. Sequencing was performed using beads preloaded with a single DNA template, primer, and Klenow (exo-) DNA polymerase followed by injection of dNTPs. Other types of DNA polymerase such as BST, Sequanase, Phi29, T4, etc. can be used.

Preliminary Data: Nano-needle Sensor Chip

Figure 52:
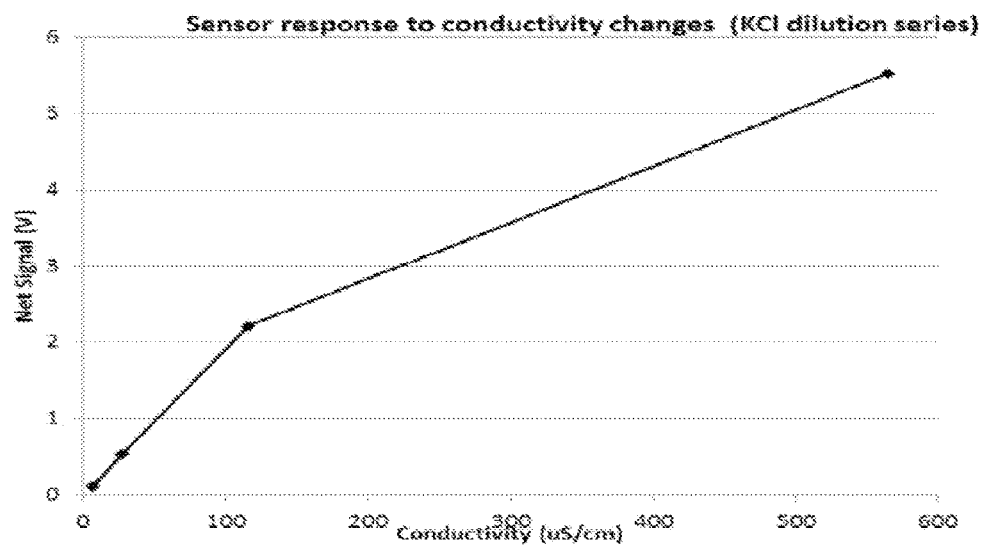
FIG. 52 shows an example sensor response to conductivity changes.

In the example embodiment, the NanoNeedle sensor is fabricated to respond to conductivity changes. Initial experiments are done with salt solutions of various molarities, as shown in FIG. 52. The response to changes in salt concentration is linear between 0.04 mM and 2.0 mM, which is well within the range of changes occurring during the sequencing reaction.

Figure 53A:
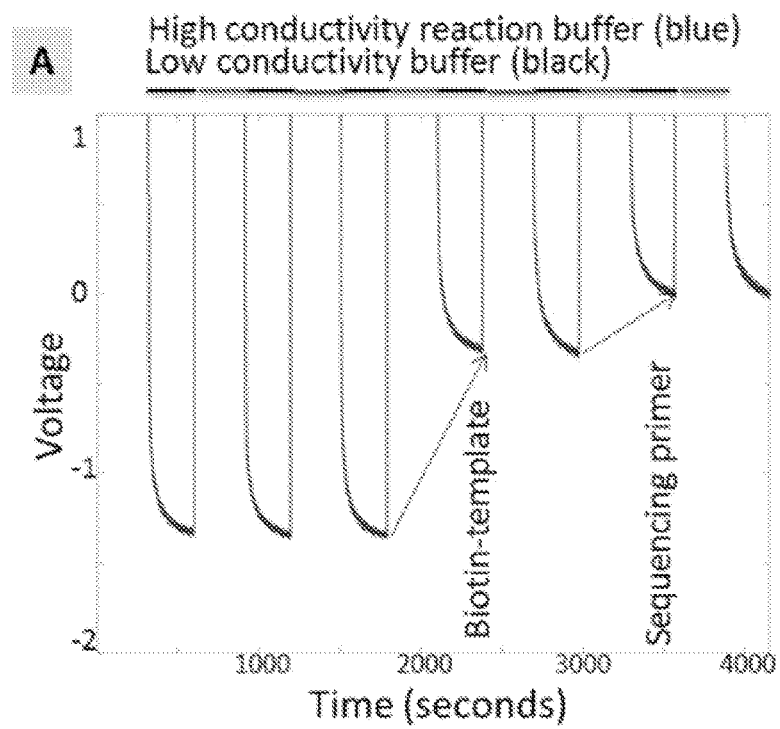
FIG. 53A shows an example of a DNA charge induced sensor response.
Figure 53B:
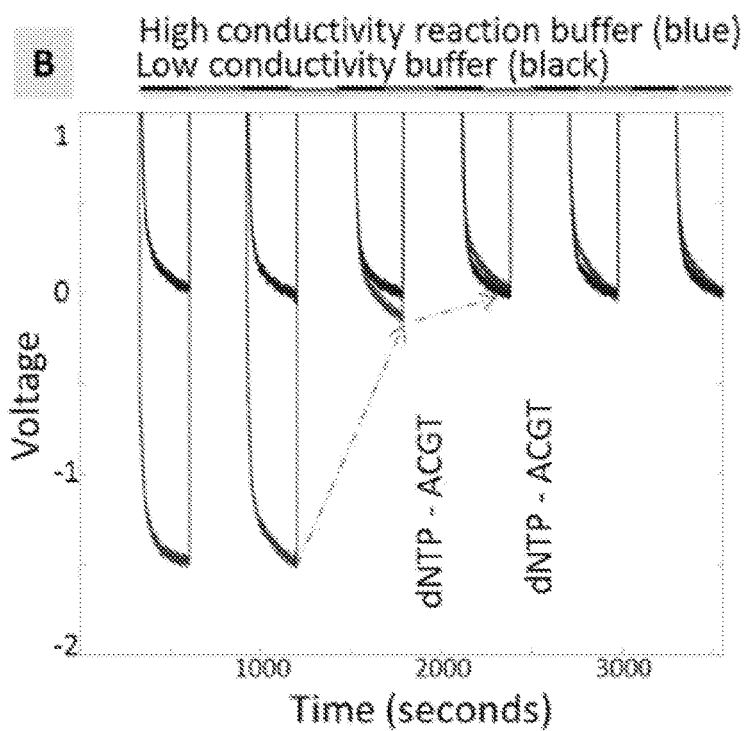
FIG. 53B shows an example of a signal derived from extension of a template.

This initial experiment was followed by characterization of responses to DNA charge, and then sequence extension was performed on template/primer loaded beads. FIG. 53A shows a DNA charge induced sensor response (in Volts) wherein Streptavidin paramagnetic Dynal M270 beads may be captured on top of a sensor. This is followed by injection of a 75 base pair biotinylated DNA oligonucleotide. Binding of the DNA molecules may induce an increase in voltage due to increased negative charge. The response was about 1.2 V for the 75 base pair addition. Subsequently, a 21 base pair complementary sequencing primer is added and this can further increase the signal by about 400 mV (by about ⅓ of the prior signal), indicating primer hybridization. FIG. 53B shows the signal of the full extension of the template. An extension signal is obtained from Streptavidin beads pre-loaded with template, primer, and Klenow DNA polymerase prior to (first two cycles) and after the injection of all four deoxynucleotides to induce full extension. Signal magnitude between the two experiments shows excellent correlation.

FIG. 53A also illustrates that the exemplary embodiment can be used in reactions of interest other than DNA sequencing, such as for example DNA hybridization. The nanosensor array may be used as a DNA hybridization array. As shown in FIG. 53A, the addition of a sequencing primer may result in a change in current that is detected by the nanosensor. The addition of a sequencing primer is essentially an example of the occurrence of DNA hybridization, wherein two complementary strands of DNA bind to each other. The binding of two complementary strands of DNA results in a significant change in voltage and thus the exemplary embodiment may also function as a DNA hybridization array.

FIGS. 17 and 20 show further embodiments of experiments that illustrate the signal output for nano-sensor detection of DNA incorporation for DNA sequencing. FIG. 17 shows the raw data for an exemplary DNA sequencing run wherein the signal changes according to the addition of 3 and 5 bases, but remains flat for zero base addition. FIG. 20 shows how, in one embodiment of an exemplary sequencing experiment, the order of the nucleotides being injected into the sequencing module is "C, A, T, G" and the results of the sequencing data indicate that nucleotides being incorporated are "ATGGAATTGGGAAAAATA" (SEQ ID NO: 3).

The NanoNeedle and NanoBridge sensors can also detect the changes in charge induced by negatively charged DNA molecules and their associated counter-ions. The detection of fixed charge allows for a steady state detection of the base incorporation, with an output profile matching that of FIGS. 53A, 53B, and 17. This may have a number of advantages. First, only a single measurement is needed at any time after completion of the reaction, giving flexibility and greatly reducing the data stream and analysis process. Secondly, reaction conditions can be optimized for long, error free reads, while measurements can be performed in low conductivity buffer to maximize signal and reduce the signal to noise ratio. Additionally, this approach allows for both transient and steady state signal detection, providing two independent measurements of the same reaction. Lastly, since the measured charge is physically associated with the bead on the sensor there may be no cross-talk with adjacent sensors.

Fabrication and Testing of a High Density Combined Micro-magnet-Nano-sensor Array In the exemplary embodiment, the sequencing chip in its final configuration may contain a micro-magnet array in proximity to the sensor array and may consist of several million capture and sensor pixels.

Figure 54A:
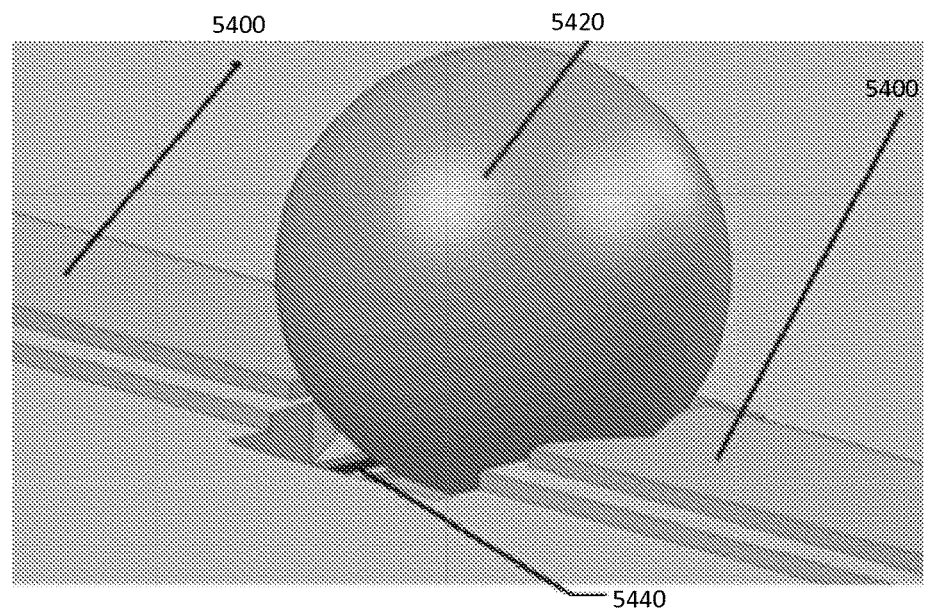
FIG. 54A schematically illustrates using an example NanoNeedle sensor.
Figure 54B:
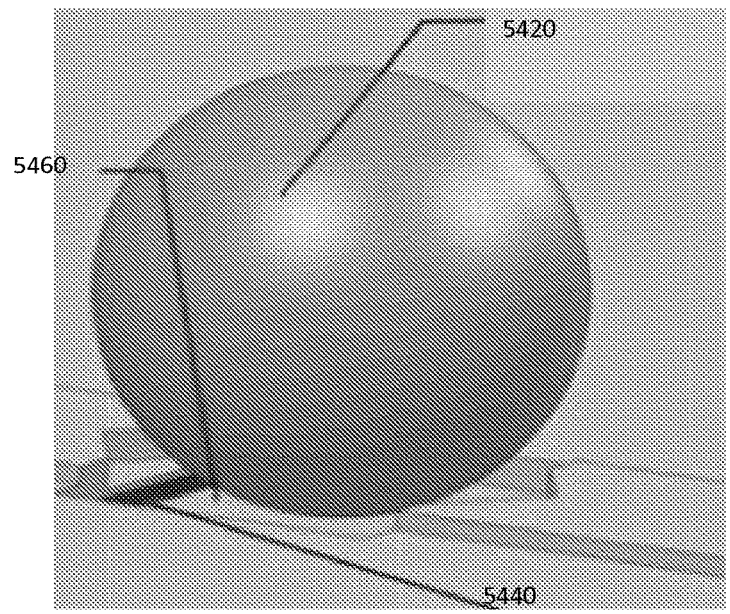
FIG. 54B schematically illustrates an example of a NanoBridge sensor.
Figure 54C:
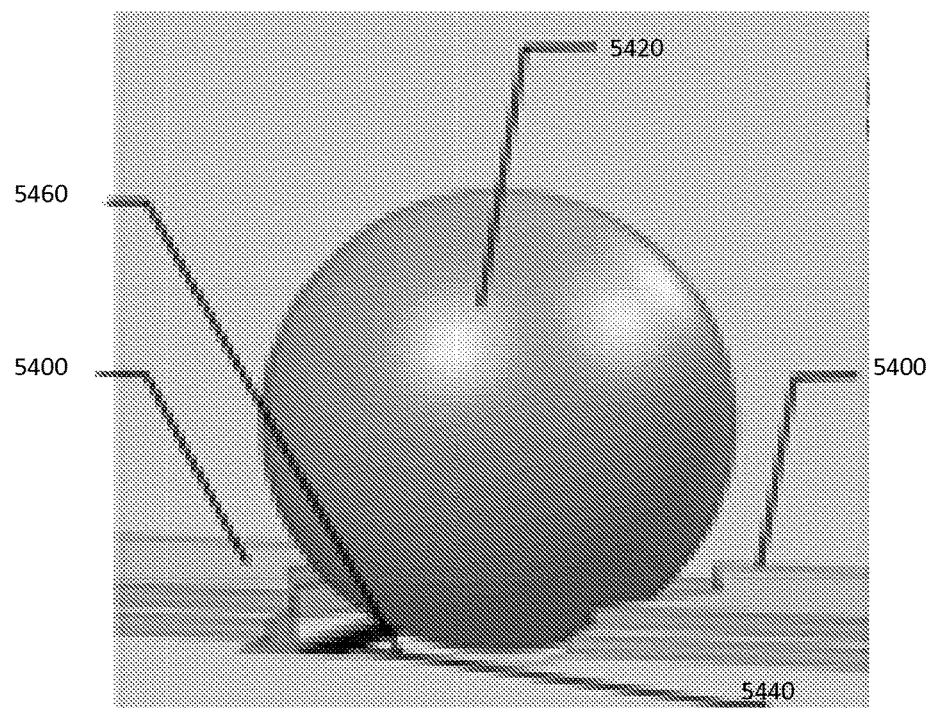
FIG. 54C schematically illustrates an example of a dual sensor configuration with both a NanoNeedle and NanoBridge sensor.

The re-usable sequencing chip may be designed in either a single or dual sensor configuration. FIG. 54A shows the exemplary embodiment using a NanoNeedle sensor wherein NanoNeedle electrodes 5400 are proximal to bead 5420 and said bead is retained by magnetic region 5440. FIG. 54B shows a NanoBridge sensor 5460 located proximal to bead 5420, wherein said bead is retained by magnetic region 5440. FIG. 54C shows a dual sensor configuration wherein both NanoBridge sensor 5460 and NanoNeedle electrodes 5400 are proximal to bead 5420, wherein said bead is retained by magnetic region 5440.

Additionally, further optimization of signal to noise can be performed by taking into account various reaction conditions and adjusting microfluidic components for low dead volume and fast transition during reagent delivery. The elimination of the well structure may reduce the dependence on diffusion for delivery and removal of reagents. This may result in a reduction of reagents and cycle times and can provide better uniformity of reactions, leading to better synchronization and higher signal to noise ratios.

Characterizing the Nucleotide Incorporation Signal and Perform Sequencing on Array Chip In order to better characterize the nucleotide incorporation signal, the signals obtained from individual beads and sensors in dependence of the amount of DNA present on a bead may be defined. There may be some optimization for the range for single bead template concentrations, depending on sequencing reaction conditions. This information can be combined with the signals obtained from adjacent sensors to develop a 'cross talk' signal matrix.

System Component Integration

The integration of the modules (e.g. re-usable chip for emulsion-free sample preparation, bead separation/enrichment module, nano-electronic sequencing platform) do not present a significant challenge because all devices, while designed as stand-alone instruments, are co-developed to optimize the sequencing workflow with respect to cost and quality, as shown in FIG. 36A.

There are a number of options for integration of the different modules for the sample embodiment. The first one is to have fluid pushed from one module to the next. This can be accomplished by scaling each module such that the flow rates from all three devices are compatible with each other. Alternatively, a syringe system with a selector valve may be used to aspirate and dispense fluid containing beads from one module to another. Since the fluidic volumes are small, the beads do not need to enter the syringe but could be aspirated into a service loop. A syringe system can aspirate and dispense at different speeds which allows the flow rates of the system to be highly flexible. Multiple modules can be connected to single syringe delivery systems with a selector valve. Since all the fluids are aqueous with low flow rates, inline electro-osmotic or PDMS peristaltic pumps can be used to pump the reagents.

Figure 55A:
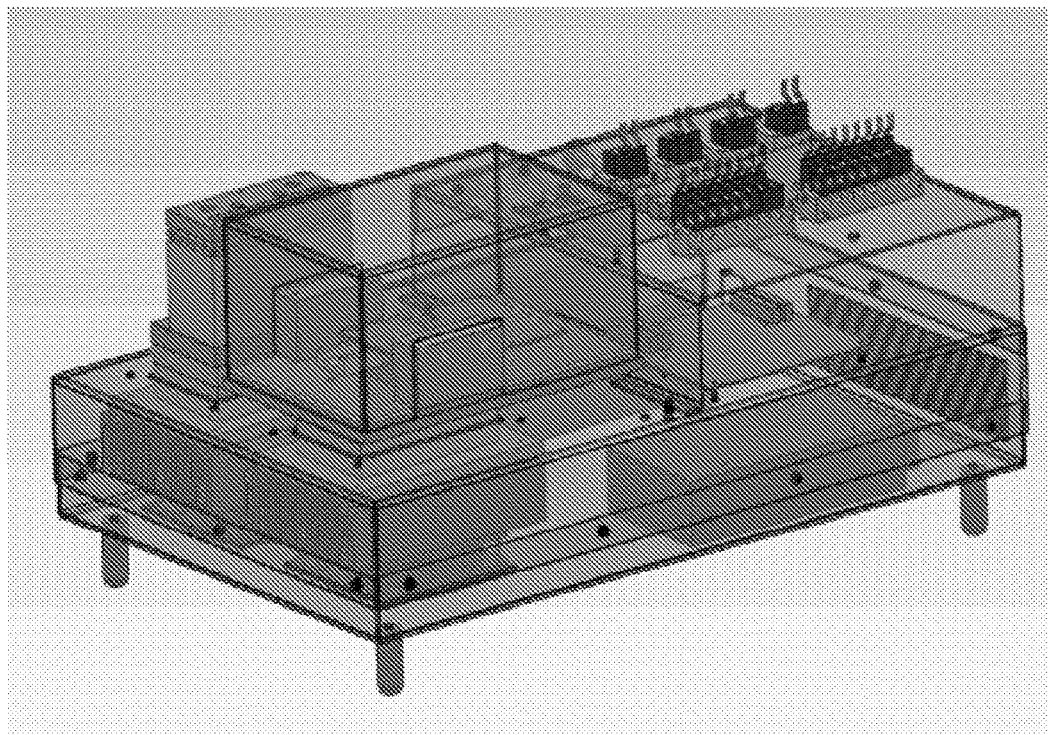
FIG. 55A schematically illustrates an example of an integrated system.
Figure 55B:
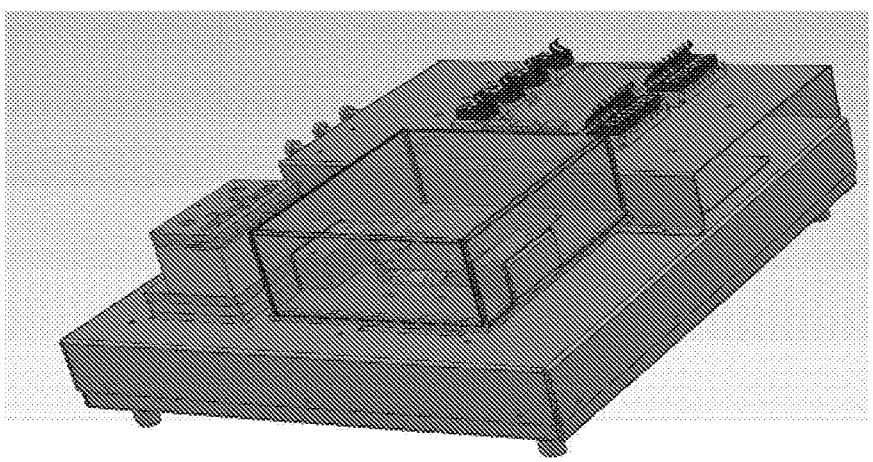
FIG. 55B schematically illustrates an alternative view of an example integrated system.
Figure 56:
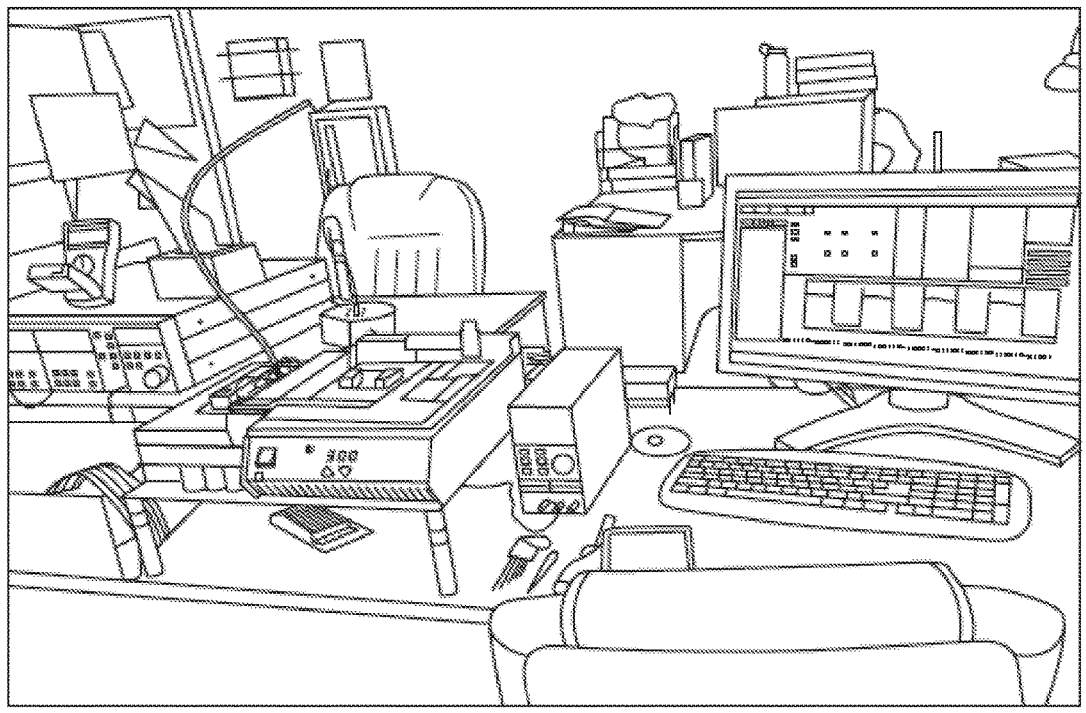
FIG. 56 shows another example of an integrated system.
Figure 57:
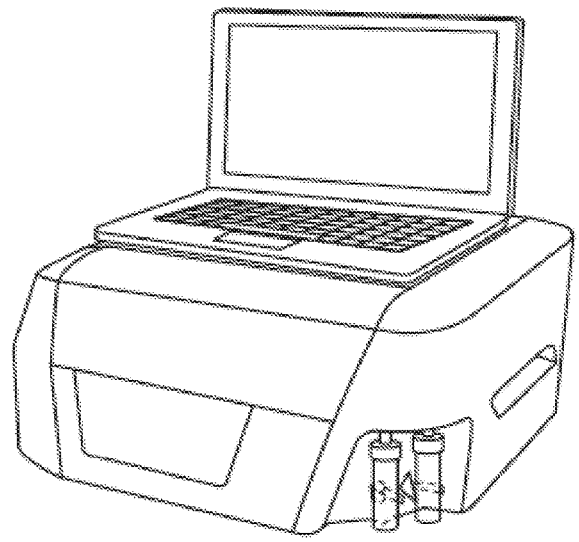
FIG. 57 shows an example of an instrument.

The exemplary integrated system may be contained in an instrument and this instrument may have various embodiments. In one embodiment, the exemplary integrated system is contained in an instrument such as that of FIG. 55A. An alternative view of the instrument of FIG. 55A is shown in FIG. 55B. Another embodiment of the instrument of the exemplary integrated system is shown in FIG. 56, wherein the instrument may be connected to a computer that receives signal information and displays the output using proprietary software. A further embodiment of said instrument is illustrated by FIG. 57, wherein the size of the instrument is compared to the size of a laptop.

The invention claimed is:

1. A method for sequencing a nucleic acid molecule, comprising:
   (a) providing a plurality of particles adjacent to a sensor array, wherein an individual particle of said plurality of particles is positioned adjacent to an individual sensor of said sensor array, wherein said nucleic acid molecule is attached to said individual particle and has a primer hybridized thereto;
   (b) bringing said nucleic acid molecule having said primer hybridized thereto in contact with nucleotides under conditions sufficient to conduct a polymerization reaction to yield a nucleic acid strand complementary to said nucleic acid molecule;
   (c) using said individual sensor to measure steady state signals indicative of impedance, charge, or conductivity change within a Debye length of said individual particle or said nucleic acid molecule, to identify individual incorporation events associated with said nucleotides during said polymerization reaction; and
   (d) using said steady state signals to identify a sequence of said nucleic acid strand, thereby sequencing said nucleic acid molecule.

2. The method of claim 1, further comprising conducting said polymerization reaction in the presence of a reaction buffer that is suitable for the completion of said polymerization reaction, and measuring said steady state signals in the presence of a measurement buffer that is suitable for detecting said steady state signals.

3. The method of claim 2, wherein said reaction buffer and said measurement buffer are different buffers.

4. The method of claim 2, wherein the conductivity of said measurement buffer is lower than the conductivity of said reaction buffer.

5. The method of claim 1, wherein (b) is performed by bringing different types of nucleotides in contact with said nucleic acid molecule having said primer hybridized thereto, one type of nucleotide at a time.

6. The method of claim 1, wherein said individual sensor comprises at least two electrodes that are electrically coupled to the Debye length of said individual particle or said nucleic acid molecule.

7. The method of claim 1, wherein said individual particle is magnetically immobilized to said sensor array.

8. The method of claim 1, further comprising obtaining said steady state signals using differential measurement.

9. The method of claim 8, wherein said differential measurement utilizes (i) at least one particle that does not comprise a nucleic acid as a reference, (ii) a sensor that is not positioned adjacent to a particle as a reference, (iii) another individual sensor of said sensor array that is not subject to a nucleotide incorporation event as a reference, (v) another nucleic acid molecule of known sequence that is coupled to said nucleic acid molecule as a reference, or (vi) a cross-talk deconvolution function matrix.

10. The method of claim 1, wherein measuring said steady state signals does not include detecting a transient pH signal accompanying said individual incorporation events.

11. The method of claim 1, wherein said individual sensor comprises a well.

12. The method of claim 11, wherein said individual particle is held in said well.

13. The method of claim 1, wherein said sensor array includes a flat surface.

14. The method of claim 13, wherein said individual particle is held adjacent to said individual sensor on said flat surface.

15. The method of claim 1, wherein said individual particle is electrically immobilized to said sensor array.

* * * * *

SEQUENCE LISTING

<160> NUMBER OF SEQ ID NOS: 3

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaaacccc cctttttaa aattttcccc aaccaaccca actcagtcgt caatcaccag      60
a                                                                    61

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaacccc cctttttaa aattttcccc aa                                   32

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atggaattgg gaaaaata                                                  18